(12) United States Patent
Wilkinson et al.

(10) Patent No.: US 8,998,911 B2
(45) Date of Patent: Apr. 7, 2015

(54) METHODS AND APPARATUS FOR PERFORMING KNEE ARTHROPLASTY

(75) Inventors: Zachary Christopher Wilkinson, Germantown, TN (US); Brian W. McKinnon, Bartlett, TN (US); David A. Drucker, Staten Island, NY (US); Michael D. Ries, Nicasio, CA (US)

(73) Assignee: Smith & Nephew, Inc., Memphis, TN (US)

( * ) Notice: Subject to any disclaimer, the term of this patent is extended or adjusted under 35 U.S.C. 154(b) by 892 days.

(21) Appl. No.: 12/790,137

(22) Filed: May 28, 2010

(65) Prior Publication Data

US 2010/0331991 A1  Dec. 30, 2010

Related U.S. Application Data

(60) Provisional application No. 61/182,435, filed on May 29, 2009, provisional application No. 61/299,835, filed on Jan. 29, 2010.

(51) Int. Cl.
| | | |
|---|---|---|
| *A61F 2/38* | (2006.01) |
| *A61B 17/58* | (2006.01) |
| *A61B 17/60* | (2006.01) |
| *A61F 2/00* | (2006.01) |
| *A61F 2/46* | (2006.01) |
| *A61B 17/16* | (2006.01) |

(Continued)

(52) U.S. Cl.
CPC .............. *A61B 17/16* (2013.01); *A61B 17/155* (2013.01); *A61B 17/157* (2013.01); *A61B 17/1764* (2013.01); *A61F 2/4684* (2013.01); *A61F 2/3859* (2013.01); *A61F 2/389* (2013.01)

(58) Field of Classification Search
CPC .......... A61B 2017/00716; A61B 2017/00707; A61B 17/155
USPC ................. 33/512; 623/20.21, 20.35; 606/88
See application file for complete search history.

(56) References Cited

U.S. PATENT DOCUMENTS

| 3,798,679 A | 3/1974 | Ewald |
| 4,081,866 A * | 4/1978 | Upshaw et al. ............ 623/20.21 |

(Continued)

FOREIGN PATENT DOCUMENTS

| CN | 101237835 | 8/2008 |
| EP | 0121142 | 7/1987 |

(Continued)

OTHER PUBLICATIONS

International Search Report and Written Opinion dated Feb. 8, 2011 in related Application No. PCT/US2010/036632.

(Continued)

*Primary Examiner* — David Bates
(74) *Attorney, Agent, or Firm* — Fish & Richardson P.C.

(57) ABSTRACT

Methods and apparatus for performing knee arthroplasty, including, but not limited to, bicruciate retaining knee arthroplasty, are described herein. Methods and apparatus for preparing a distal femur for a femoral implant as well as methods and apparatus for preparing a proximal tibia for a tibial implant are described. These methods and apparatus, in at least some embodiments and uses, facilitate decreasing the complexity of knee arthroplasty procedures such as bicruciate retaining procedures, while maintaining, if not improving on, the safety, accuracy and/or effectiveness of such procedures.

43 Claims, 65 Drawing Sheets

(51) Int. Cl.
*A61B 17/15* (2006.01)
*A61B 17/17* (2006.01)

(56) References Cited

U.S. PATENT DOCUMENTS

| | | | |
|---|---|---|---|
| 4,211,228 A | 7/1980 | Cloutier | |
| 4,249,270 A | 2/1981 | Bahler et al. | |
| 4,474,177 A | 10/1984 | Whiteside | |
| 4,524,766 A | 6/1985 | Petersen | |
| 4,568,348 A | 2/1986 | Johnson et al. | |
| 4,586,933 A | 5/1986 | Shoji et al. | |
| 4,653,488 A | 3/1987 | Kenna et al. | |
| 4,703,751 A | 11/1987 | Pohl | |
| 4,711,639 A | 12/1987 | Grundel | |
| 4,722,330 A | 2/1988 | Russell et al. | |
| 4,738,254 A * | 4/1988 | Buechel et al. | 606/96 |
| 4,787,383 A | 11/1988 | Kenna | |
| 4,907,578 A | 3/1990 | Petersen | |
| 4,926,847 A | 5/1990 | Luckman | |
| 4,938,769 A | 7/1990 | Shaw | |
| 4,950,298 A | 8/1990 | Gustilo et al. | |
| 4,952,213 A | 8/1990 | Bowman | |
| 4,963,152 A | 10/1990 | Hofmann et al. | |
| 4,979,949 A | 12/1990 | Matsen, III et al. | |
| 5,002,545 A | 3/1991 | Whiteside et al. | |
| 5,007,933 A | 4/1991 | Sidebotham et al. | |
| 5,037,423 A | 8/1991 | Kenna | |
| 5,053,037 A | 10/1991 | Lackey | |
| 5,062,852 A | 11/1991 | Dorr et al. | |
| 5,080,675 A | 1/1992 | Lawes et al. | |
| 5,098,436 A | 3/1992 | Ferrante et al. | |
| 5,122,144 A | 6/1992 | Bert et al. | |
| 5,236,432 A | 8/1993 | Matsen, III et al. | |
| 5,282,803 A | 2/1994 | Lackey | |
| 5,342,368 A | 8/1994 | Petersen | |
| 5,356,414 A | 10/1994 | Cohen et al. | |
| 5,417,694 A | 5/1995 | Marik et al. | |
| 5,451,228 A | 9/1995 | Johnson et al. | |
| 5,462,549 A * | 10/1995 | Glock | 606/86 R |
| 5,464,406 A * | 11/1995 | Ritter et al. | 606/86 R |
| 5,470,354 A | 11/1995 | Hershberger et al. | |
| 5,474,559 A | 12/1995 | Bertin et al. | |
| 5,609,645 A | 3/1997 | Vinciguerra | |
| 5,611,802 A | 3/1997 | Samuelson et al. | |
| 5,667,511 A | 9/1997 | Vendrely et al. | |
| 5,681,316 A | 10/1997 | DeOrio et al. | |
| 5,683,469 A | 11/1997 | Johnson et al. | |
| 5,688,280 A | 11/1997 | Booth, Jr. et al. | |
| 5,690,637 A | 11/1997 | Wen et al. | |
| 5,702,464 A | 12/1997 | Lackey | |
| 5,776,200 A | 7/1998 | Johnson et al. | |
| 5,776,201 A | 7/1998 | Colleran et al. | |
| 5,782,925 A | 7/1998 | Collazo et al. | |
| 5,830,216 A | 11/1998 | Insall | |
| 5,916,220 A * | 6/1999 | Masini | 606/88 |
| 6,059,788 A | 5/2000 | Katz | |
| 6,258,095 B1 * | 7/2001 | Lombardo et al. | 606/88 |
| 6,482,209 B1 | 11/2002 | Engh et al. | |
| 6,488,687 B1 * | 12/2002 | Masini | 606/88 |
| 6,569,202 B2 | 5/2003 | Whiteside | |
| 6,575,980 B1 | 6/2003 | Robie et al. | |
| 6,770,077 B2 | 8/2004 | Van Zile et al. | |
| 7,128,745 B2 * | 10/2006 | Masini | 606/88 |
| 7,419,491 B2 * | 9/2008 | Masini | 606/87 |
| 7,695,520 B2 | 4/2010 | Metzger et al. | |
| 8,025,663 B2 * | 9/2011 | Keeven et al. | 606/86 R |
| 8,273,131 B2 | 9/2012 | Metzger et al. | |
| 8,500,818 B2 | 8/2013 | Metzger et al. | |
| 8,529,631 B2 * | 9/2013 | Donno et al. | 623/20.15 |
| 2001/0001121 A1 * | 5/2001 | Lombardo et al. | 606/89 |
| 2002/0055784 A1 | 5/2002 | Burstein et al. | |
| 2002/0173797 A1 | 11/2002 | Van Zile et al. | |
| 2002/0173852 A1 | 11/2002 | Felt et al. | |
| 2003/0028196 A1 | 2/2003 | Bonutti | |
| 2003/0130665 A1 | 7/2003 | Pinczewski et al. | |
| 2004/0138755 A1 | 7/2004 | O'Connor et al. | |
| 2004/0153066 A1 | 8/2004 | Coon et al. | |
| 2004/0153162 A1 | 8/2004 | Sanford et al. | |
| 2005/0010302 A1 | 1/2005 | Dietz et al. | |
| 2005/0143746 A1 | 6/2005 | Steffensmeier et al. | |
| 2005/0149041 A1 | 7/2005 | McGinley et al. | |
| 2005/0154394 A1 | 7/2005 | Michalowicz | |
| 2005/0177169 A1 | 8/2005 | Fisher et al. | |
| 2006/0015109 A1 | 1/2006 | Haines | |
| 2006/0015115 A1 | 1/2006 | Haines | |
| 2006/0015116 A1 | 1/2006 | Haines | |
| 2006/0015117 A1 | 1/2006 | Haines | |
| 2006/0030944 A1 | 2/2006 | Haines | |
| 2006/0036257 A1 | 2/2006 | Steffensmeier et al. | |
| 2006/0155294 A1 | 7/2006 | Steffensmeier et al. | |
| 2006/0189998 A1 | 8/2006 | Rasmussen | |
| 2006/0200158 A1 | 9/2006 | Farling et al. | |
| 2007/0078517 A1 | 4/2007 | Engh et al. | |
| 2007/0173849 A1 | 7/2007 | Claypool et al. | |
| 2007/0219560 A1 | 9/2007 | Hodorek | |
| 2007/0233139 A1 | 10/2007 | Metcalfe et al. | |
| 2007/0233140 A1 | 10/2007 | Metzger et al. | |
| 2007/0282451 A1 | 12/2007 | Metzger et al. | |
| 2008/0058945 A1 | 3/2008 | Hajaj | |
| 2008/0119938 A1 | 5/2008 | Oh | |
| 2008/0140212 A1 | 6/2008 | Metzger et al. | |
| 2008/0161815 A1 | 7/2008 | Schoenefeld et al. | |
| 2008/0188855 A1 * | 8/2008 | Brown et al. | 606/88 |
| 2009/0043309 A1 | 2/2009 | Rasmussen | |
| 2009/0043310 A1 | 2/2009 | Rasmussen | |
| 2009/0112212 A1 | 4/2009 | Murray et al. | |
| 2009/0222014 A1 | 9/2009 | Bojarski et al. | |
| 2009/0264890 A1 | 10/2009 | Duggineni et al. | |
| 2009/0307893 A1 | 12/2009 | Burdulis, Jr. et al. | |
| 2010/0010635 A1 | 1/2010 | Straszheim-Morley et al. | |
| 2010/0016977 A1 | 1/2010 | Masini | |
| 2010/0016980 A1 | 1/2010 | Donno et al. | |
| 2010/0094301 A1 | 4/2010 | Dees, Jr. et al. | |
| 2010/0160919 A1 | 6/2010 | Axelson et al. | |
| 2010/0198224 A1 | 8/2010 | Metzger et al. | |
| 2010/0280624 A1 | 11/2010 | Engh et al. | |
| 2010/0305575 A1 | 12/2010 | Wilkinson et al. | |
| 2010/0305711 A1 | 12/2010 | McKinnon et al. | |
| 2010/0324692 A1 | 12/2010 | Uthgenannt et al. | |
| 2010/0331847 A1 | 12/2010 | Wilkinson et al. | |
| 2010/0331848 A1 | 12/2010 | Smith et al. | |
| 2011/0015749 A1 | 1/2011 | Engh et al. | |
| 2011/0046735 A1 | 2/2011 | Metzger et al. | |
| 2013/0030538 A1 | 1/2013 | Metzger et al. | |
| 2013/0184713 A1 | 7/2013 | Bojarski et al. | |
| 2013/0197527 A1 | 8/2013 | Nadzadi et al. | |

FOREIGN PATENT DOCUMENTS

| | | |
|---|---|---|
| EP | 0337901 | 10/1989 |
| EP | 0380451 | 8/1990 |
| EP | 0327249 | 5/1992 |
| EP | 0336774 | 12/1992 |
| EP | 0243109 | 9/1993 |
| EP | 0780093 | 6/1997 |
| EP | 0555003 | 11/1998 |
| EP | 1136045 | 9/2001 |
| EP | 1862149 | 12/2007 |
| EP | 2168537 | 3/2010 |
| FR | 2742037 A1 | 6/1997 |
| FR | 2915870 A1 | 11/2008 |
| JP | 1011541 | 1/1989 |
| JP | 02246971 | 10/1990 |
| JP | 04297254 | 10/1992 |
| WO | WO 9110408 | 7/1991 |
| WO | WO 9409730 | 5/1994 |
| WO | WO 9601588 | 1/1996 |
| WO | WO 9729704 | 8/1997 |
| WO | WO03059203 | 7/2003 |
| WO | WO 2008030842 | 3/2005 |
| WO | 2006012370 | 2/2006 |
| WO | WO2006088684 | 8/2006 |
| WO | 2008091358 | 7/2008 |
| WO | 2009102725 | 8/2009 |

(56) References Cited

FOREIGN PATENT DOCUMENTS

| WO | WO 2010006677 | 1/2010 |
|----|---------------|--------|
| WO | WO2010138805  | 12/2010 |
| WO | WO2010138836  | 12/2010 |
| WO | WO2010138841  | 12/2010 |
| WO | WO2010138854  | 12/2010 |
| WO | WO2010138857  | 12/2010 |

OTHER PUBLICATIONS

International Search Report and Written Opinion dated Feb. 9, 2011 in related Application No. PCT/US2010/036617.
International Search Report and Written Opinion dated Feb. 17, 2011 in related Application No. PCT/US2010/036642.
International Search Report and Written Opinion dated Feb. 7, 2011 in related Application No. PCT/US2010/036608.
International Search Report and Written Opinion dated Feb. 14, 2011 in related Application No. PCT/US2010/036638.
Office Action for U.S. Appl. No. 12/790,312, mailed Jun. 11, 2013.
Office Action for U.S. Appl. No. 12/790,036, mailed May 29, 2013.
Office Action for U.S. Appl. No. 12/790,227, mailed Jun. 5, 2013.
Office Action for U.S. Appl. No. 12/790,312, mailed Sep. 30, 2013.
Office Action for U.S. Appl. No. 12/790,227, mailed Oct. 1, 2013.
Brochure "TriathlonTM Knee System Design Rationale Surgical Instrumentation and Implants Knee Technology Designed for Natural Motion," 16 pages, 2004, Stryker.
Crossett, L.S., et al., "AMK Congruency Instrument System, Surgical Technique," published by DePuy, 1997, Bates No. DEP00004252-DEP00004267, 17 pages.
Desjardins, D., et al., "Interax Operative Techniques," Interax, 1994, Bates No. DEP00004391-DEP00004411, 22 pages.
Office Action for U.S. Appl. No. 11/933,298, mailed Dec. 2, 2010.
Office Action for U.S. Appl. No. 12/790,002, mailed Oct. 19, 2012.
Office Action for U.S. Appl. No. 12/790,036 mailed Nov. 6, 2012.
Office Action for U.S. Appl. No. 12/790,227, mailed Nov. 2, 2012.
Office Action for U.S. Appl. No. 12/790,312, mailed Nov. 8, 2012.
Whiteside Ortholoc Total Knee System, Dow Corning Wright, pp. ZH0001 09679-ZH0001 09690, 13 pages, 1983.
Notice of Allowance for U.S. Appl. No. 12/790,227, mailed Jan. 8, 2014, 9 pages.
Communication from EPO for EP Application No. 10781300.8, Nov. 6, 2012, 7 pages.
Communication from EPO for EP Application No. 10781303.2, Jan. 24, 2013, 6 pages.
Office Action for Russian Application No. 2011152799/14 mailed Apr. 3, 2014, 5 pages.
Office Action in Chinese Application 201080034672.4, mailed Mar. 20, 2014, 24 pages.
Extended European Search Report for European Application 10781292.7, mailed Sep. 23, 2014.
Extended European Search Report for European Application 10781304.0, mailed Oct. 10, 2014.
Extended European Search Report for European Application 10781287.7, mailed Oct. 13, 2014.
Second Office Action for Chinese Application No. 201080034668.8, mailed Nov. 17, 2014.

* cited by examiner

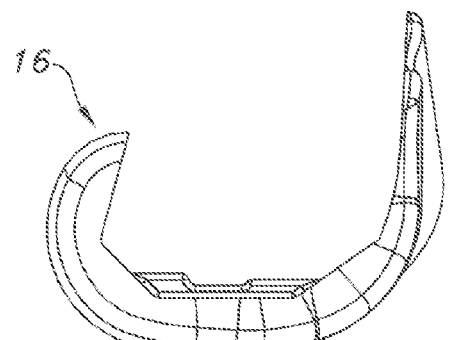
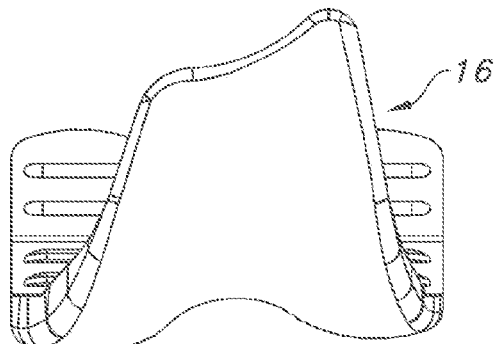
FIG. 7A    FIG. 7D
FIG. 7B    FIG. 7E
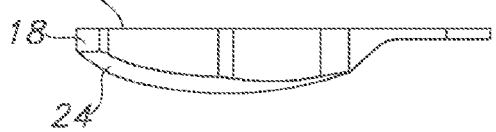
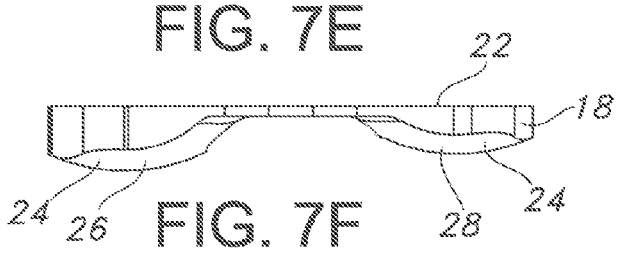
FIG. 7C    FIG. 7F
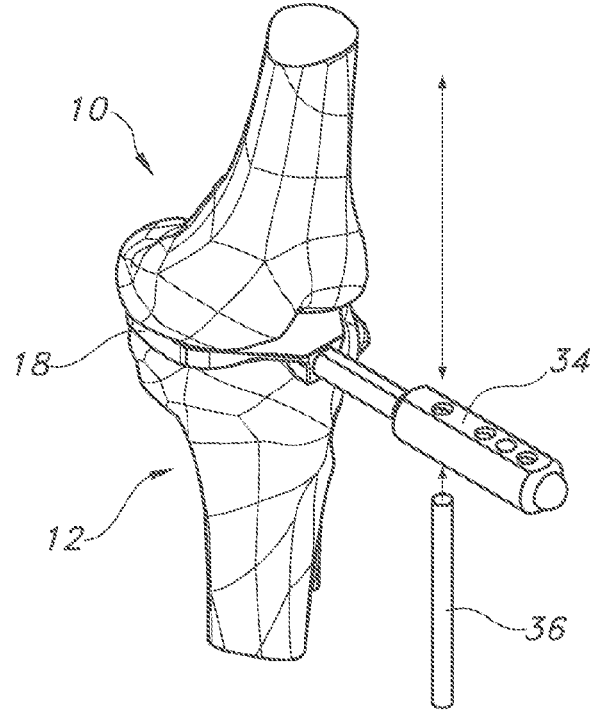
FIG. 8

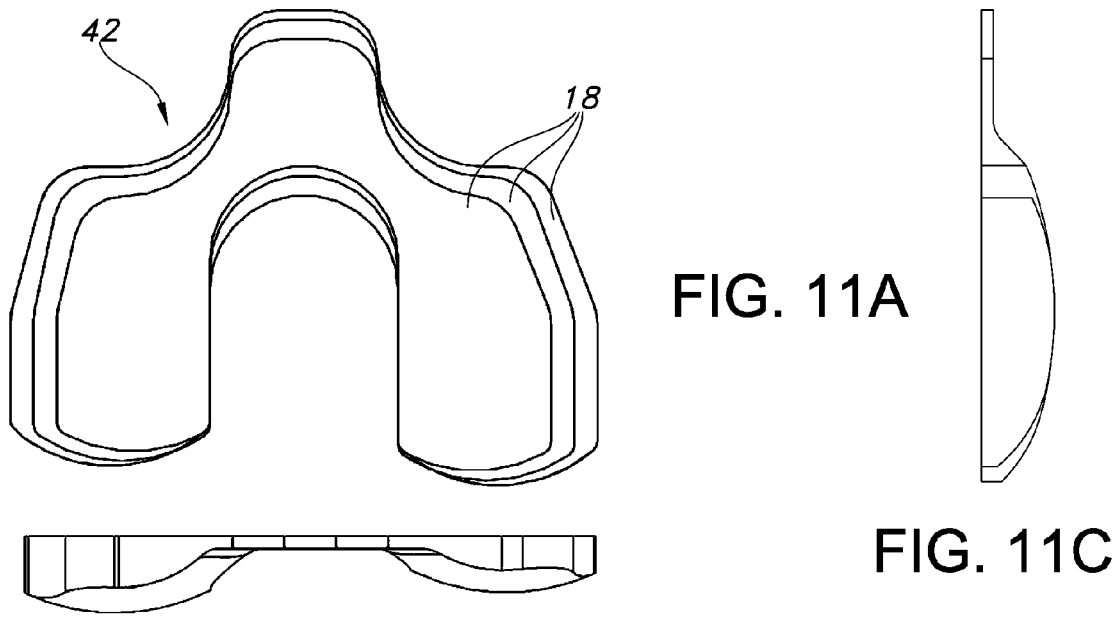
FIG. 11A
FIG. 11B
FIG. 11C
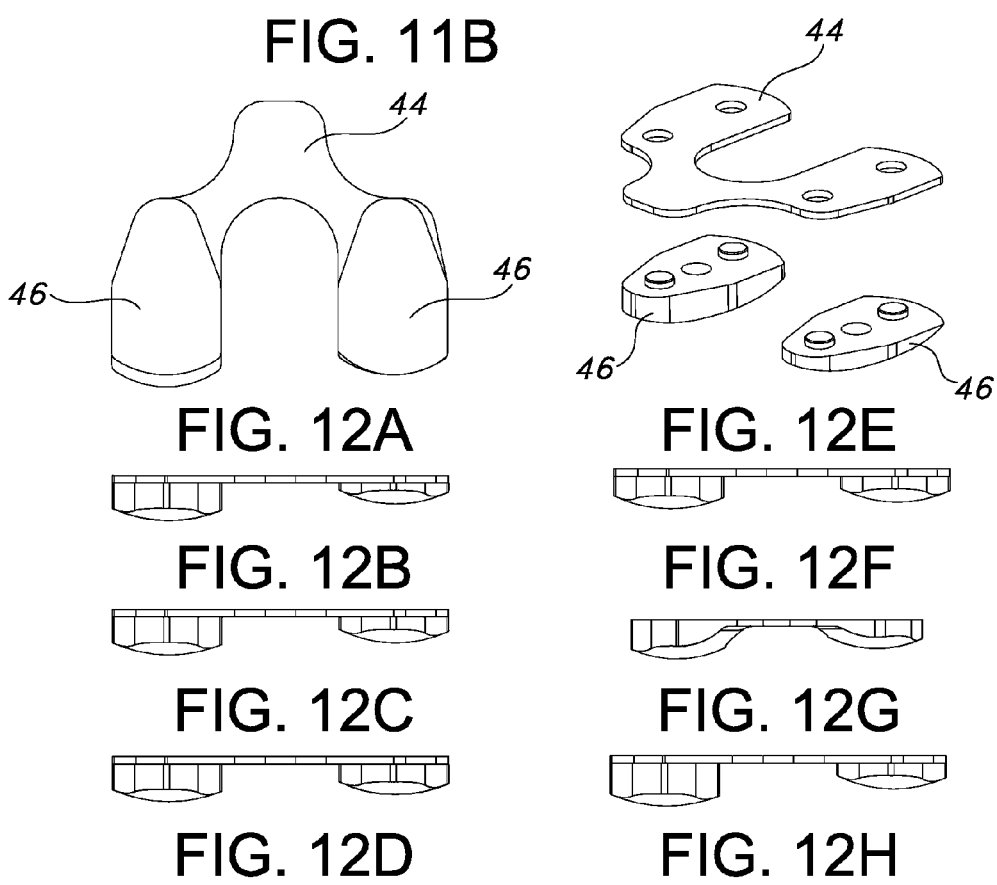
FIG. 12A
FIG. 12B
FIG. 12C
FIG. 12D
FIG. 12E
FIG. 12F
FIG. 12G
FIG. 12H

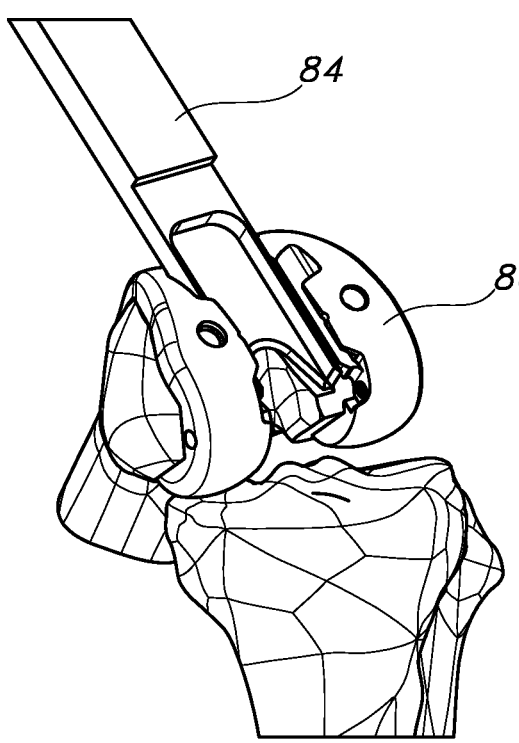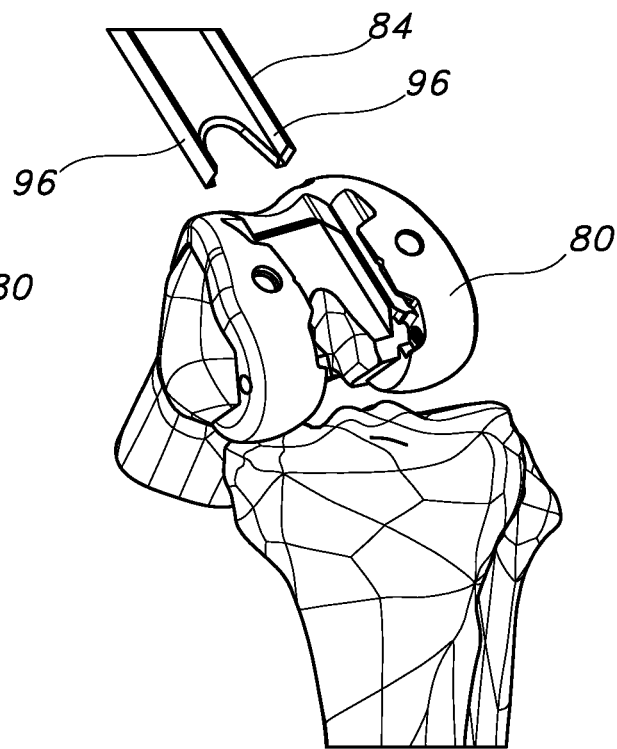
FIG. 27A    FIG. 27B
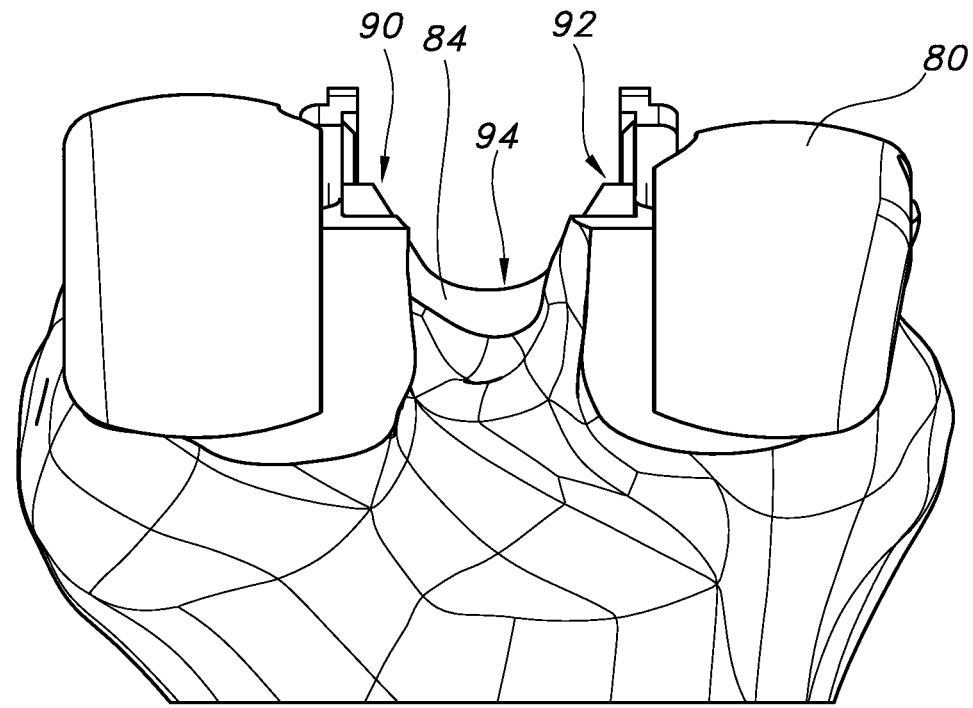
FIG. 28

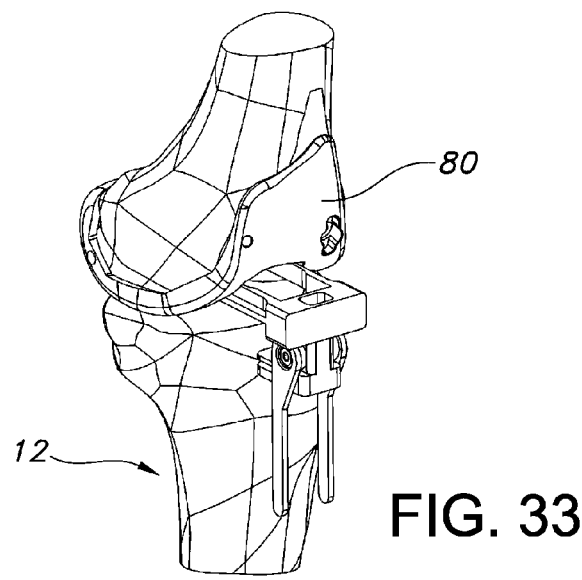
FIG. 33
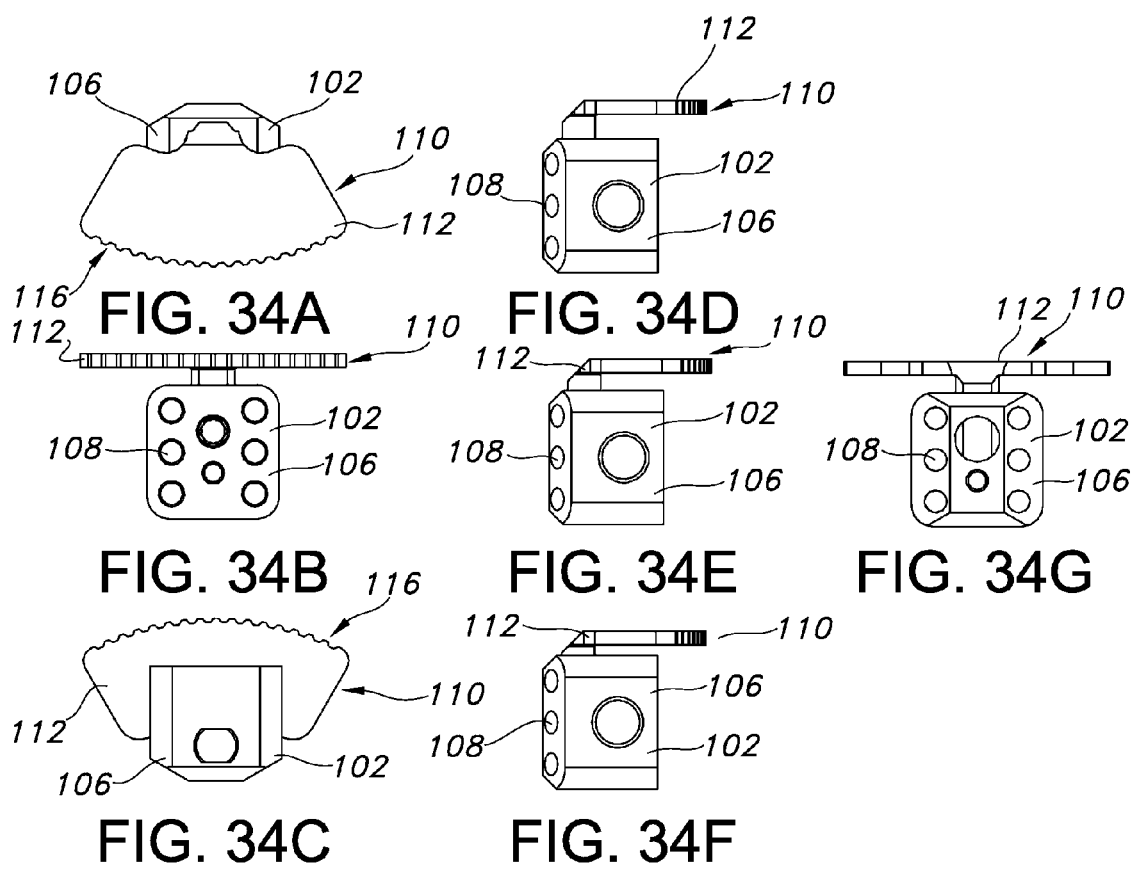
FIG. 34A FIG. 34D FIG. 34G
FIG. 34B FIG. 34E
FIG. 34C FIG. 34F

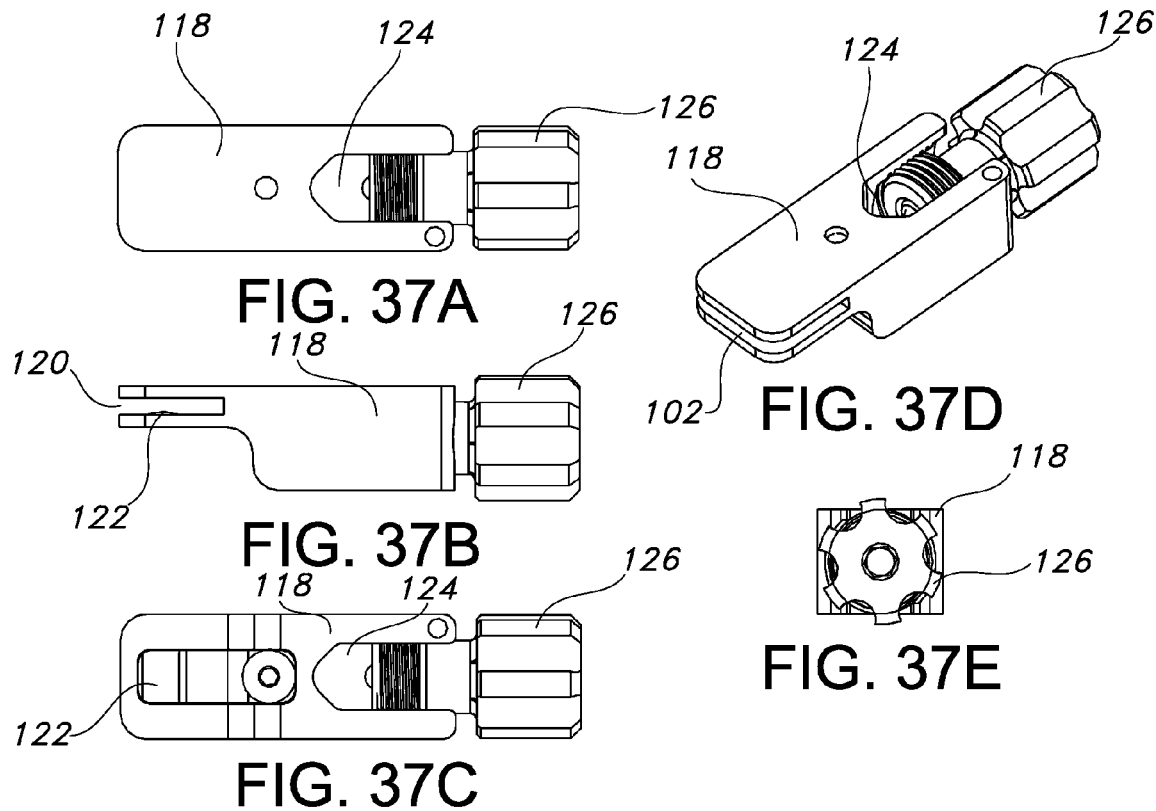
FIG. 37A
FIG. 37B
FIG. 37C
FIG. 37D
FIG. 37E
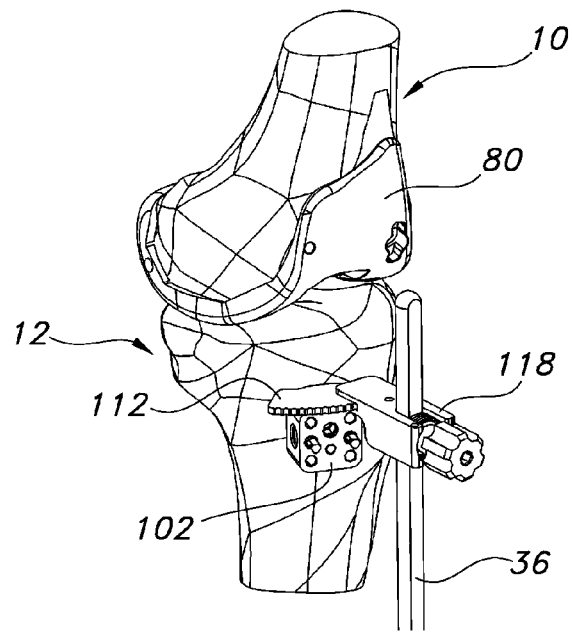
FIG. 38

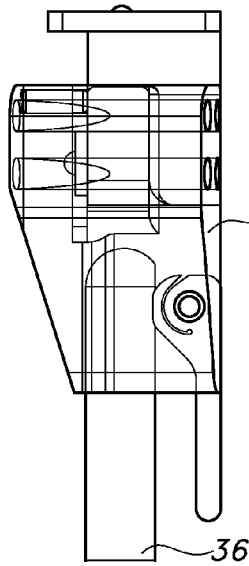
FIG. 39A
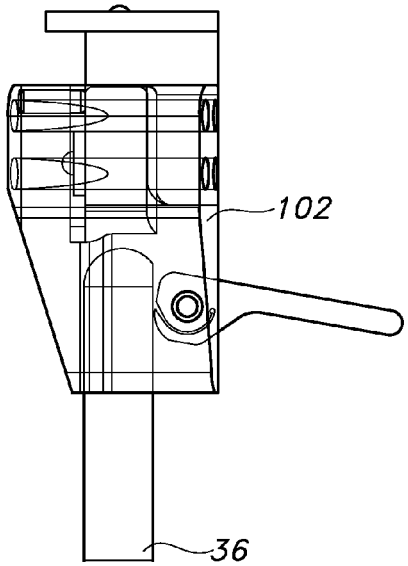
FIG. 39B
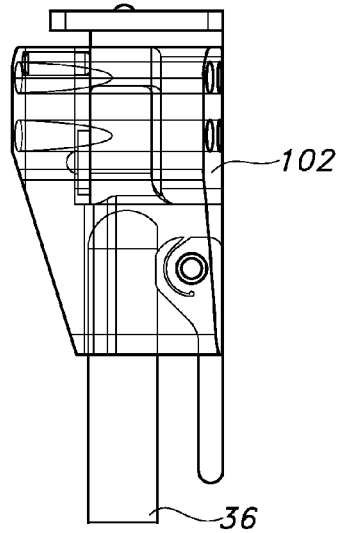
FIG. 39C
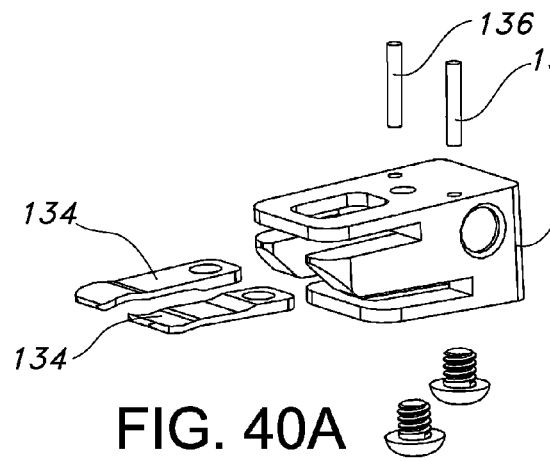
FIG. 40A
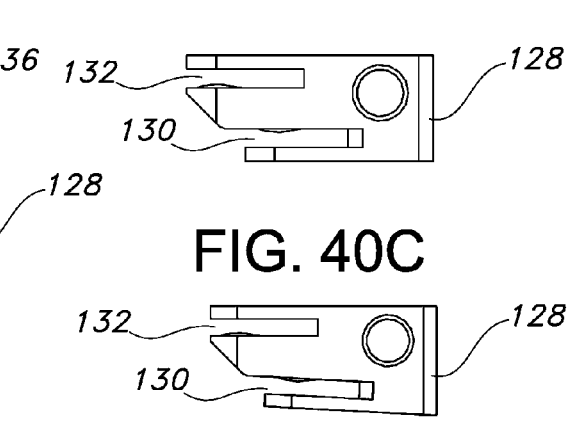
FIG. 40C
FIG. 40D
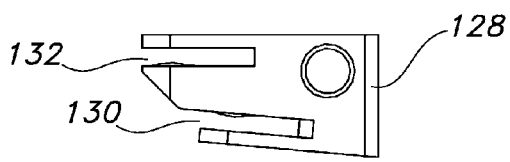
FIG. 40B
FIG. 40E

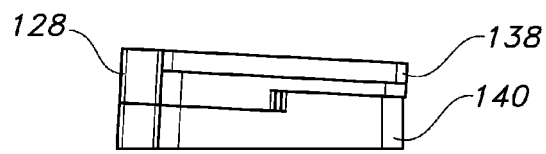
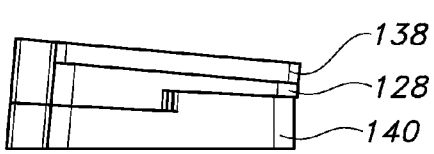
FIG. 41B    FIG. 41C
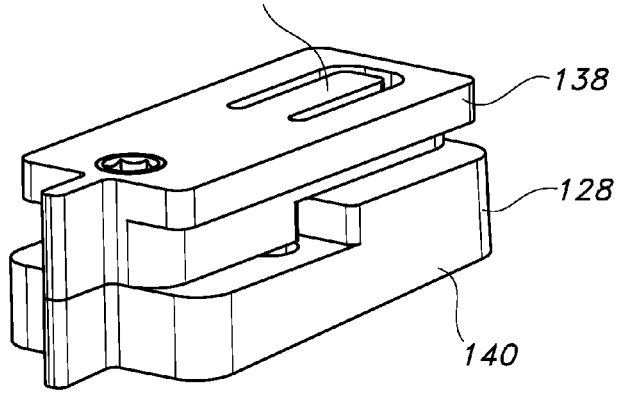
FIG. 41A
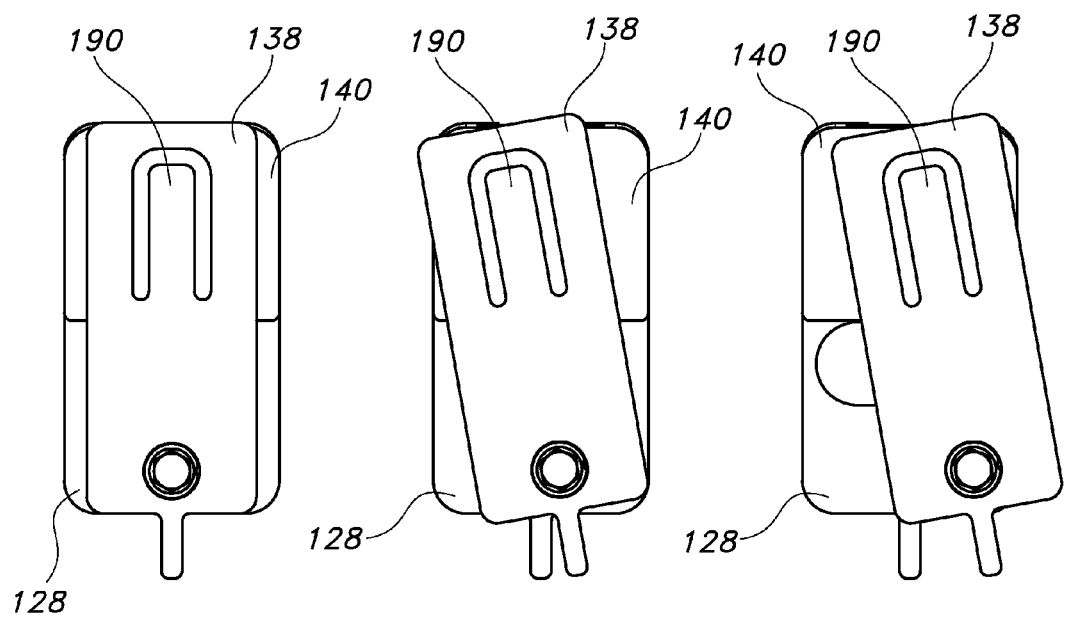
FIG. 42A    FIG. 42B    FIG. 42C

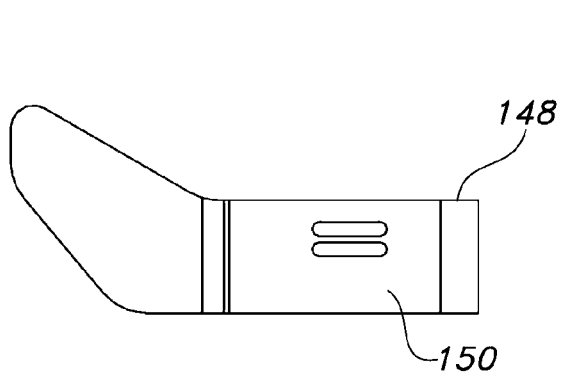
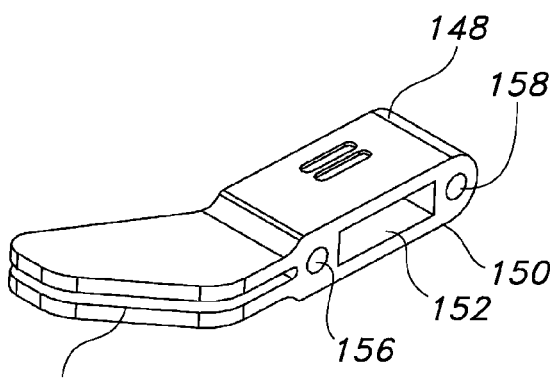
FIG. 45B          FIG. 45A
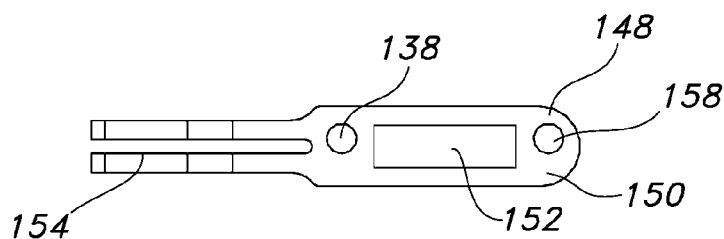
FIG. 45C
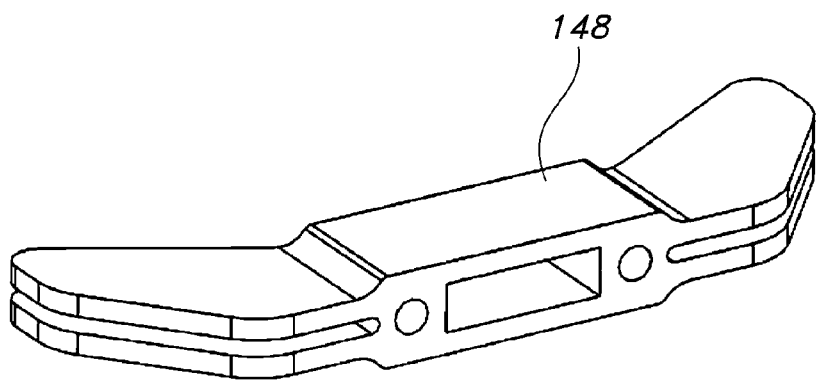
FIG. 46

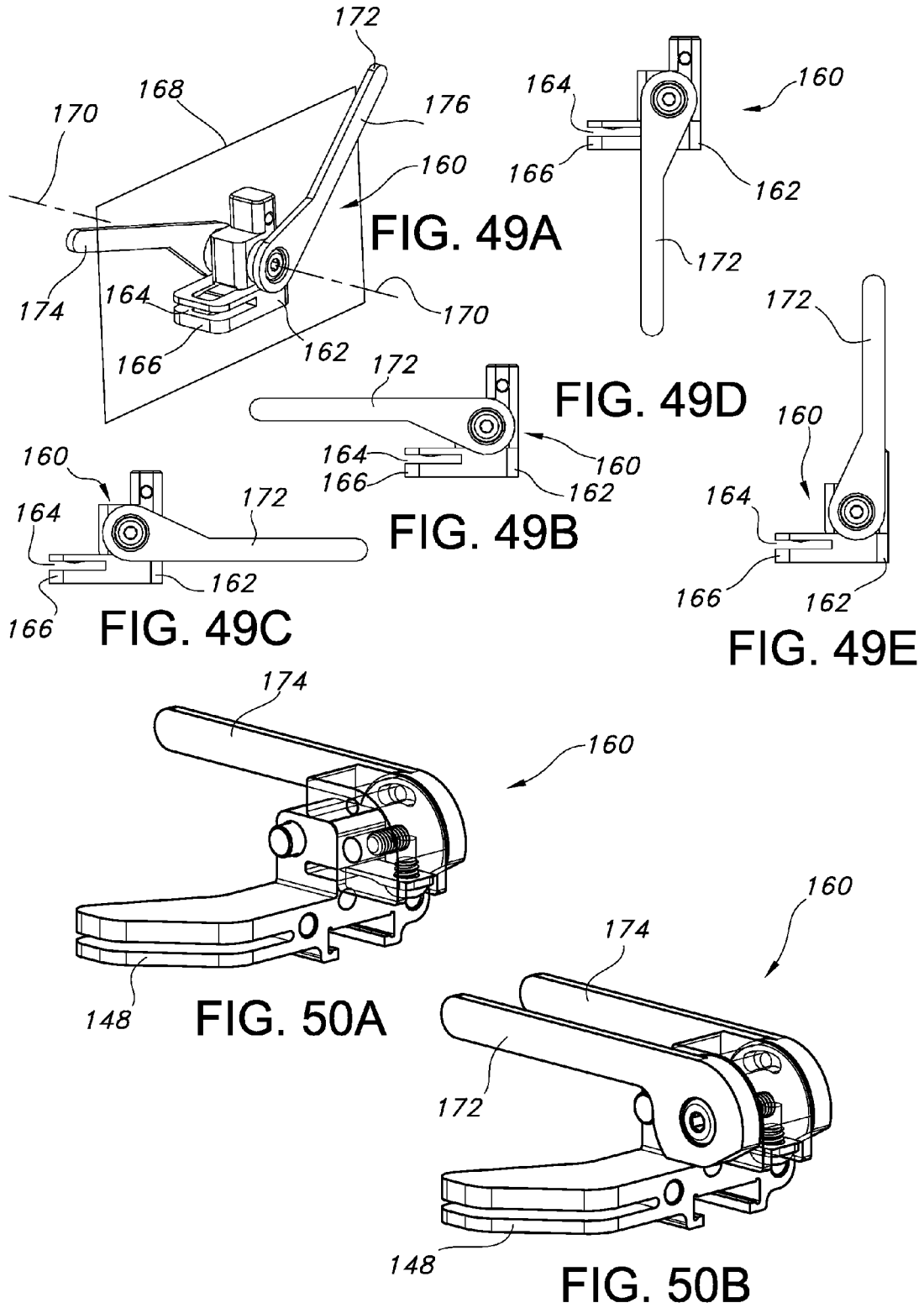

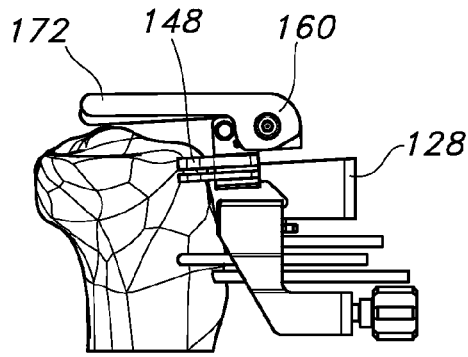
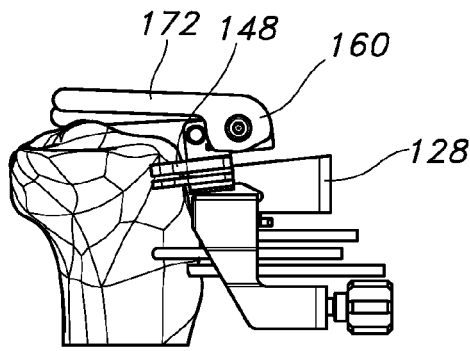
FIG. 61A  FIG. 61B
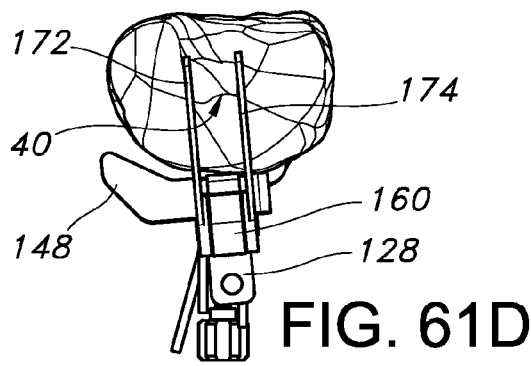
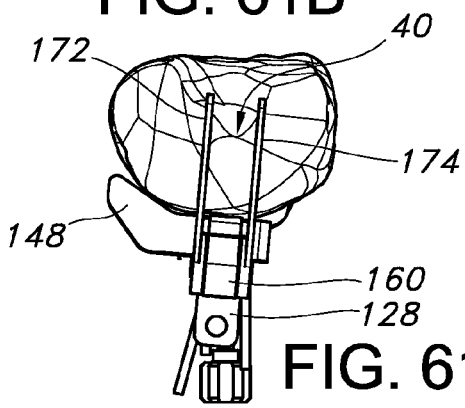
FIG. 61D  FIG. 61C
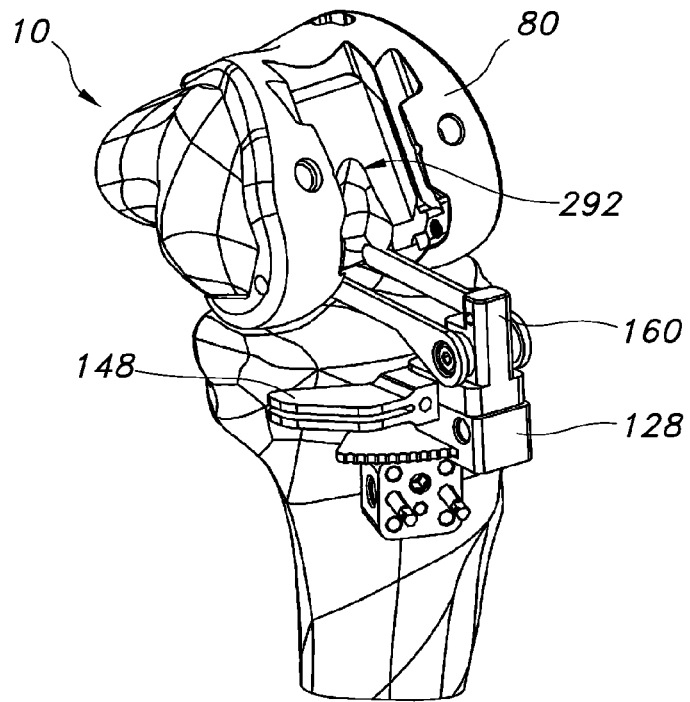
FIG. 62

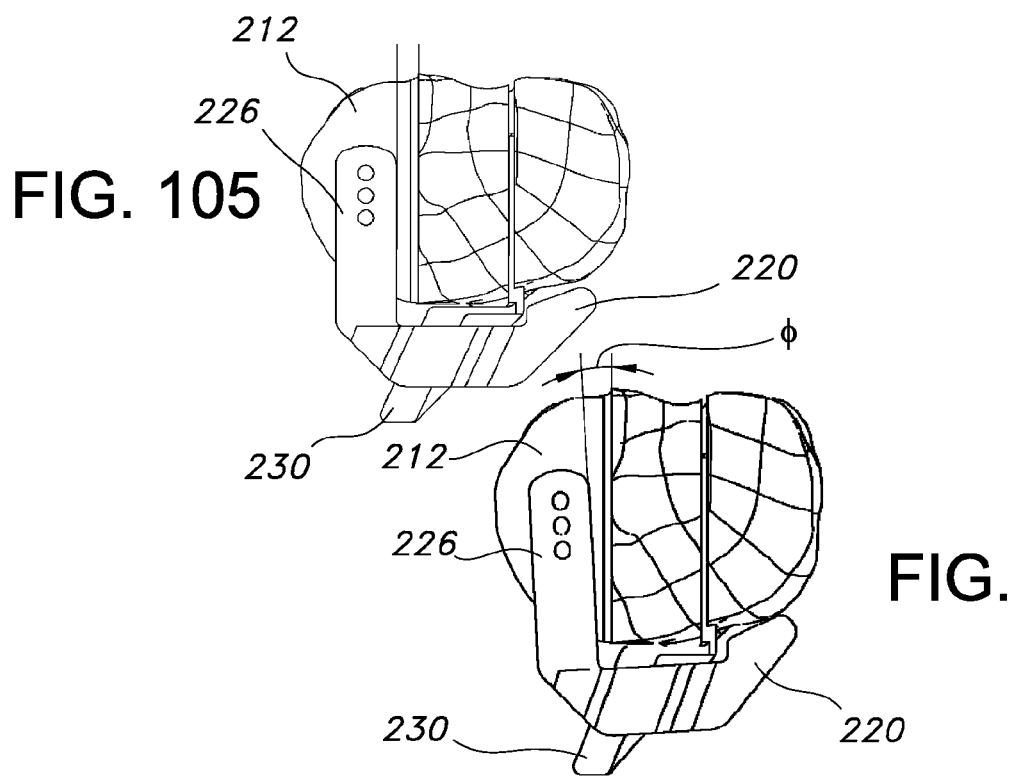
FIG. 105
FIG. 106
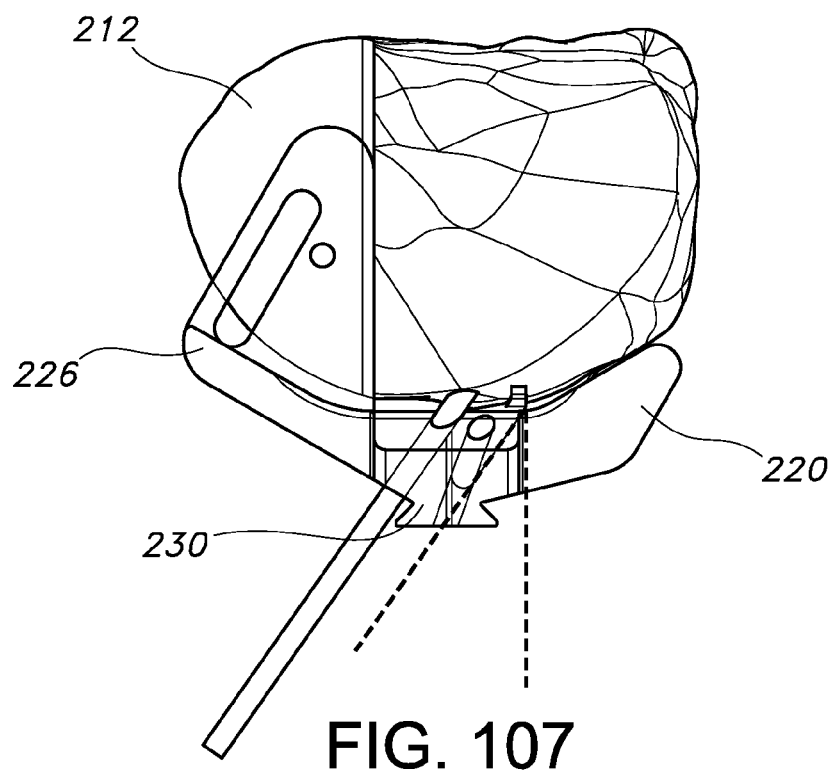
FIG. 107

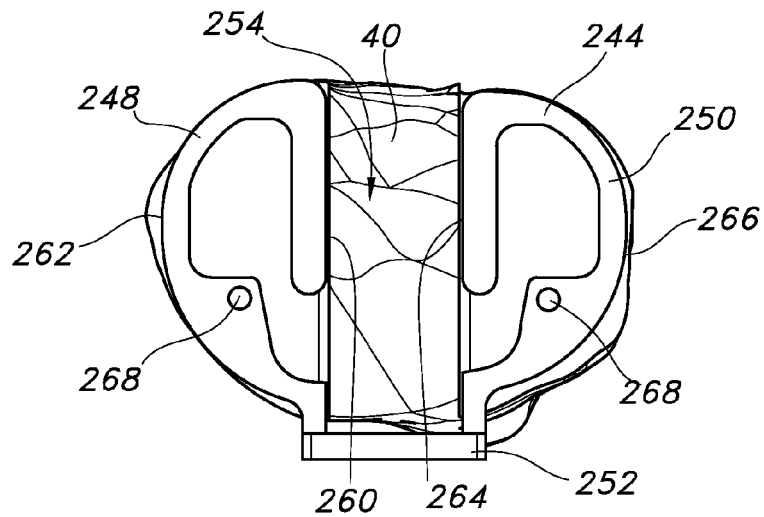
FIG. 108
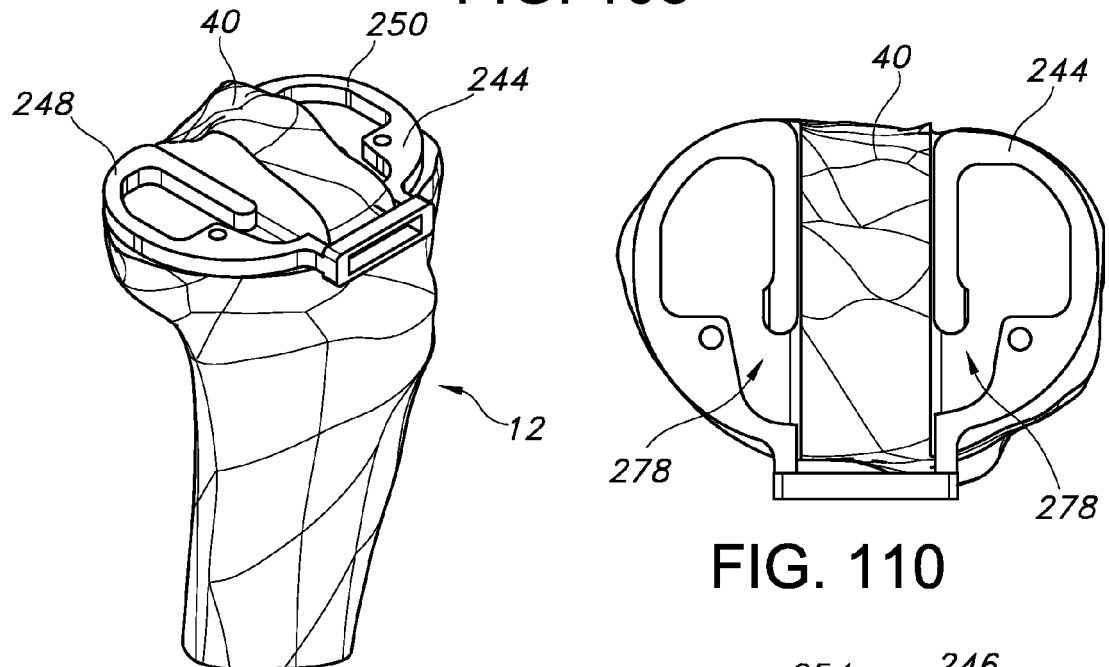
FIG. 109
FIG. 110
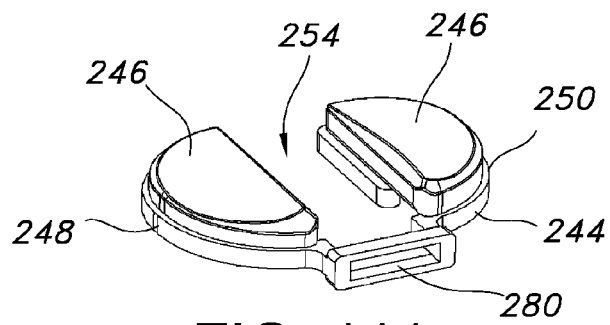
FIG. 111

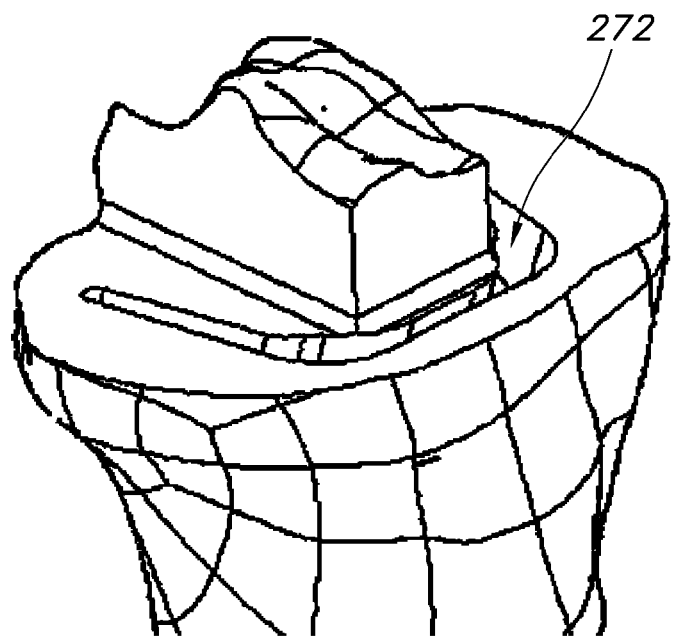
FIG. 140
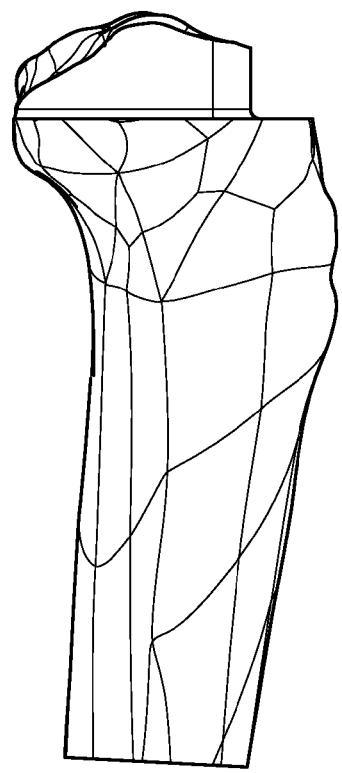 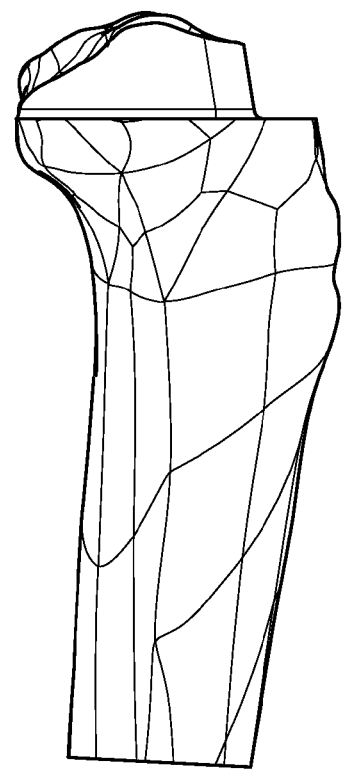
FIG. 141  FIG. 142

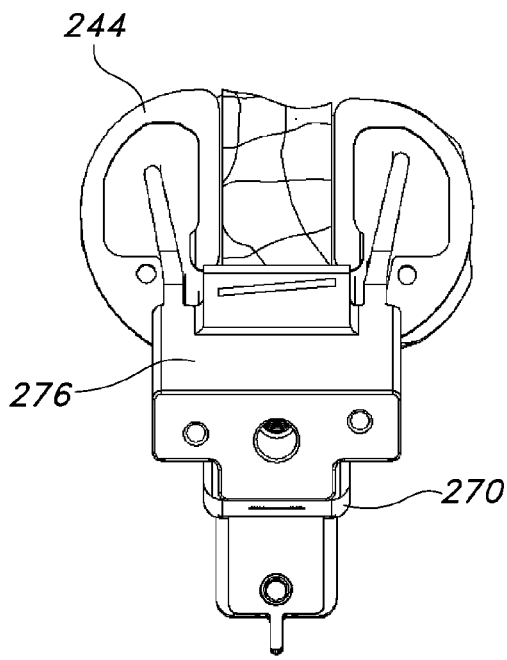
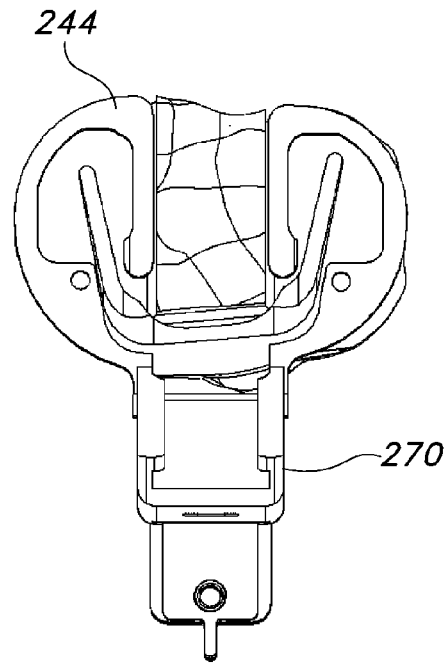
FIG. 147    FIG. 148
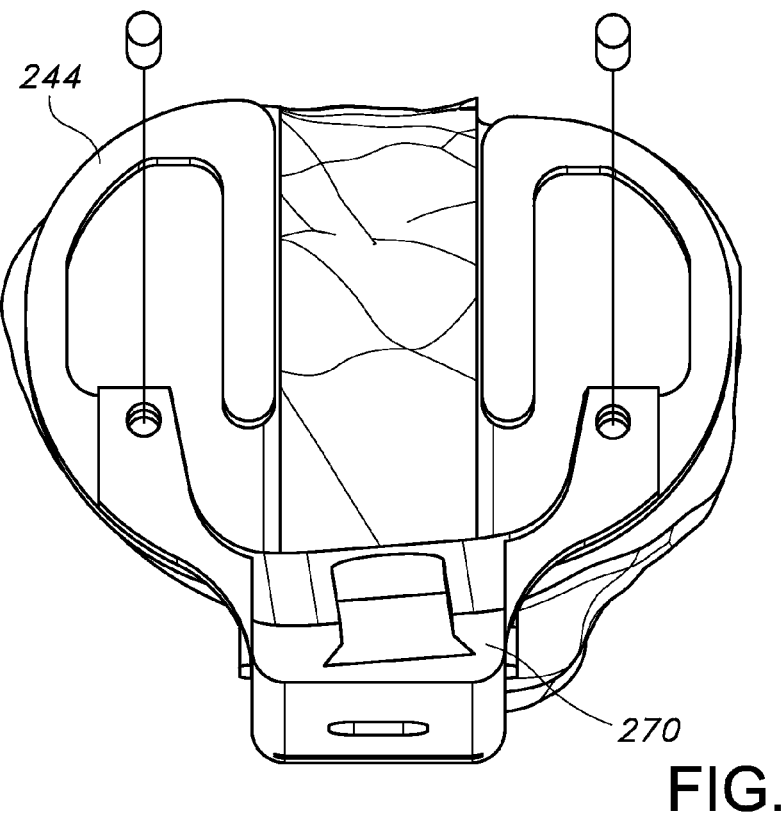
FIG. 149

METHODS AND APPARATUS FOR PERFORMING KNEE ARTHROPLASTY

CROSS-REFERENCE TO RELATED APPLICATIONS

This patent application claims the benefit of U.S. Provisional Patent Application Ser. No. 61/182,435, filed May 29, 2009 for "Methods and Apparatus for Performing Bicruciate Retaining Arthroplasty," and also claims the benefit of U.S. Provisional Patent Application Ser. No. 61/299,835, filed Jan. 29, 2010 for a "Bi-Cruciate Retaining Tibial Implant," the entire contents of both of which are hereby incorporated by this reference.

BACKGROUND

Total knee arthroplasty procedures often require the sacrifice of the anterior cruciate ligament (ACL) and the posterior cruciate ligament (PCL). As such, total knee prostheses often include structures and mechanisms that attempt to provide the same or similar functions of the ACL and PCL. Some believe, however, that these conventional total knee prostheses do not fully replicate the normal proprioception, kinematics, and biomechanical function that natural ligaments provide for all patients. Bicruciate retaining knee replacements have been used in the past, but were associated with problems of knee stiffness and implant failure which were likely related to inadequate implant design, instrumentation, and/or implantation technique. Accordingly, there is a desire in some cases to preserve functioning cruciate ligaments in young and active patients who require knee joint replacement, to maintain a natural feeling, and normal biomechanical function and performance of the knee after knee replacement. There is also a need in some cases for more efficient and accurate methods and apparatus for preparing femurs and tibias for bicruciate retaining implants (i.e., ACL and PCL preserving) as well as other types of knee implants, since many knee procedures (especially, but not limited to, bicruciate retaining procedures) often employ methods and apparatus that are less than ideal.

SUMMARY

Methods and apparatus for performing knee arthroplasty procedures, including methods and apparatus useful to total knee arthroplasty (TKA) procedures such as bicruciate retaining arthroplasty and others are described herein.

In some embodiments, there is provided a surgical kit for arthroplasty on a knee joint, the surgical kit comprising at least one distal femoral trial for evaluating a distal femoral resection of a distal femur, wherein the distal femoral trial comprises a top most, superior, planar surface for contact with the distal femoral resection; and an inferior, curved surface defining at least one condylar surface for contact with an unresected surface on a proximal tibia. In some embodiments, the inferior, curved surface defines a medial and lateral condylar surfaces for contact with the unresected surface on the proximal tibia. In some embodiments, the distal femoral trial is a gauge for gauging internal/external rotation, anterior/posterior position, medial/lateral position, or size of the distal femoral trial with respect to the distal femur. In some embodiments, the distal femoral trial includes one or more references located on the distal femoral trial to indicate an expected position and orientation of a femoral implant with respect to the distal femur. In some embodiments, the references are located to indicate a position of the distal femoral trial with respect to posterior medial and posterior lateral edges of the distal femoral resection. In some embodiments, the one or more references for indicating the position of the distal femoral trial with respect to posterior medial and posterior lateral edges of the distal femoral resection comprise posterior edges of the inferior, curved surface of the distal femoral trial. In some embodiments, the distal femoral trial includes one or more references for indicating a position of the distal femoral trial with respect to a central anterior V point of the distal femoral resection. In some embodiments, the one or more references for indicating the position of the distal femoral trial with respect to the central anterior V point of the distal femoral resection comprise one or more windows extending through the distal femoral trial. In some embodiments, the distal femoral trial comprises a bicruciate retaining distal femoral trial. In some embodiments, the distal femoral trial is substantially U-shaped and defines a gap between the medial and lateral condylar surfaces for receiving at least a portion of a tibial eminence on a proximal tibia. In some embodiments, the distal femoral trial substantially replicates at least one of a shape, a thickness, and a size of an inferior portion of a bicruciate retaining femoral implant. In some embodiments, the distal femoral trial is part of a set of distal femoral trials of different sizes of distal femoral trials. In some embodiments, the different sizes of distal femoral trials substantially replicate distal portions of different sizes of femoral implants. In some embodiments, the distal femoral trial is modular. In some embodiments, the surgical kit comprises a plurality of shims for varying a thickness of the distal femoral trial. In some embodiments, the surgical kit comprises a plurality of shims for varying a thickness of a lateral condylar portion of the distal femoral trial. In some embodiments, the surgical kit comprises a plurality of shims for varying at least one of a varus/valgus angle and a flexion/extension angle. In some embodiments, the distal femoral trial is part of a set of distal femoral trials of different thicknesses. In some embodiments, the distal femoral trial is part of a set of distal femoral trials of having different varus/valgus angles or different flexion/extension angles. In some embodiments, the surgical kit also includes an alignment block for securement to the proximal tibia, wherein the alignment block is connectable to the distal femoral trial. In some embodiments, the alignment block is connectable to the distal femoral trial in a fixed angular position. In some embodiments, the surgical kit also includes an alignment block for securement to the proximal tibia; wherein the distal femoral trial includes an attachment site for connecting the alignment block to the distal femoral trial. In some embodiments, the surgical kit also includes a connector for connecting the alignment block to the distal femoral trial in a fixed angular orientation. In some embodiments, the surgical kit also includes a connector for connecting the alignment block to the distal femoral trial such that a planar bench of the alignment block is parallel to the proximal, planar surface of the distal femoral trial. In some embodiments, the surgical kit also includes an indicator for indicating at least one aspect of a proximal tibial resection; wherein the distal femoral trial includes an attachment site for associating the indicator with the distal femoral trial. In some embodiments, the indicator is for indicating a posterior slope of the proximal tibial resection, a varus/valgus angle of the proximal tibial resection, or a depth of the proximal tibial resection.

In some embodiments, there is provided a method of performing an arthroplasty on a knee joint having a distal femur and a proximal tibia, the method comprising performing at least one planar distal femoral resection on the distal femur to create at least one resected surface on the distal femur; inserting a trial between the resected surface on the distal femur and an unresected surface on the proximal tibia, wherein the trial contacts the resected surface on the distal femur and the unresected surface on the proximal tibia; and evaluating the distal femoral resection using the trial. In some embodiments, evaluating the distal femoral resection using the trial occurs prior to performing at least one additional box cut on the distal femur. In some embodiments, performing the at least one distal femoral resection comprises performing the at least one distal femoral resection prior to performing a proximal tibia resection. In some embodiments, performing the at least one distal femoral resection prior to performing the proximal tibia resection comprises performing the at least one distal femoral resection prior to performing any proximal tibia resections on the proximal tibia. In some embodiments, inserting the trial comprises inserting a distal femoral trial having a superior, planar surface for contact with the at least one distal femoral resection and an inferior, curved surface for contact with the unresected surface on the proximal tibia. In some embodiments, inserting the distal femoral trial comprises inserting a distal femoral trial having a superior, planar surface and an inferior, curved surface that replicates a shape and a thickness of a femoral implant for installation on the distal femur. In some embodiments, the method also includes performing at least one additional femoral resection after evaluating the distal femoral resection using the distal femoral trial. In some embodiments, performing the at least one distal femoral resection comprises performing the at least one distal femoral resection to a depth that is approximately equal to a distal thickness of the femoral implant for implantation on the distal femur. In some embodiments, the method also includes re-cutting the at least one distal femoral resection after evaluating the distal femoral resection using the distal femoral trial. In some embodiments, evaluating the distal femoral resection using the distal femoral trial comprises evaluating the knee joint for flexion contracture. In some embodiments, evaluating the knee joint for flexion contracture comprises extending the knee joint and assessing terminal extension. In some embodiments, the method also includes inserting a second trial between the resected surface on the distal femur and the unresected surface on the proximal tibia, wherein the second trial contacts the resected surface on the distal femur and the unresected surface on the proximal tibia; and re-evaluating the distal femoral resection using the second trial. In some embodiments, the method of performing the arthroplasty is a method of performing a bicruciate retaining arthroplasty. In some embodiments, the method also includes, after evaluating the distal femoral resection using the distal femoral trial, switching from the method of performing the bicruciate retaining arthroplasty to a method of performing a posterior cruciate retaining arthroplasty or a method of performing a bicruciate sacrificing arthroplasty. In some embodiments, the method also includes using the trial to position an alignment block or indicia with respect to the proximal tibia. In some embodiments, using the trial to position the alignment block or indicia with respect to the proximal tibia comprises: connecting the alignment block to the trial; and securing the alignment block to the proximal tibia. In some embodiments, the method also includes connecting the alignment block to the trial using an intermediate connector. In some embodiments, the method also includes using the trial to position the alignment block in a desired varus/valgus angle. In some embodiments, the method also includes using the trial to position the alignment block in a desired posterior slope angle. In some embodiments, the method also includes using the alignment block to guide at least one tibial resection after securing the alignment block to the proximal tibia.

In some embodiments, there is provided a femoral cutting assembly for cutting a distal sulcus portion of a distal femur, the femoral cutting assembly comprising a notched cutter extending along a longitudinal axis, the notched cutter comprising a leading cutting edge having a medial portion, a lateral portion, and a central portion between the medial and lateral portion, wherein the central portion is substantially recessed into the notched cutter along the longitudinal axis with respect to the medial and lateral portions; and a femoral cutting guide for positioning and guiding the movement of the notched cutter along the longitudinal axis. In some embodiments, the femoral cutting guide comprises a femoral trial component. In some embodiments, the femoral cutting guide further comprises a modular cutting guide secured in the femoral trial component. In some embodiments, the leading cutting edge is a U-shaped leading cutting edge or a V-shaped leading cutting edge. In some embodiments, the notched cutter further comprises at least a pair of flanges extending substantially parallel to the longitudinal axis. In some embodiments, the femoral cutting assembly also includes a stop on at least one of the notched cutter and femoral cutting guide, the stop positioned to limit the movement of the notched cutter along the longitudinal axis.

In some embodiments, there is provided an assembly for conducting arthroplasty on a knee joint, the assembly comprising a fundamental instrument configured to be secured with respect to a proximal tibia of the knee joint, the fundamental instrument including a bench having a bench connector configured to be oriented at a neutral anterior/posterior slope and a neutral varus/valgus angle relative to the proximal tibia when secured with respect to the proximal tibia; and an adjustment instrument configured to be coupled to the fundamental instrument, the adjustment instrument comprising: a receiver structure configured to connect to the bench connector of the fundamental instrument in a manner that permits at least one of an angular adjustment of the adjustment instrument relative to the fundamental instrument in internal/external rotation and a translational adjustment of the adjustment instrument relative of the fundamental instrument in medial/lateral position, the receiver structure including an alignment axis; a cutting guide connector oriented at a predetermined slope angle relative to the receiver structure alignment axis, the cutting guide connector configured to connect to a cutting guide; whereby the assembly is configured to permit orientation of the cutting guide connector relative to the proximal tibia in at least medial/lateral translation or at least one of the following angulations when the adjustment instrument is connected to the fundamental instrument: neutral varus/valgus; predetermined slope; desired internal/external rotation. In some embodiments, the adjustment instrument includes structure for adjustably orienting and fixing slope angle of the cutting guide connector relative to the receiver structure alignment axis. In some embodiments, the adjustment instrument includes structure for adjustably orienting and fixing internal/external rotation of the cutting guide connector relative to the receiver structure alignment axis. In some embodiments, adjustment instrument includes structure for adjustably orienting and fixing medial/lateral position of the cutting guide connector relative to the receiver structure alignment axis. In some embodiments, the cutting guide connector includes at least one rail for connection to the cutting guide, the rail configured to align in at least one of the following angulations relative to the tibia of the patient: predetermined neutral varus/valgus; predetermined slope angle; desired medial/lateral translation; and desired internal/external rotation. In some embodiments, the assembly is configured to permit simultaneous adjustment of the adjustment instrument on the fundamental instrument in medial/lateral translation, anterior/posterior translation, and internal/external rotation. In some embodiments, the adjustment instrument is one of a set of adjustment instruments, at least some of the adjustment instruments having different predetermined slope angles.

In some embodiments, there is provided an alignment block for conducting arthroplasty on a knee joint, comprising: a body configured to be secured to an anterior surface on a tibia proximate to a tubercle of the tibia; an extramedullary rod connector coupled to the body, the extramedullary rod connector configured to be releasably fixed to an extramedullary rod that is aligned with an anatomical axis of the tibia in a sagittal plane of the tibia, without the body being aligned with the anatomical axis of the tibia in the sagittal plane; (c) a bench connected to a superior portion of the body, the bench being generally planar in shape to define a bench connector that is substantially perpendicular to a longitudinal axis of the extramedullary rod when the extramedullary rod is fixed to the extramedullary rod connector, the bench connector configured to be oriented at a neutral posterior slope and a neutral varus/valgus angle relative to the proximal tibia when the body is secured to the tibia and the extramedullary rod connector is fixed to the extramedullary rod that is aligned with the anatomical axis of the proximal tibia in the sagittal plane. In some embodiments, the bench is adjustably connected to the body in a manner that permits the bench connector to be adjusted and releasably fixed in a superior or inferior direction relative to the proximal tibia. In some embodiments, the extramedullary rod connector is configured to be adjustably and releasably fixed to the body. In some embodiments, the extramedullary rod connector is configured to be coupled to the bench. In some embodiments, the extramedullary rod connector is configured to be coupled to an inferior portion of the body. In some embodiments, the bench connector includes a plurality of index features configured to permit replicatable coupling of other structures to the bench connector. In some embodiments, the body further comprises openings configured to permit at least two pins to be placed in the tibia in a manner that permits the pins, when so placed, to store information about neutral posterior slope and neutral varus/valgus angle relative to the tibia.

In some embodiments, there is provided a cutting guide assembly for conducting arthroplasty on a knee joint, comprising: a navigation instrument configured to be directly or indirectly connected to a proximal tibia, the navigation instrument including a cutting guide connector that can be oriented in at least the following angulations relative to the proximal tibia: neutral varus/valgus; predetermined anterior/posterior slope; desired medial/lateral translation; and desired internal/external rotation; and a medial tibial resection cutting guide, comprising: a support connection configured to connect the medial tibial resection cutting guide to the cutting guide connector of the navigation instrument; a medial cutting guide surface configured to guide a cutting or milling instrument to remove a medial portion of the proximal tibia, the medial cutting guide surface oriented on the medial tibial resection cutting guide in substantially the same angulations as the cutting guide connector of the navigation instrument; and a medial resection opening and a lateral resection opening, the openings oriented in the medial tibial resection cutting guide in substantially the same angulations as the cutting guide connector of the navigation instrument, each opening configured to guide formation of a bore in the proximal tibia. In some embodiments, the support connection is configured to connect to the cutting guide connector of the navigation instrument in a manner that permits slidable adjustment of the medial tibial resection cutting guide relative to the navigation instrument, and that permits releasable fixation of the medial tibial resection cutting guide relative to the navigation instrument at a desired adjustment. In some embodiments, the medial and lateral resection openings substantially define a width and an internal/external angulation of an eminence on the proximal tibia to which eminence at least one ligament is attached.

In some embodiments, there is provided a stylus for conducting arthroplasty on a knee joint, the stylus comprising: a body configured to connect to instrumentation, the instrumentation configured to connect to at least one of a proximal tibia or a distal femur, the body defining a reference plane and a connection axis that is perpendicular to the reference plane; a first indicator member that is pivotally mounted to the body, the first indicator member configured to rotate about the connection axis in a plane that is substantially parallel to the reference plane of the stylus body; a second indicator member that is pivotally mounted to the body, the second indicator member configured to rotate about the connection axis in a plane that is substantially parallel to the reference plane of the stylus body; a stylus connector connected to the body, the stylus connector configured to locate the reference plane of the stylus in a predetermined position and orientation relative to the instrumentation. In some embodiments, at least one of the indicator members is rotatable to a position that indicates orientation of the instrumentation relative to the proximal tibia in at least internal/external rotation. In some embodiments, at least one of the indicator members is rotatable to a position that indicates orientation of the instrumentation relative to the proximal tibia and distal femur in at least varus/valgus angulation. In some embodiments, at least one of the indicator members includes a guide surface for guiding instrumentation to cut or mill a portion of the proximal tibia proximate an eminence on the proximal tibia, to which eminence at least one ligament is attached. In some embodiments, the indicator members are configured to generally indicate the position, width and angular orientation of an eminence to be formed on the proximal tibia, to which eminence at least one ligament is attached. In some embodiments, at least one of the indicator members is configured to generally indicate alignment of the proximal tibia relative to the distal femur. In some embodiments, the stylus is configured to connect to a cutting guide. In some embodiments, the stylus is configured to connect to instrumentation other than a cutting guide. In some embodiments, the stylus is configured to connect to instrumentation that is connected to the distal femur. In some embodiments, the stylus is configured to connect to instrumentation that is connected to the proximal tibia and instrumentation that is connected to the distal femur. In some embodiments, the stylus is configured to connect to instrumentation that is connected to the proximal tibia of the patient.

In some embodiments, there is provided a stylus for conducting arthroplasty on a knee joint, the stylus comprising: a body, the body including a stylus connector configured to connect to a navigation connector on instrumentation that is configured to be connected to a proximal tibia, the navigation connector on the instrumentation configured to be oriented relative to the proximal tibia in at least the following angulations when the instrumentation is connected to the proximal tibia: neutral varus/valgus angulation; predetermined posterior slope; and desired internal/external rotation; the body defining a reference plane and a connection axis that is perpendicular to the reference plane, the reference plane in alignment with at least the desired internal/external angulation of the navigation connector of the instrumentation when the body is connected to the instrumentation; a first indicator member that is pivotally mounted to the body, the first indicator member configured to rotate about the connection axis in a plane that is substantially parallel to the reference plane of the stylus body; a second indicator member that is pivotally mounted to the body, the second indicator member configured to rotate about the connection axis in a plane that is substantially parallel to the reference plane of the stylus body; whereby at least one indicator member is movable to a position that indicates orientation of the instrumentation relative to the proximal tibia in at least one of internal/external rotation and medial/lateral translation. In some embodiments, the stylus includes a stylus connector that is configured to connect to a cutting guide. In some embodiments, the stylus includes a stylus connector that is configured to connect to instrumentation other than a cutting guide. In some embodiments, the stylus is further configured to connect to instrumentation that is connected to a distal femur. In some embodiments, the stylus is further configured to connect to instrumentation that is connected to an extramedullary rod that is connected to the patient.

In some embodiments, wherein at least one of the indicator members is rotatable to a position that indicates orientation of the instrumentation relative to a knee of the patient in at least varus/valgus angulation. In some embodiments, wherein at least one of the indicator members includes a guide surface for guiding instrumentation to cut or mill a portion of the proximal tibia adjacent an eminence, to which eminence at least one ligament is attached. In some embodiments, the guide surface is configured to prevent cutting or milling of the eminence and the at least one ligament. In some embodiments, the indicator members are configured to generally indicate the position, width and angular orientation of an eminence to be formed on the proximal tibia, to which eminence at least one ligament is attached. In some embodiments, at least one indicator member is configured to generally indicate alignment of the proximal tibia relative to a distal femur.

In some embodiments, there is provided a method for conducting arthroplasty on a knee joint, the knee joint including a distal femur and a proximal tibia, the method comprising: positioning a stylus with respect to the knee joint, the stylus comprising: a body defining a reference plane and a connection axis that is perpendicular to the reference plane; a first indicator member pivotally mounted to the body, the first indicator member configured to rotate about the connection axis in a plane that is substantially parallel to the reference plane of the stylus body; and a second indicator member pivotally mounted to the body, the second indicator member configured to rotate about the connection axes in a plane that is substantially parallel to the reference plane of the stylus body; and using the stylus to assess alignment. In some embodiments, using the stylus to assess alignment comprises using the stylus to assess alignment of the distal femur with respect to the proximal tibia. In some embodiments, using the stylus to assess alignment of the distal femur with respect to the proximal tibia comprises using the stylus to assess alignment of a femoral trial with respect to the proximal tibia. In some embodiments, positioning the stylus with respect to the knee joint comprises connecting the stylus to an instrument secured to the proximal tibia; and wherein the method further comprises positioning at least one of the first and second indicator members proximate the femoral trial. In some embodiments, positioning at least one of the first and second indicator members proximate the femoral trial comprises positioning at least one of the first and second indicator members proximate an intracondylar notch or an anterior trochlear groove on the femoral trial. In some embodiments, positioning one of the first and second indicator members proximate a tubercle on the proximal tibia. In some embodiments, using the stylus to assess alignment comprises connecting at least one of the first and second indicator members to a femoral trial on the distal femur and using the stylus connected to the femoral trial to align an instrument associated with the proximal tibia. In some embodiments, using the stylus connected to the femoral trial comprises using the stylus connected to the femoral trial to align a tibial resection guide associated with the proximal tibia. In some embodiments, using the stylus to assess alignment comprises using the stylus to assess alignment of a tibial resection guide with respect to an eminence on the proximal tibia. In some embodiments, the method also includes positioning the first indicator member on a medial side of the eminence; and positioning the second indicator member on a lateral side of the eminence. In some embodiments, the method also includes using the stylus to guide at least one vertical resection into the proximal tibia.

In some embodiments, there is provided a lateral resection cutting guide for conducting knee surgery, the lateral resection cutting guide comprising: a lateral resection cutting guide body; a paddle connected to the lateral resection cutting guide body, the paddle including a substantially planar surface that is configured to be positioned on a substantially planar medial resection that has been formed on a tibia; and a lateral resection cutting guide member connected to the lateral resection cutting guide body, the lateral resection cutting guide member having a substantially planar lateral resection cutting guide surface, the lateral resection cutting guide surface configured to guide a cutting or milling instrument to form a lateral resection in the tibia that is referenced from the medial resection. In some embodiments, the lateral resection cutting guide surface is configured to guide the cutting or milling instrument such that the lateral resection in the tibia is co-planar with the medial resection in the tibia. In some embodiments, the lateral resection cutting guide body includes a flag pin receiving opening, the flag pin receiving opening configured to receive a flag pin inserted into a lateral resection navigation opening formed in the tibia, the navigation resection opening oriented with respect to the tibia at a predetermined anterior/posterior slope, a desired internal/external rotation, and a desired medial/lateral position; wherein the flag pin receiving opening lies in a plane that is substantially parallel to the substantially planar surface of the paddle. In some embodiments, the flag pin receiving opening includes a planar portion, the planar portion oriented in a plane that is generally parallel to the substantially planar surface of the paddle, the planar portion configured to cooperate with the flag pin and assist in orienting the lateral resection cutting guide, relative to the flag pin. In some embodiments, the flag pin receiving opening forms a boundary to the lateral resection cutting guide surface and is configured to preclude cutting or milling into an eminence on the tibia to which at least one ligament is attached. In some embodiments, at least a portion of the flag pin receiving opening is configured to be oriented at a predetermined angle relative to a longitudinal axis of the lateral resection navigation opening, and thereby configured to permit the cutting guide to be inserted onto the flag pin at the predetermined angle relative to the longitudinal axis of the lateral resection navigation opening in order to reduce contact with soft tissue on a lateral side of the knee during such insertion.

In some embodiments, there is provided a tibial plateau resection guide, comprising: a cutting block defining a horizontal guide for guiding a tibial plateau resection; and an elongated flag pin for positioning the cutting block with respect to a proximal tibia, the flag pin extending along a longitudinal axis and including an enlarged head portion; wherein the cutting block defines an opening for receiving at least a portion of the enlarged head such that the cutting block cannot rotate about the longitudinal axis of the flag pin when the enlarged head portion is positioned in the opening in the cutting block. In some embodiments, the enlarged head portion of the elongated flag pin is substantially planar, and facilitates translation and rotation of the cutting block with respect to the elongated flag pin in at least one plane. In some embodiments, the at least one substantially planar surface of the flag pin is substantially parallel to a guide surface of the horizontal guide of the cutting block when the enlarged head portion is positioned in the opening in the cutting block. In some embodiments, at least a portion of the flag pin defines a second guide for guiding the tibial plateau resection when the enlarged head portion is positioned in the opening in the cutting block. In some embodiments, the second guide of the flag pin is positioned to limit movement of a cutter in a mesial direction when the enlarged head portion is positioned in the opening in the cutting block. In some embodiments, the second guide of the flag pin is defined by the enlarged head portion and an elongated insertion portion of the flag pin. In some embodiments, portions of the second guide of the flag pin are positioned to prevent movement of a cutter into anterior and mesial aspects of a tibial eminence of the tibial plateau when the enlarged head portion is positioned in the opening in the cutting block. In some embodiments, the cutting block further comprises a reference for referencing a second tibial plateau resection, the reference including an inferior planar reference surface. In some embodiments, the horizontal guide comprises an inferior planar guide surface, and wherein the inferior planar guide surface is substantially coplanar to the inferior planar reference surface. In some embodiments, the horizontal guide is a lateral horizontal guide configured for guiding a lateral resection and wherein the reference comprises a medial reference configured for referencing a medial resection. In some embodiments, the cutting block can rotate about at least a second axis and can translate in at least one direction when the enlarged head portion is positioned in the opening in the cutting block.

In some embodiments, there is provided a kit of tibial trials for use in performing an arthroplasty on a knee joint having a distal femur and a proximal tibia, the kit comprising: a first tibial trial for positioning with respect to the distal femur and a first resected surface on the proximal tibia, the first tibial trial at least partially simulating a first tibial implant implanted on the first resected surface of the proximal tibia; and a second tibial trial for positioning with respect to the distal femur and the first resected surface on the proximal tibia, the second tibial trial at least partially simulating the first tibial implant implanted on a second resected surface of the proximal tibia. In some embodiments, the first tibial trial is thicker than the second tibial trial and the first tibial trial has a different posterior slope than the second tibial trial. In some embodiments, the first tibial trial is thicker than the second tibial trial or the first tibial trial has a different posterior slope than the second tibial trial. In some embodiments, the second tibial trial simulates a recut of the proximal tibia, the recut defining the second resected surface, wherein the second resected surface is distal to the first resected surface. In some embodiments, the second tibial trial simulates a recut of the proximal tibia, the recut defining the second resected surface, wherein the second resected surface has a posterior slope that is different from a posterior slope of the first resected surface. In some embodiments, the first tibial trial is for positioning with respect to a femoral trial on the distal femur and the second tibial trial is for positioning with respect to the femoral trial on the distal femur. In some embodiments, the first and second tibial trials each include a proximal articulation surface for articulation with the femoral trial. In some embodiments, the first and second tibial trials each include a medial superior articulation surface for articulation with a medial condyle of the femoral trial. In some embodiments, the kit also includes a handle for connecting to the first and second tibial trials. In some embodiments, the handle includes a planar inferior surface for contacting the resected surface on the proximal tibia. In some embodiments, the first tibial trial includes a superior articular surface for replicating a position and orientation of a superior articular surface of the first tibial implant when implanted on the first resected surface of the proximal tibia. In some embodiments, the second tibial trial includes a superior articular surface for replicating a position and orientation of the superior articular surface of the first tibial implant when implanted on the second resected surface of the proximal tibia. In some embodiments, the kit also includes a third tibial trial that includes a superior articular surface for replicating a position and orientation of a superior articular surface of a second tibial implant when implanted on the first resected surface of the proximal tibia. In some embodiments, the second tibial implant has a different thickness than the first tibial implant. In some embodiments, the second tibial implant has a different posterior slope than the first tibial implant.

In some embodiments, there is provided a method of performing an arthroplasty on a knee joint having a distal femur and a proximal tibia, the method comprising: resecting one of a medial or a lateral portion of the proximal tibia to define a first resected surface; positioning a first tibial trial with respect to the first resected surface and the distal femur; evaluating the first resected surface using the first tibial trial; and after evaluating the first resected surface using the first tibial trial, resecting the other of the medial or lateral portion of the proximal tibia. In some embodiments, evaluating the first resected surface using the first tibial trial comprises articulating the distal femur with respect to the proximal tibia. In some embodiments, evaluating the first resected surface using the first tibial trial comprises articulating a femoral trial with respect to the first tibial trial. In some embodiments, positioning the first tibial trial with respect to the first resected surface and the distal femur comprises positioning the first tibial trial with respect to the first resected surface and the distal femur to simulate a first tibial implant implanted on the proximal tibia. In some embodiments, positioning a second tibial trial with respect to the first resected surface and the distal femur before resecting the other of the medial or lateral portions of the proximal tibia. In some embodiments, positioning the second tibial trial with respect to the first resected surface comprises simulating a re-cut of the one of the medial or lateral portions of the proximal tibia to define a second resected surface. In some embodiments, the method also includes re-cutting the one of the medial or lateral portions of the proximal tibia to define the second resected surface before resecting the other of the medial or lateral portions of the proximal tibia. In some embodiments, positioning the second tibial trial with respect to the first resected surface comprises simulating a second tibial implant implanted on the proximal tibia. In some embodiments, simulating the second tibial implant comprises simulating a tibial implant having a different thickness than the first tibial implant. In some embodiments, simulating the second tibial implant comprises simulating a tibial implant having a different posterior slope than the first tibial implant.

In some embodiments, there is provided a method of performing an arthroplasty on a knee joint having a distal femur and a proximal tibia, the method comprising: resecting at least one of a medial or a lateral portion of the proximal tibia to define a first resected surface; positioning a first tibial trial with respect to the first resected surface and the distal femur; evaluating the first resected surface using the first tibial trial; positioning a second tibial trial with respect to the first resected surface and the distal femur; and simulating a re-cut of the at least one of the medial or lateral portions of the proximal tibia to define a second resected surface. In some embodiments, evaluating the first resected surface using the first tibial trial comprises articulating the distal femur with respect to the proximal tibia. In some embodiments, evaluating the first resected surface using the first tibial trial comprises articulating a femoral trial with respect to the first tibial trial. In some embodiments, evaluating the first resected surface comprises evaluating the balance of the knee joint in flexion and extension. In some embodiments, simulating the re-cut comprises simulating a re-cut at least one of a different posterior slope or a different resection depth. In some embodiments, positioning the first tibial trial with respect to the first resected surface and the distal femur comprises positioning the first tibial trial with respect to the first resected surface and the distal femur to simulate a first tibial implant implanted on the proximal tibia. In some embodiments, the method also includes, after evaluating the first resected surface using the first tibial trial, resecting the other of the at least one of the medial or lateral portion of the proximal tibia.

In some embodiments, there is provided a reciprocating bone cutting device, comprising: a first reciprocating bone cutting blade; a second reciprocating bone cutting blade; and a connector connecting the first and second reciprocating bone cutting blades together. In some embodiments, the first and second reciprocating bone cutting blades are elongated and each includes a proximal end and a distal end; and the connector connects the first and second reciprocating bone cutting blades together proximate the proximal end of each blade. In some embodiments, the first and second reciprocating bone cutting blades are only connected together proximate the proximal end of each reciprocating bone cutting blade. In some embodiments, the first and second reciprocating bone cutting blades each define a cutting plane, the cutting planes extending substantially parallel to one another. In some embodiments, the first and second reciprocating bone cutting blades are biased towards one another. In some embodiments, each of the first and second reciprocating bone cutting blades include an inner, planar surface. In some embodiments, the inner, planar surfaces of the first and second reciprocating bone cutting blades are substantially smooth. In some embodiments, the first and second reciprocating bone cutting blades are removably connected to the connector. In some embodiments, the connector includes an attachment feature for securing the reciprocating bone cutting device in a reciprocating saw. In some embodiments, each of the first and second reciprocating bone cutting blades includes an attachment feature for securing the reciprocating bone cutting blades in the reciprocating saw. In some embodiments, the attachment features of the reciprocating bone cutting blades are substantially the same size and shape as the attachment feature of the connector. In some embodiments, the first and second reciprocating bone cutting blades are integral with the connector. In some embodiments, the first and second reciprocating bone cutting blades are positioned and oriented with respect to one another to facilitate making two cuts in a proximal tibia at the same time. In some embodiments, the first and second reciprocating bone cutting blades are positioned and oriented with respect to one another to facilitate making two vertical eminence cuts in a proximal tibia at the same time.

In some embodiments, there is provided a bicruciate retaining tibial baseplate, comprising: a medial baseplate web; a lateral baseplate web; and a bridge connecting the medial and lateral baseplate webs; wherein the bicruciate retaining tibial baseplate defines a gap between the medial baseplate web and the lateral baseplate web, the gap being sized and positioned to receive a tibial eminence including an anterior cruciate ligament attachment site and a posterior cruciate ligament attachment site. In some embodiments, the medial and lateral baseplate webs each define substantially planar inferior surfaces for referencing medial and lateral tibial plateau resections respectively; wherein the substantially planar inferior surfaces are substantially co-planar. In some embodiments, the medial baseplate web includes at least one medial attachment site for securing a medial tibial trial insert; wherein the lateral base plate web includes at least one lateral attachment site for securing a lateral tibial trial insert. In some embodiments, the bicruciate retaining tibial baseplate defines a punch gap for receiving a punch including a medial punching surface and a lateral punching surface. In some embodiments, the punch gap is for receiving a substantially U-shaped punch; wherein a first leg of the U-shaped punch includes the medial punching surface and a second leg of the U-shaped punch includes the lateral punching surface. In some embodiments, the baseplate also includes at least one punch guide attachment site for securing a punch guide to the bicruciate retaining tibial baseplate. In some embodiments, the bicruciate retaining tibial baseplate defines an anterior plateau resection gap for receiving a cutter for resecting an anterior aspect of the tibial eminence. In some embodiments, the anterior plateau resection gap is a slot extending through the bridge. In some embodiments, the bicruciate retaining tibial baseplate defines a punch gap for receiving a substantially U-shaped punch including a medial punching surface and a lateral punching surface. In some embodiments, the baseplate also includes at least one guide attachment site for securing a guide for guiding the U-shaped punch and the cutter for resecting the anterior aspect of the tibial eminence.

In some embodiments, there is provided a method of performing a bicruciate retaining arthroplasty on a knee joint having a distal femur and a proximal tibia, the method comprising: resecting medial and lateral portions of the proximal tibia around a tibial eminence to define resected medial and lateral portions of the tibia; positioning a tibial trial on the resected medial and lateral portions of the proximal tibia; and after positioning the tibial trial on the resected medial and lateral portions of the proximal tibia, removing an anterior aspect of the tibial eminence. In some embodiments, the method also includes, before removing the anterior aspect of the tibial eminence, evaluating the resected medial and lateral portions of the proximal tibia using the tibial trial. In some embodiments, evaluating the resected medial and lateral portions of the tibia comprises evaluating a range of motion of the knee joint. In some embodiments, evaluating the range of motion of the knee joint comprises articulating a femoral trial with respect to the tibial trial. In some embodiments, resecting medial and lateral portions of the proximal tibia comprises making a horizontal medial tibial plateau resection and a horizontal lateral tibial plateau resection. In some embodiments, resecting medial and lateral portions of the proximal tibia further comprises making a vertical medial resection and a vertical lateral resection. In some embodiments, the method also includes punching a keel cavity into the proximal tibia. In some embodiments, punching the keel cavity occurs before or after removing the anterior aspect of the tibial eminence. In some embodiments, removing the anterior aspect of the tibial eminence comprises making a horizontal cut and a vertical cut on the anterior aspect of the tibial eminence. In some embodiments, the method also includes securing a guide with respect to the tibial trial. In some embodiments, securing the guide with respect to the tibial trial comprises securing a guide for guiding the steps of punching the keel cavity and making the horizontal cut and the vertical cut on the anterior aspect of the tibial eminence. In some embodiments, positioning the tibial trial on the resected medial and lateral portions of the proximal tibia comprises securing the tibial trial to the proximal tibia. In some embodiments, securing the tibial trial to the proximal tibia comprises pinning the tibial trial to the resected medial and lateral portions of the proximal tibia. In some embodiments, securing the tibial trial to the proximal tibia comprises securing the tibial trial to a component secured to an anterior surface of the proximal tibia.

In some embodiments, there is provided a bicruciate retaining tibial trial baseplate, comprising: a medial baseplate web, wherein the medial baseplate web includes a medial, mesial reference surface for illustrating an extent of a medial, mesial surface of a bicruciate retaining tibial implant, wherein the medial baseplate web includes a medial, outer reference surface for illustrating an extent of a medial, outer surface of the bicruciate retaining tibial implant; a lateral baseplate web, wherein the lateral baseplate web includes a lateral, mesial reference surface for illustrating an extent of a lateral, mesial surface of the bicruciate retaining tibial implant, wherein the lateral baseplate web includes a lateral, outer reference surface for illustrating an extent of a lateral, outer surface of the bicruciate retaining tibial implant ; and a bridge connecting the medial and lateral baseplate webs; wherein the bicruciate retaining tibial trial baseplate defines at least one datum site for recording a final desired position of the bicruciate retaining tibial implant. In some embodiments, the datum site is a pair of apertures for receiving bone pins. In some embodiments, the datum site is an attachment site for a guide. In some embodiments, the datum site is an attachment site for a punch guide. In some embodiments, the datum site is an attachment site for an eminence resecting guide. In some embodiments, the datum site is an attachment site for a punch and eminence resecting guide. In some embodiments, the medial, mesial reference surface is a first portion of an arm defining the medial baseplate web and the medial, outer reference surface is a second portion of the arm defining the medial baseplate web; and wherein the lateral, mesial reference surface is a first portion of an arm defining the lateral baseplate web and the lateral, outer reference surface is a second portion of the arm defining the lateral baseplate web. In some embodiments, the arms defining the medial and lateral baseplate webs are structured to receive medial and lateral tibial trial inserts respectively. In some embodiments, outer surfaces of the arms illustrate an outer shape of the bicruciate retaining tibial implant. In some embodiments, the outer surfaces of the arms illustrate a position of a gap in the bicruciate retaining tibial implant for receiving a tibial eminence having attachment sites for an anterior cruciate ligament and a posterior cruciate ligament.

In some embodiments, there is provided a bone removal tool for creating a keel cavity in a proximal tibia, the bone removal tool comprising: a bone removal instrument for defining the keel cavity in the proximal tibia; and a guide for guiding the movement of the bone removal instrument into the proximal tibia, the guide comprising: at least one substantially planar reference surface for referencing a medial plateau resection and a lateral plateau resection on the proximal tibia; a sloped guide extending at a non-perpendicular angle to the at least one substantially planar reference surface, the sloped guide shaped to interact with the bone removal instrument to guide the bone removal instrument at the non-perpendicular angle into the proximal tibia. In some embodiments, the bone removal instrument includes at least one cutting edge. In some embodiments, the at least one cutting edge has a substantially U-shaped cross section. In some embodiments, the sloped guide extends at an angle that is non-perpendicular to the at least one substantially planar reference surface and at an angle that is obtuse to the at least one substantially planar reference surface. In some embodiments, the sloped guide includes a capture surface for constraining the movement of the bone removal instrument. In some embodiments, the bone removal instrument includes an elongated protrusion; and wherein the capture surface captures the elongated protrusion. In some embodiments, the at least one substantially planar reference surface is an inferior surface of a bicruciate retaining tibial trial baseplate. In some embodiments, the bicruciate retaining tibial trial baseplate defines a gap between a medial baseplate web and a lateral baseplate web, the gap being sized and positioned to receive a tibial eminence including an anterior cruciate ligament attachment site and a posterior cruciate ligament attachment site. In some embodiments, the guide further comprises a horizontal guide positioned and oriented for guiding the movement of a second cutter into an anterior portion of the tibial eminence in a plane that is substantially parallel or co-planar to the inferior surface of the bicruciate retaining tibial trial baseplate. In some embodiments, the guide further comprises a vertical guide positioned and oriented for guiding the movement of a second cutter into an anterior portion of the tibial eminence in a plane that is not substantially parallel to the inferior surface of the bicruciate retaining tibial trial baseplate.

In some embodiments, there is provided a bone removal tool for removing an anterior portion of a tibial eminence on a proximal tibia, the bone removal tool comprising: at least one bone removal instrument for removing the anterior portion of the tibial eminence; and a guide for guiding the movement of the bone removal instrument into the proximal tibia, the guide comprising: a substantially planar medial reference surface for referencing a medial plateau resection on the proximal tibia; and a substantially planar lateral reference surface for referencing a lateral plateau resection on the proximal tibia; and a horizontal guide positioned to guide the movement of the bone removal instrument into an anterior portion of the tibial eminence in a plane that is substantially parallel to or coplanar with the substantially planar medial and lateral reference surfaces; wherein the guide defines a gap between the medial and lateral reference surfaces, the gap being sized and positioned to receive portions of the tibial eminence that include at least an anterior cruciate ligament attachment site. In some embodiments, the guide further comprises a vertical guide positioned to guide the movement of a second bone removal instrument into the anterior portion of the tibial eminence in a plane that is not substantially parallel to or coplanar with the substantially planar medial and lateral reference surfaces. In some embodiments, the guide further comprises a vertical guide positioned to guide the movement of the bone removal instrument into the anterior portion of the tibial eminence in a plane that is not substantially parallel to or coplanar with the substantially planar medial and lateral reference surfaces. In some embodiments, the vertical guide is positioned to guide the movement of the bone removal instrument in a plane that is substantially perpendicular to the substantially planar medial and lateral reference surfaces. In some embodiments, the guide comprises a guide assembly including a bicruciate retaining tibial trial baseplate and a modular guide removably positioned in a fixed position with respect to the bicruciate retaining tibial trial baseplate.

BRIEF DESCRIPTION OF DRAWINGS

FIGS. 7a through 7f show several anterior and sagittal views of a femoral implant, inferior portions of the femoral implant, and a distal femoral trial.

FIG. 8 shows a distal femoral trial positioned in the joint space between the distal femur and proximal tibia.

FIGS. 10 through 14 illustrate various kits of distal femoral trials.

FIGS. 23 through 29 illustrate various methodologies and apparatus for removing a sulcus portion of a distal femur.

FIG. 33 illustrates another use for a femoral trial.

FIGS. 34a through 34g are various views of an alignment block.

FIGS. 37a through 37e are various views of an extramedullary rod connector.

FIG. 38 shows the alignment block of FIG. 34 pinned to a proximal tibia, and an extramedullary alignment rod associated with the alignment block by the extramedullary rod connector of FIG. 37.

FIGS. 39a through c show additional views of the alignment block of FIG. 35.

FIGS. 40a through 40e are various views of a secondary alignment block.

FIGS. 41 through 43 show another embodiment of a secondary alignment block.

FIGS. 45a through 45c show various views of a medial tibial resection guide.

FIGS. 46 through 48 show other embodiments of medial tibial resection guides.

FIGS. 49a through 49e show various configurations of a stylus.

FIGS. 50 and 51 show other stylus embodiments.

FIGS. 60 through 74 illustrate various methodologies for positioning, re-positioning, adjusting and/or checking the position and/or orientation of various embodiments of medial tibial resection guides and styli with respect to a proximal tibia.

FIGS. 99 through 107 illustrate various methodologies and apparatus for making a lateral plateau resection on the proximal tibia.

FIGS. 108 through 112 show various views of a tibial trial baseplate.

FIGS. 113 through 159 illustrate various apparatus and methodologies for punching a keel cavity in the proximal tibia, removing an anterior portion of an eminence on the proximal tibia, and gauging clearance around the resected eminence of the proximal tibia.

DETAILED DESCRIPTION OF DRAWINGS

Figure 30:
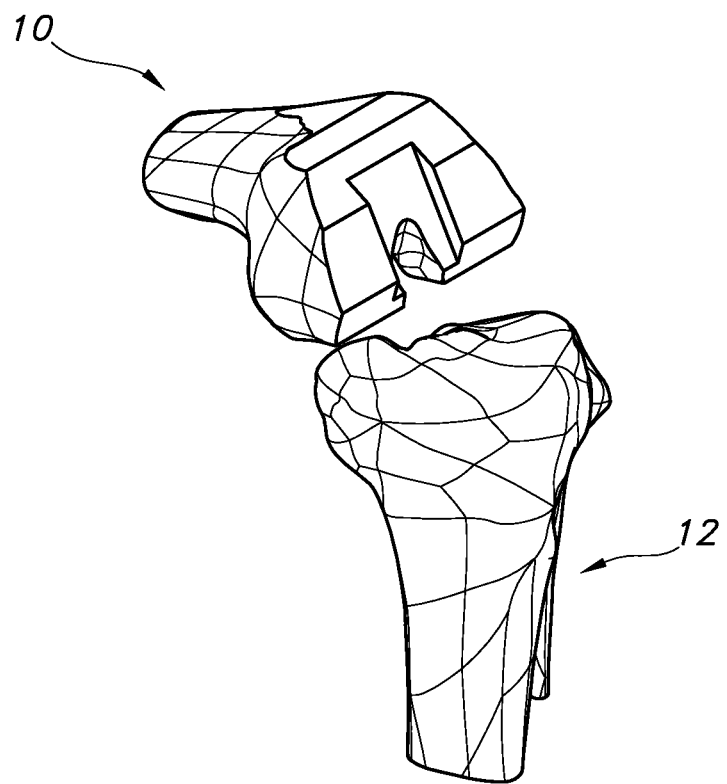
FIG. 30 shows the distal femur after resection, along with an unprepared proximal tibia.
Figure 31:
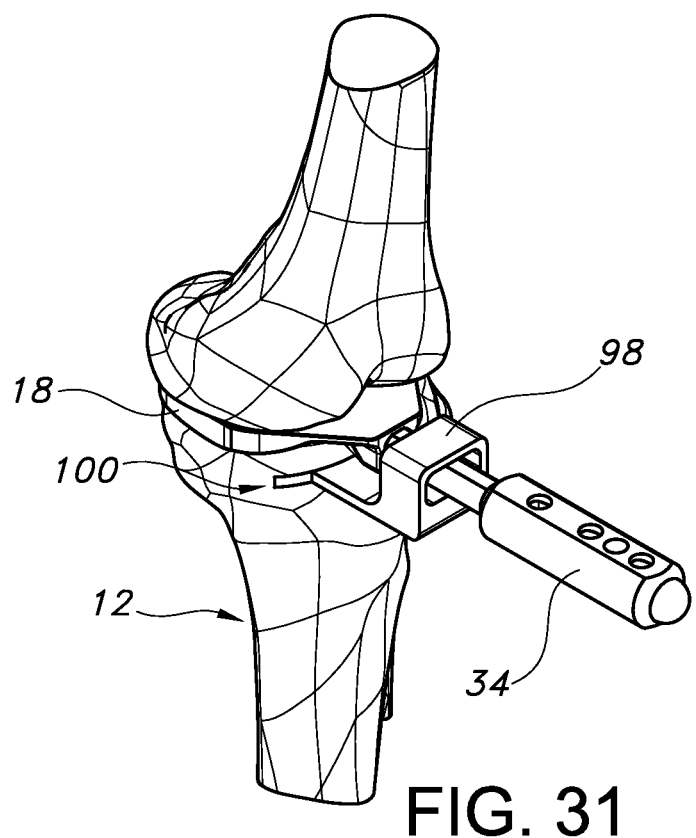
FIG. 31 illustrates another use for a distal femoral trial.
Figure 162:
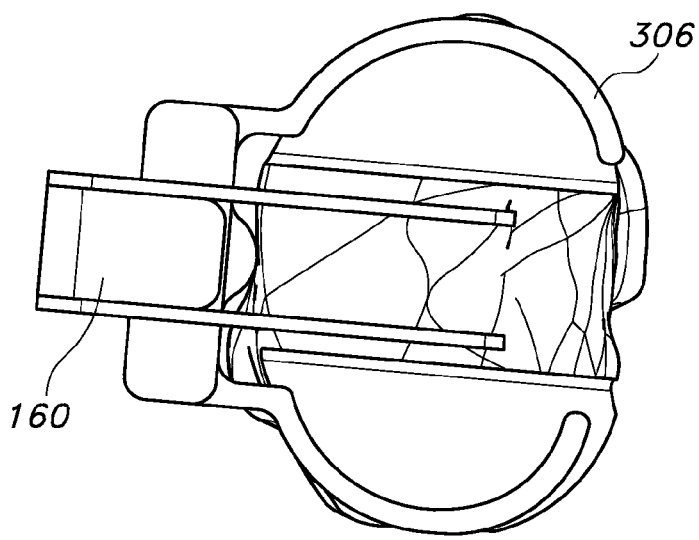

The following description of the non-limiting embodiments shown in the drawings is merely exemplary in nature and is in no way intended to limit the inventions disclosed herein, their applications, or uses. FIGS. 1-30 illustrate examples of methods and apparatus for preparing a distal femur for a femoral implant during a knee arthroplasty. FIGS. 31 to 162 illustrate examples of methods and apparatus for preparing a proximal tibia for a tibial implant during a knee arthroplasty.

Femoral Resections

There is a strong relationship between femoral attachment locations of soft tissues and the articulation between the tibia and femur. As a general matter, it can be shown that for knee implant designs relying more on contrived means of kinematic control and stability rather than on the native soft tissue structures, kinematic patient outcomes are less sensitive to mismatch between, for instance, the inferior/superior position of the native femoral articular surfaces and the implanted femoral articular surfaces, although such mismatches can still be significant in some instances. When more native structures are preserved in order to provide kinematic control and stability (e.g., with bi-cruciate retaining implants), however, the preservation of the femoral joint line can become more important to patient outcome, at least in some situations.

Currently, the common practice is to favor resection of the distal femur to the level of the trochlea, rather than by measuring a resection depth from the medial femoral condyle. It may be preferable, however, in at least some cases, to utilize methods and apparatus that counteract any tendency to resect the distal femur at a level other than the thickness of the distal femoral implant. For example, it may be preferable to resect an amount equivalent to the thickness of the distal femoral implant as measured from the distal medial (and/or lateral) condyle, which may better account for the mesial attachment sites on the femur of the posterior and/or anterior cruciate ligaments. It may also be preferable in at least some cases to utilize methods and apparatus that allow for early trialing and assessment of extension space and laxity. Some examples of such methods and apparatus are described below.

Some of the methodologies discussed below also reduce the complications of knee arthroplasty procedures by not solving for femoral and tibial degrees of freedom simultaneously, but instead by preparing the femur first, and then subsequently preparing the tibia. By completing all of the femoral resections prior to the tibial resections, the surgeon is provided with a fixed set of values from which he or she can determine the remaining tibial degrees of freedom. Another benefit of preparing the femur first provided by some of the methodologies described below is that they ensure proper kinematics. For proper kinematics, the femoral implant should generally conform to and articulate with the native anatomy well (e.g., natural soft tissues and native tibial cartilage). By separating the femoral resection steps from the tibial resection steps, the surgeon has no other input variables with which to make femoral resection decisions other than input variables provided by the native femoral anatomy.

A third benefit of preparing the distal femur before the tibia in some of the embodiments discussed below is that a surgeon still has the flexibility of performing a posterior stabilized, cruciate retaining, or bicruciate retaining surgery with little or no time penalty or bone-loss, even after the femoral side has been prepared.

Many of the methods and apparatus described below, however, are not limited to only femur first techniques, or techniques that achieve all of the above benefits.

Figure 1:
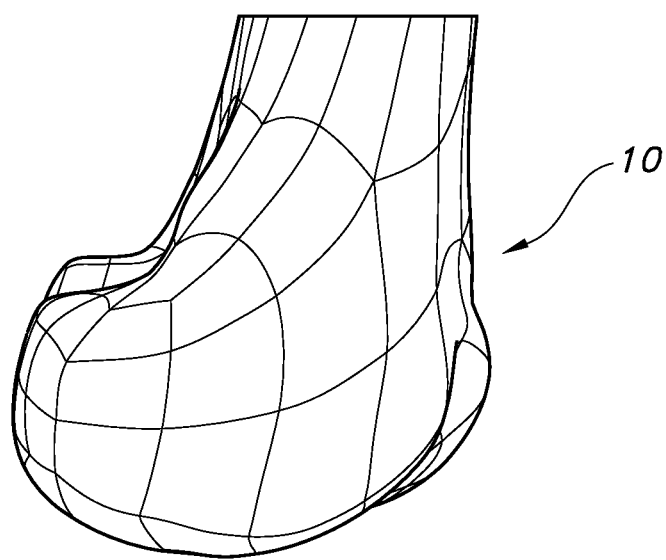
FIG. 1 is a sagittal view of a distal portion of a femur.
Figure 2:
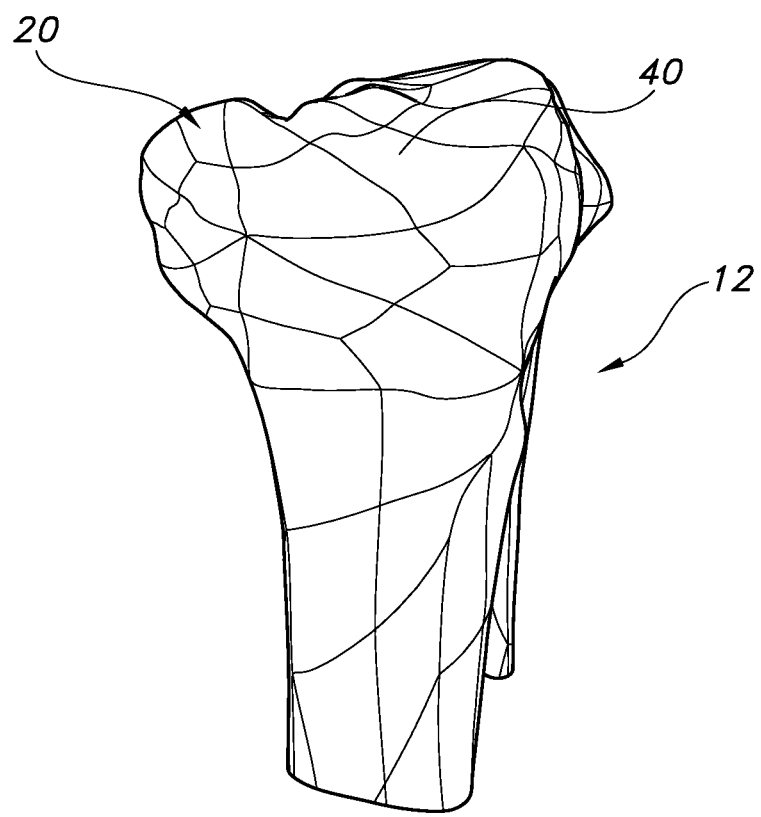
FIG. 2 is a perspective view of a proximal portion of a tibia.

FIGS. 1 through 9 illustrate one distal bone cut first method and apparatus for carrying out such a method in relation to the distal femur 10 shown in FIG. 1 and the proximal tibia 12 shown in FIG. 2.

Figure 3:
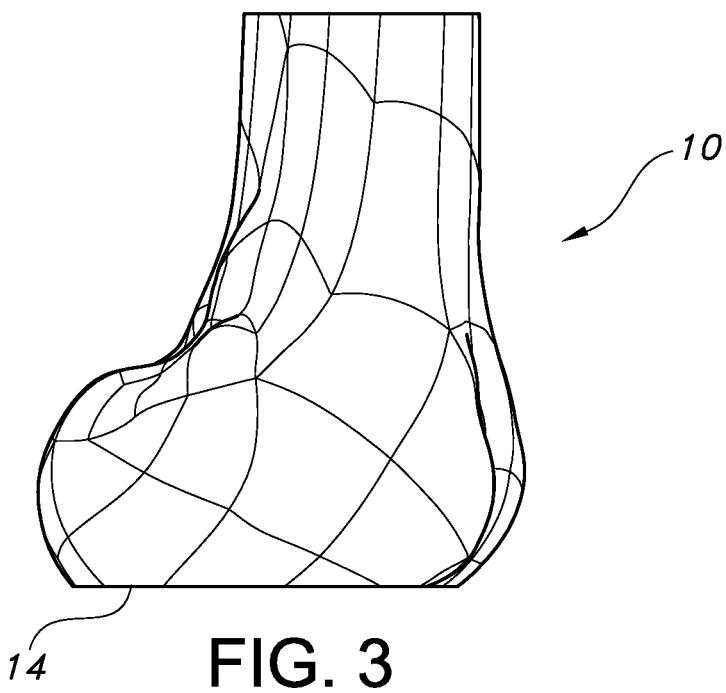
FIG. 3 is a sagittal view of the distal femur of FIG. 1 after a distal resection.
Figure 4:
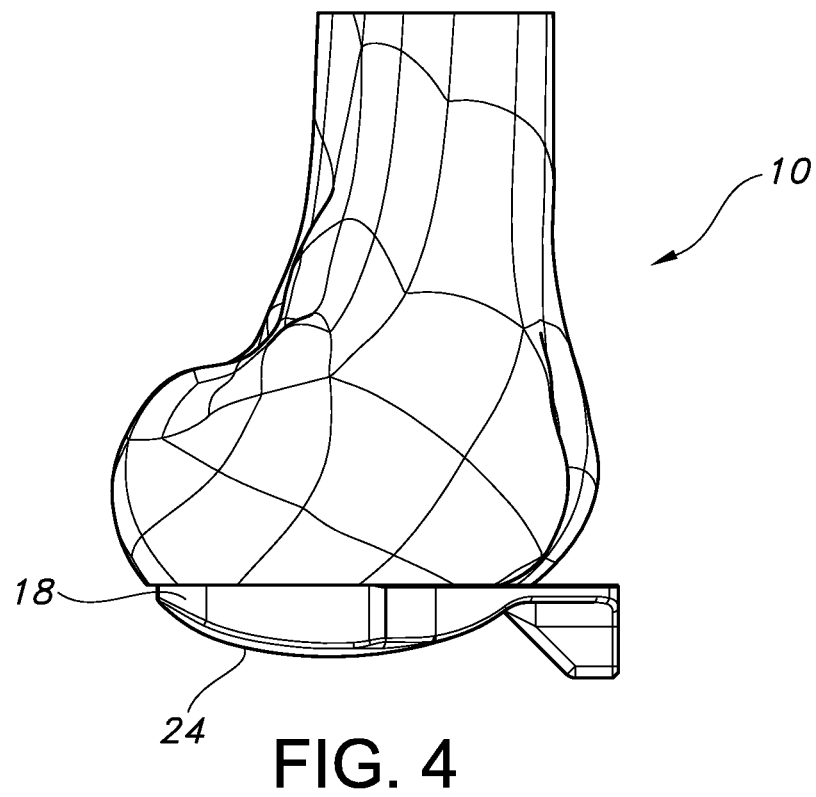
FIGS. 4 and 5 show a distal femoral trial positioned against the resected surface of the distal femur of FIG. 3.
Figure 5:
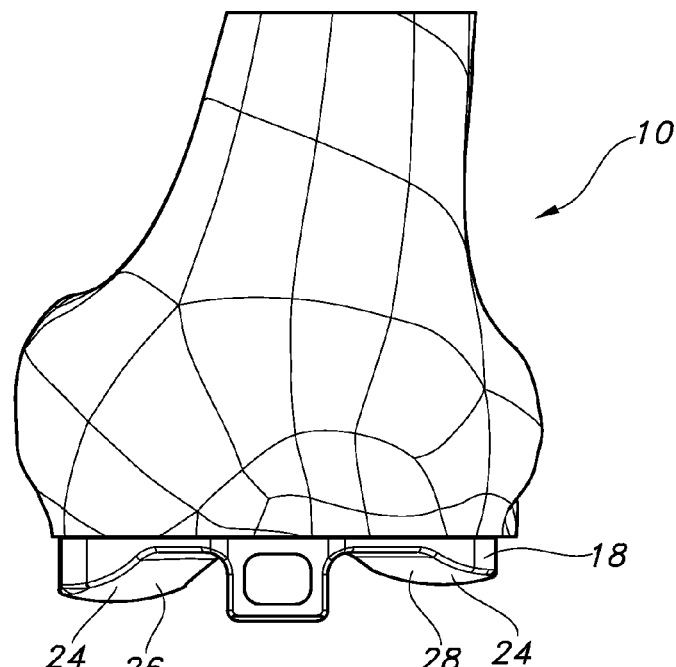

FIG. 1 shows the distal femur 10 before resection. FIG. 3 shows the distal femur 10 after resection to define a resected surface 14 on the distal femur 10. In some embodiments, the resected surface 14 is at a depth that approximately equals the distal thickness of a femoral implant 16 for eventual implantation on the distal femur 10. One non-limiting example of a suitable femoral implant 16 is shown in FIGS. 7a and 7d. The distal femoral resection can be performed using conventional or non-conventional techniques and apparatus. For instance, a conventional cutting block (not shown) could be navigated using the intramedullary canal and/or pinned to the distal femur with one or more (e.g. two) parallel pins to guide a reciprocating or oscillating saw or other cutting device to make the distal femoral resection. In some instances it may be desirable to leave the pins on the distal femur 10 in the event it becomes necessary to reattach the same cutting block or a different cutting block to re-cut the distal femoral resection.

FIGS. 4-8 show a distal femoral trial 18 and the insertion of the distal femoral trial 18 between the resected surface 14 on the distal femur 10 and an unresected surface on the proximal tibia 12 (such as the unresected surface 20 on the proximal tibia 12 shown in FIG. 2). As shown in FIGS. 4 through 8, the distal femoral trial 18 includes a superior, planar surface 22 and inferior, curved surfaces 24. The superior, planar surface 22 is configured for contact with the resected surface 14 on the distal femur 10. The inferior, curved surface 24, which includes a medial condylar surface 26 and a lateral condylar surface 28, is for contact with and at least some degree of articulation with the unresected surface 20 on the proximal tibia 12. The superior, planar surface 22 may be flat, smooth, or textured for improved friction with the bone forming and surrounding the resected surface 14 on the distal femur 10. As shown in FIGS. 7a through 7f, the distal femoral trial 18 of FIGS. 4 through 8 substantially replicates at least some of the shapes and thicknesses defined by the femoral implant 16, particularly at least some of the inferior portions 30 (shown in FIGS. 7c and 7e) of the femoral implant 16.

Figure 6:
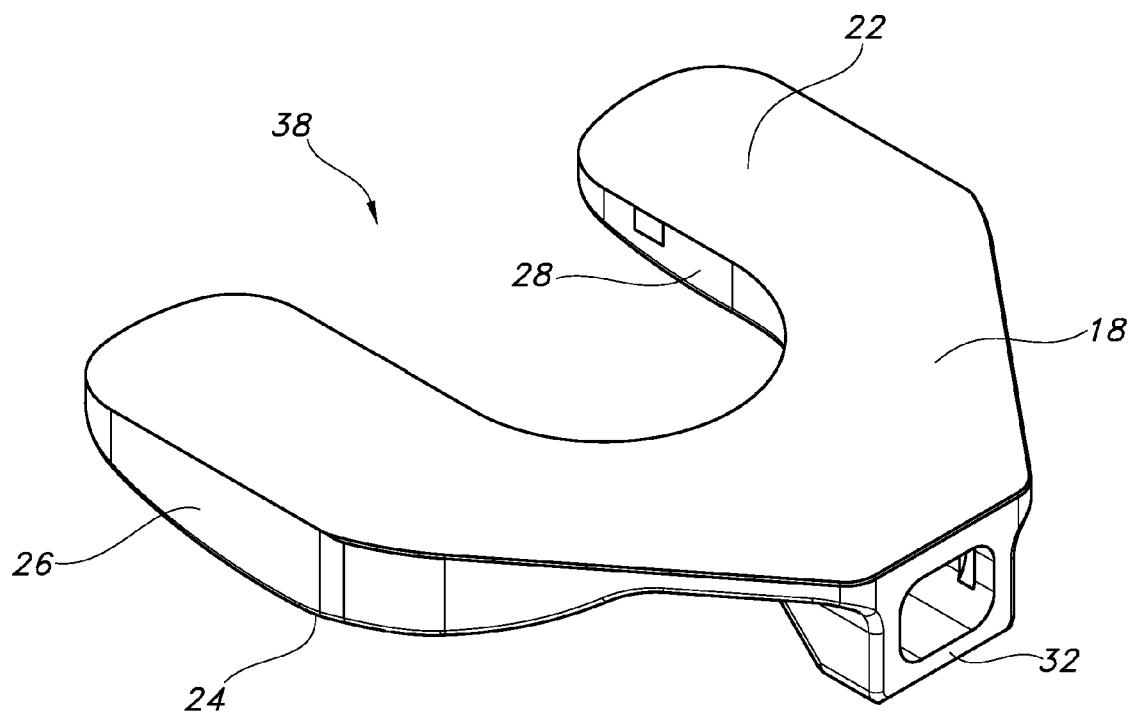
FIG. 6 is a perspective view of the distal femoral trial of FIGS. 4 and 5.

In the embodiment shown in FIGS. 4 through 8, the femoral implant 16 and the distal femoral trial 18 are designed to be used in bicruciate retaining procedures. For instance, as shown in FIG. 6, the distal femoral trial 18 is substantially U-shaped and defines a gap 38 between the medial and lateral condylar surfaces 26, 28 for receiving at least a portion of the tibial eminence 40 of the proximal tibia 12 (shown in FIG. 2). The tibial eminence 40 includes attachment sites for the anterior and posterior cruciate ligaments. The gap 38 of the distal femoral trial 18 is sized and positioned to avoid substantial interference with those ligaments when the distal femoral trial 18 is inserted between the resected surface 14 on the distal femur 10 and the unresected surface 20 on the proximal tibia 12, such an example of which is shown in FIG. 8.

The distal femoral trial 18 shown also includes an attachment site 32 (see FIG. 6) for connecting various tools and other apparatus. For instance, as shown in FIG. 8, the attachment site 32 can be used to connect a handle 34, which in turn can be used to connect other tools, such as the extramedullary alignment rod 36 shown. As shown in FIG. 6, the attachment site 32 may include geometry (e.g., but not limited to non-circular geometry) that allows items such as the handle 34 to be secured in a fixed angular position (e.g., non-rotating). Other mechanisms could also be employed with respect to attachment site 32 for securing items to it in a fixed angular position. For instance, attachment site 32 could facilitate the attachment of a fiducial construct used in some computer assisted surgery knee procedures. Examples of other tools and other apparatus that can connect to attachment site 32 are discussed further below.

Figure 9:
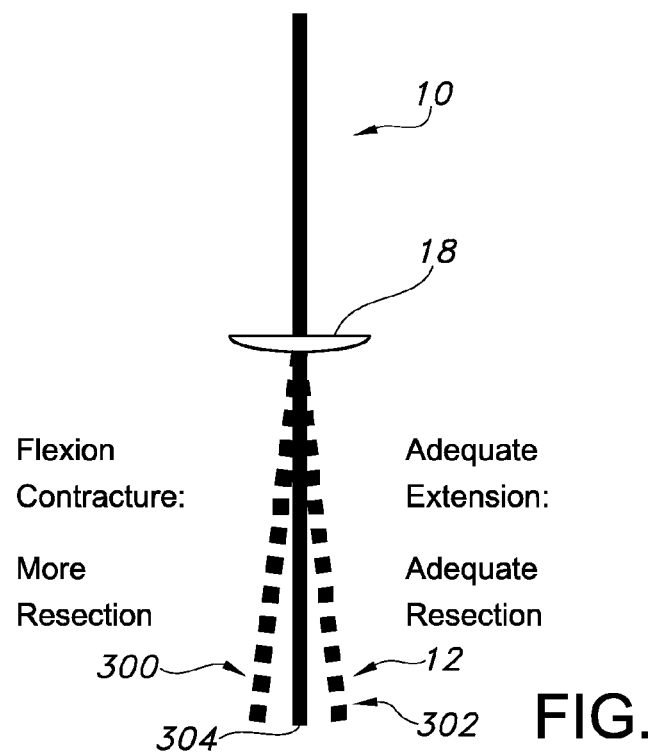
FIG. 9 schematically illustrates using a distal femoral trial to gauge for flexion contracture.

FIGS. 8 and 9 illustrate one way that the distal femoral trial 18 can be used to evaluate the distal femoral resection. FIG. 8 shows the distal femoral trial 18 inserted into the space between the resected distal femur 10 and the unresected proximal tibia 12. Although not explicitly shown in FIG. 8, the distal femur 10 and proximal tibia 12 of the knee joint are connected by the anterior and posterior cruciate ligaments, as well as other anatomy such as the medial collateral ligament, the lateral collateral ligament, and the patellar tendon. By inserting the distal femoral trial 18 into the joint space, the surgeon can evaluate the distal femoral resection.

For instance, if the distal femoral trial 18 is one that substantially replicates the shape and thickness of an inferior portion 30 of a femoral implant 16 in at least some geometries, and if the resected surface 14 on the distal femur 10 has been cut at a depth that approximately equals the distal thickness of the femoral implant 16, the surgeon can evaluate the expected tightness or laxity of the knee joint (taking into account the tension or laxity of one or more of the above mentioned ligaments and tendons) once the procedure is completed and the femoral implant 16 implanted and/or can evaluate for flexion contracture.

FIG. 9 schematically shows how a surgeon might evaluate the knee joint for flexion contracture. In the technique shown in FIG. 9, which schematically shows the positioning of a distal femur 10 relative to a proximal tibia 12, once the distal femoral trial 18 is inserted between the distal femoral resection and the unresected proximal tibia, the knee joint can be extended to a maximum amount of extension allowed by the knee joint. If the degree of maximum extension allowed is less than desired, less than that of a natural, healthy knee joint, and/or less than that of the knee joint of the patient prior to surgery (schematically illustrated by dashed line 300 in FIG. 9), it may indicate a flexion contracture to the surgeon and that a deeper resection of the distal femur is indicated (e.g. that the knee joint is "too tight"). In such instances, the cutting block may be reattached and the distal femoral resection could be re-cut for a re-evaluation using the same or a different distal femoral trial. If maximum extension is adequate (schematically illustrated by the dashed line 302 in FIG. 9), it may indicate to the surgeon that the level of the distal femoral resection is adequate and does not need to be recut. It should be understood that although the dividing line (schematically illustrated by solid line 304) between flexion contracture and adequate extension is shown in FIG. 9 as occurring at approximately 0 degrees of flexion, the dividing line does not have to be so located, and, depending on the particular circumstances of the patient or other factors, could be at more or less than 0 degrees of flexion.

One advantage of the distal femoral trial 18 embodiment shown in FIGS. 4 through 9 is that it can be used without having to resect the tibia. Many conventional spacer blocks used in gap balancing and other evaluations of resections in knee arthroplasty procedures require at least one resection of both the tibia and femur to function properly. The distal femoral trial 18 shown in FIGS. 4 through 9, on the other hand, facilitates the evaluation of the resected surface 14 on the distal femur 10 relative to an unresected surface 20 on the proximal tibia 12, and thereby provides information about the level of the resection absolutely. Since the conventional spacer blocks measure a femoral resection relative to a tibial resection, they can only provide information about the spacing between the resections and not about the joint line orientation and position of the femoral resection relative to other important anatomy of the knee joint.

Therefore, in methods where at least one, if not all, of the femoral resections are made prior to resecting the proximal tibia, the distal femoral trial 18 of FIGS. 4 through 9 can be used to provide information about the distal femoral resection level earlier in the surgery than conventional spacer blocks. Having access to such information earlier in surgery reduces the likelihood of propagating errors which could result in poor outcomes and increased surgery time.

Another advantage of the methodologies illustrated by FIGS. 4 through 9 over many conventional technologies utilizing conventional spacer blocks is that these conventional techniques and spacers may generate a "false laxity" in the extension space. For example, false laxity in extension can be common when using a conventional spacer block to check flexion and extension gaps after the posterior condyles have been resected, since, in some instances, posterior portions of the condyles provide some tension to the various anatomy constraining and otherwise interacting with the knee joint. By using the distal femoral trials provided herein, a user is obliged to gauge the extension laxity in an environment which is most likely to give correct feedback.

It will be apparent to one of skill in the art that the above described methodologies and apparatus can be used to evaluate the distal femoral resection in other ways. For instance, in some embodiments, the distal femoral trial 18 may allow the surgeon to evaluate in an early stage of the procedure (e.g. prior to other substantial resections or disruptions to the patient's anatomy) the appropriateness of the bicruciate retaining implant and procedure for the particular patient, or if a posterior cruciate retaining, bicruciate sacrificing (e.g., for a posterior-stabilized implant), or other implant/procedure should be pursued instead. In combination with the above described or other evaluation techniques, the distal femoral trial 18 can be associated with a handle 34 and a extramedullary alignment rod 36 (such as shown, e.g., in FIG. 8) to facilitate visualization of mechanical and anatomical alignments. In still other embodiments, distal femoral trials other than those that replicate or substantially replicate the intended femoral implant can be used to evaluate the distal resection or other aspects of the knee joint in other ways.

Figure 32:
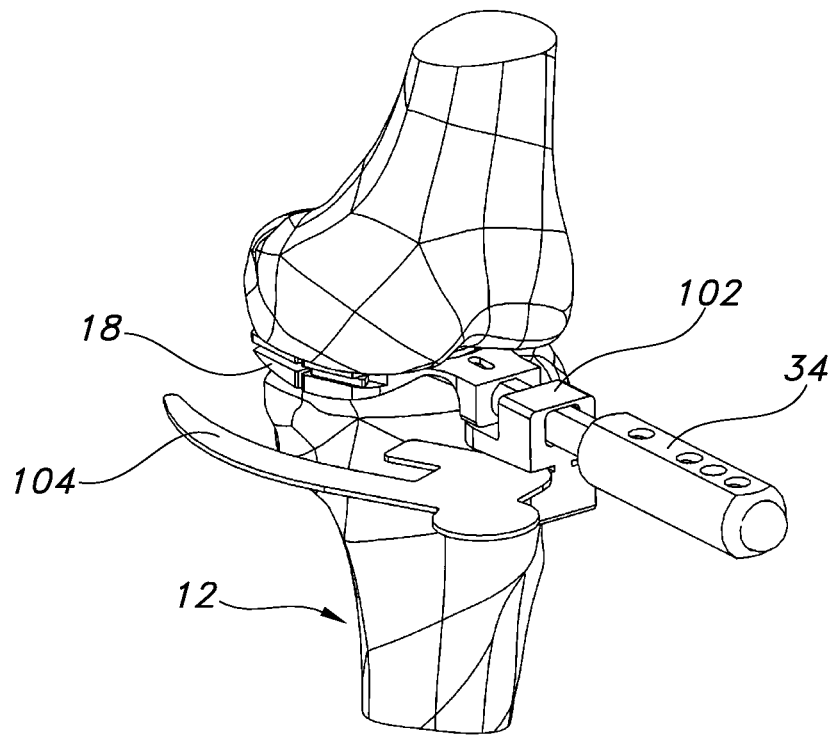
FIG. 32 illustrates another use for a distal femoral trial.

In some embodiments, such as the embodiments illustrated in FIGS. 31 through 33, the distal femoral trial 18 or other types of femoral trials can facilitate identifying an appropriate depth on the proximal tibia 12 for resection. FIG. 31 shows a tibial depth gauge 98 attached to the handle 34 for marking (using a surgical marker or other apparatus) indicia 100 on the proximal tibia 12 to indicate the desired depth of a tibial resection or other information relevant to the knee arthroplasty. Although not shown, in some embodiments, it may be desirable to connect an extramedullary alignment rod 36 or other alignment facilitating devices to ensure that the knee joint is in a proper level of extension or flexion or otherwise appropriately aligned before marking indicia 100.

FIGS. 32 and 33 illustrate other apparatus that could be used with the distal femoral trial 18 (FIG. 32) or another femoral trial 80 (FIG. 33) to indicate tibial depth. FIG. 32 shows an alignment block 102 connected to the distal femoral trial 18 via an associated handle 34. The alignment block 102 could be used to mark an indicia on the proximal tibia 12 or, in some embodiments, could be pinned directly to the proximal tibia 12. Because the connection between the distal femoral trial 18 and the alignment block 102 positions the alignment block 102 in a fixed angular position with respect to the distal femoral trail 18, the position of the distal femoral trial 18 and its associated handle 34 (and at least to some extent the degree to which the knee joint is in flexion or extension) will control the positioning and orientation of the alignment block 102 with respect to the proximal tibia 12, such as its superior/inferior positioning, its varus/valgus angulation, and its posterior slope. Movement of the knee joint through flexion/extension, however, may at least partially affect some of these positions and orientations of the alignment block 102 with respect to the proximal tibia 12. Accordingly, in some embodiments, it may be desirable to also use an extramedullary alignment rod 36 (shown in FIG. 8) or an indicator 104 (shown in FIG. 32) to confirm the proper and/or desired positioning of the alignment block 102 on the proximal tibia 12.

FIGS. 10 through 13 illustrate embodiments of surgical kits that include sets 42 of different distal femoral trials 18. For example, FIGS. 11a through 11c schematically show a set 42 of distal femoral trials 18 that simulate different femoral implant sizes. The set shown includes three sizes of distal femoral trials 18: a first to simulate femoral implants having a size of 1-2 medial-lateral width and a 9.5 mm medial condyle thickness; a second to simulate femoral implants having a size 3-8 medial-lateral width and a 9.5 mm medial condyle thickness; and a third to simulate femoral implants having a size 9-10 medial-lateral width and a 11.5 mm medial condyle thickness. In some embodiments, the condylar radii of each distal femoral trial 18 may generally equal the average of each condylar radii within the size range. For instance, the size 1-2 distal femoral trial may have medial and lateral condylar radii approximately equal to the average of size 1 and size 2 medial and lateral radii, respectively. In other embodiments, the condylar radii of the distal femoral trial may generally equal the smallest or the largest condylar radii within a particular femoral implant size range. For instance, the second distal femoral trial 18 (representative of femoral sizes 3-8) may have medial and lateral condylar radii approximately equal to that of a size 3 (smallest within size range) or a size 8 (largest within size range) femoral implant.

In another example, a set of distal femoral trials 18 are provided within a surgical kit, each of the distal femoral trials having a size that corresponds exactly to a particular femoral implant size. In this example, more distal femoral trials may need to be provided to the surgical kit. However, if each distal femoral trial is representative of a single femoral implant size, then there is no need to average the medial and lateral distal radii or choose an medio-lateral width to represent an entire size range with a single distal femoral trial. Therefore, evaluations of laxity and maximum extension may be made more accurately at the expense of providing a larger number of distal femoral trials to the surgical kit.

Figure 10:
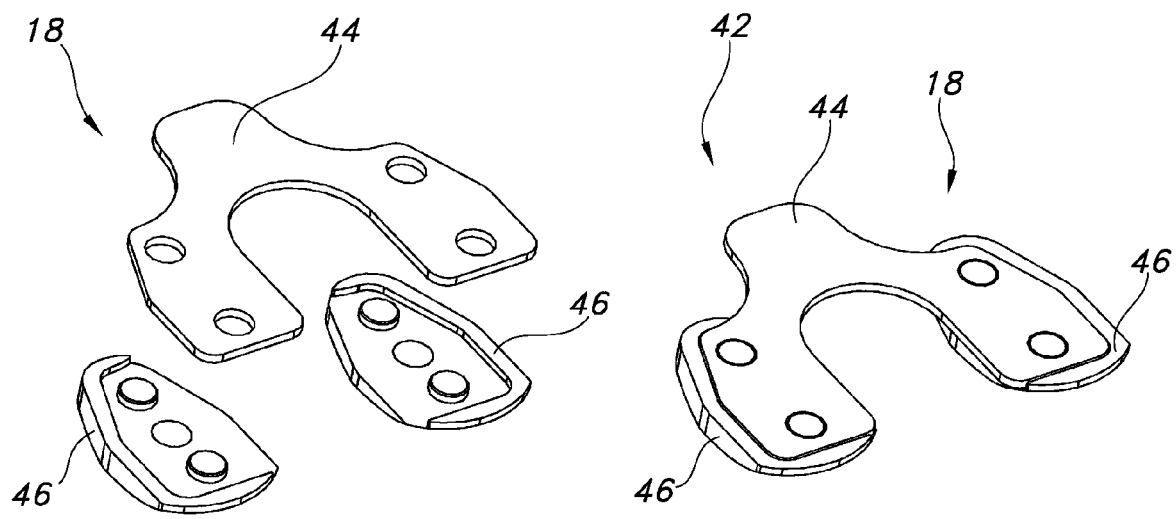
Figure 13A:
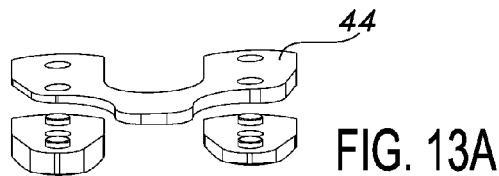
Figure 13G:
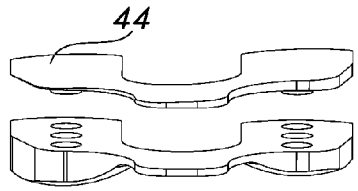
Figure 13B:
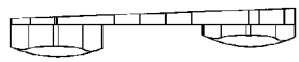
Figure 13H:
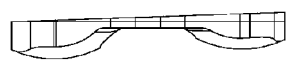
Figure 13C:
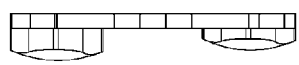
Figure 13I:
Figure 13D:
Figure 13J:
Figure 13E:
Figure 13K:
Figure 13F:
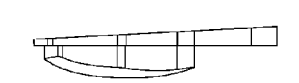
Figure 13L:
Figure 14A:
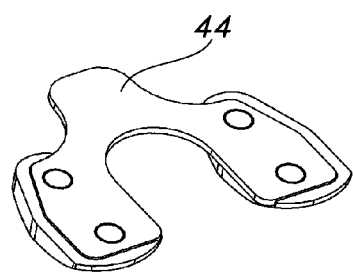
Figure 14C:
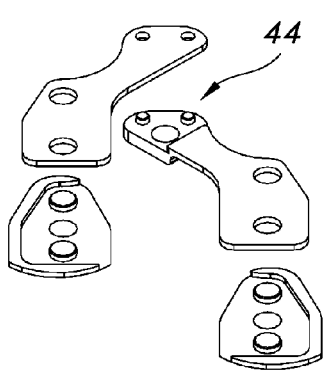
Figure 14B:
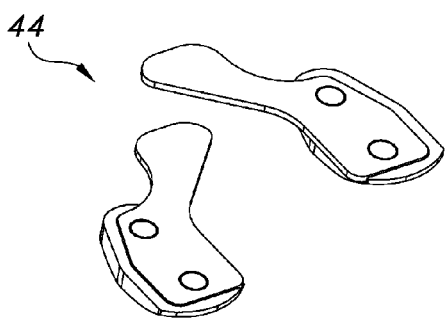
Figure 14D:
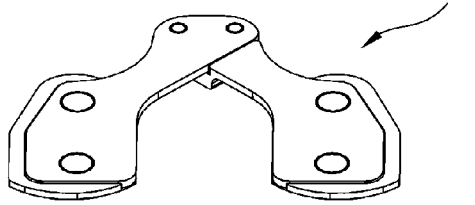
Figure 15:
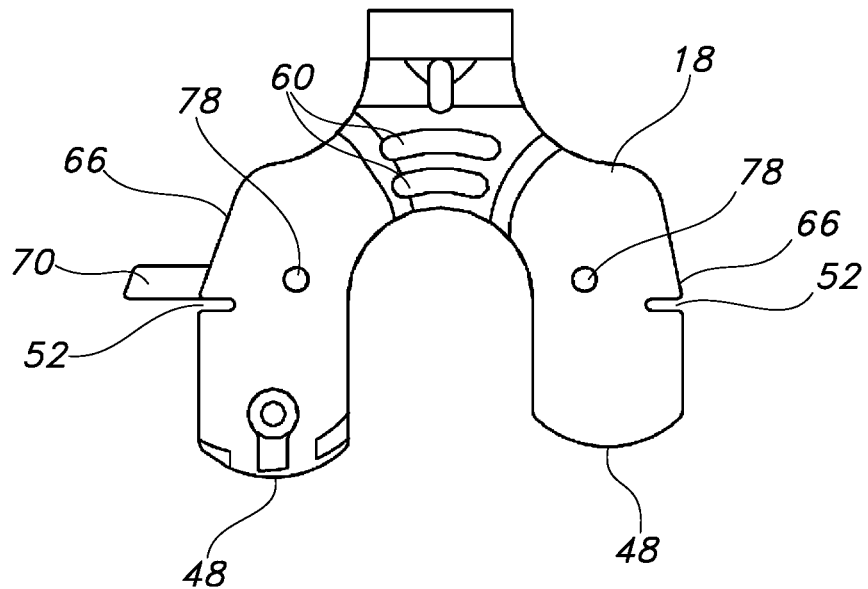
FIGS. 15 through 20 show various configurations of distal femoral trials and the use of such distal femoral trials as gauges.
Figure 16:
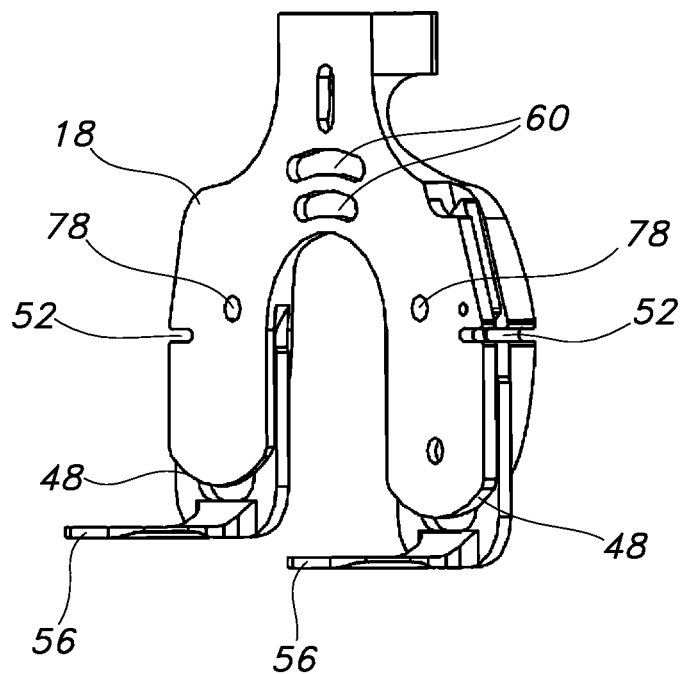

FIG. 10 shows a set 42 of distal femoral trials 18 that are modular. In the embodiment of FIG. 10, each distal femoral trial 18 includes a baseplate 44 that can be connected to a pair of modular shims 46 to form a distal femoral trial 18 of a particular size.

FIGS. 12 and 13 show sets of modular distal femoral trials that use baseplates 44 and shims 46 to vary specific geometries of the distal femoral trial 18. For instance, in the embodiment of FIGS. 12a through 12h, shims 46 facilitate modifying the thickness of the medial and lateral condylar portions of the distal femoral trial. In some uses, the set of modular distal femoral trials illustrated in FIG. 12 may help to account for cartilaginous and bony deficiencies in the articular surface of the tibia and/or femur, abnormalities, or other deviations (or patient specific morphology of the femoral condyles) while evaluating the distal femoral resection. FIGS. 13a through 13l show a set of modular distal femoral trials in which the modular baseplates 44 can be used to vary the overall thickness of the distal femoral trial as well as or alternatively to varying certain angular geometries of the distal femoral trials, such as the varus/valgus angle or flexion/extension angles of the distal femoral trial. FIGS. 14a through 14d show another example of a set of distal femoral trials in which the baseplate 44 itself can be modular, allowing medial and lateral portions of the baseplate to be changed independent of the other portion. In some embodiments, the baseplates 44 shown in FIGS. 14a through 14d could be used individually (e.g. just a medial portion or just a lateral portion) for various purposes, such as for use in unicondylar knee arthroplasty.

In yet other embodiments, the distal femoral trials may include adjustment mechanisms that allow portions of the distal femoral trials to be expanded and/or contracted with respect to other portions to adjust the size, thicknesses, angular geometries or other geometries of the distal femoral trial.

As shown in FIGS. 15 through 20, in some embodiments, the distal femoral trial 18 can be used as a gauge for gauging and/or setting internal/external rotation, anterior/posterior position, and/or size of the distal femoral trial 18 with respect to the resected surface 14 on the distal femur 10. This gauging functionality may facilitate the surgeon's visualization or planning for how the femoral implant 16 will be positioned and oriented on the distal femur 10 at the end of the procedure.

Figure 17:
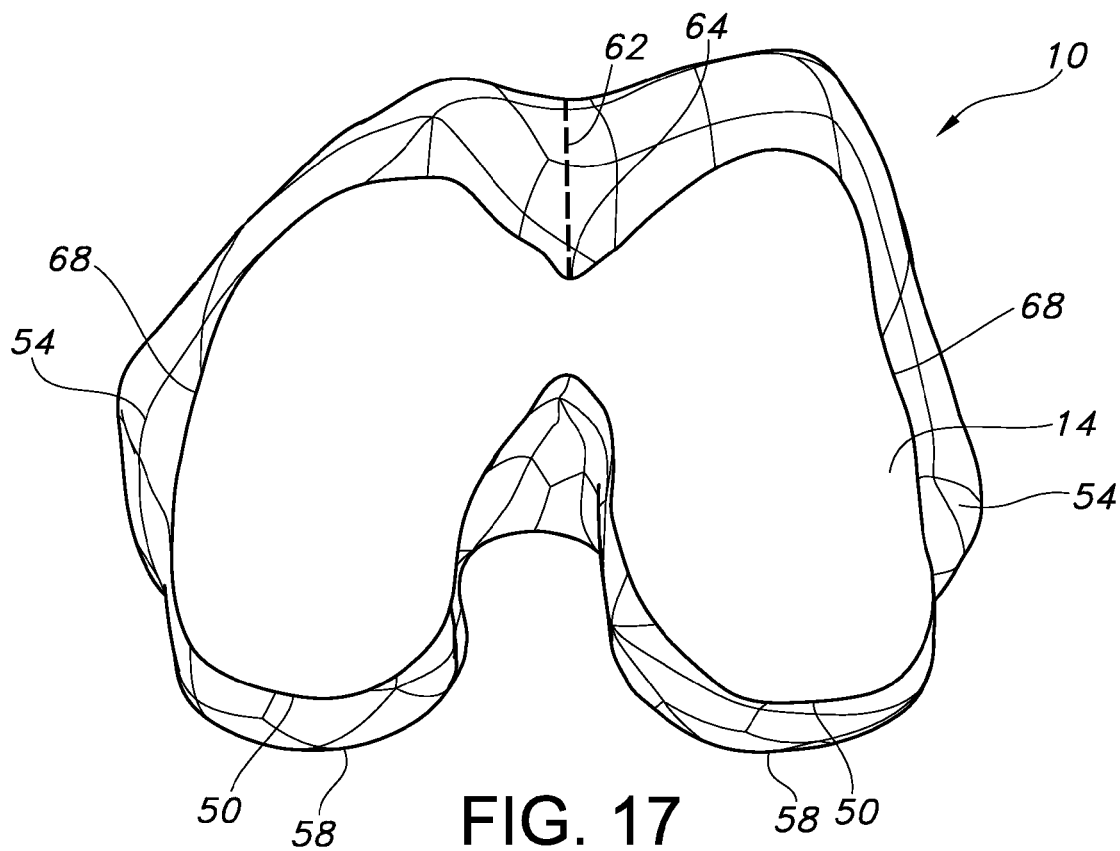
Figure 18:
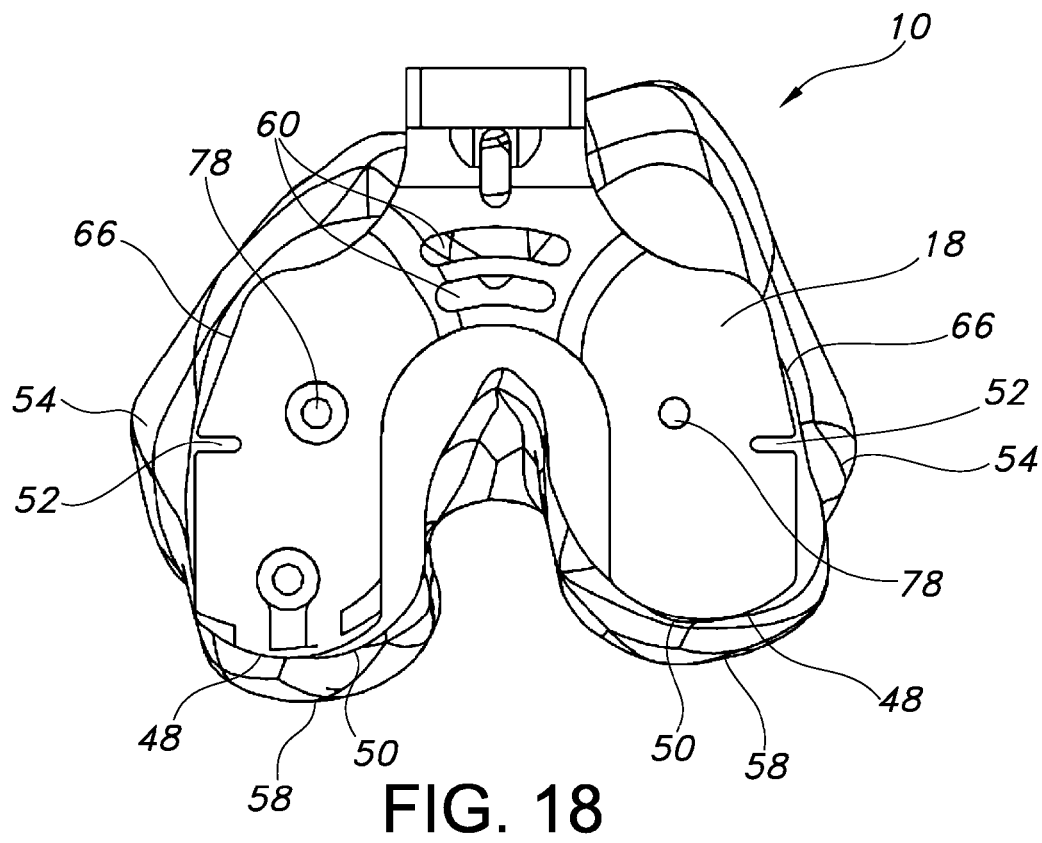

The distal femoral trial 18 shown in FIGS. 15 through 20 includes various references that indicate a position of the distal femoral trial 18 with respect to the distal femur 10 and the resected surface 14 on the distal femur 10. For instance, posterior edges 48 of the inferior curved surface of the distal femoral trial 18 may be used to reference the posterior edges 50 of the resected surface 14 on the distal femur 10 (as shown in FIG. 17). Paddles 56 may extend substantially perpendicular from posterior portions of the distal femoral trial 18 to reference posterior portions of the medial and lateral condyles 58 of the distal femur 10. Windows 52 extending through the distal femoral trial 18 may be used to reference the medial and lateral epicondyles 54 of the distal femur 10. Another window or windows 60 can be used to indicate the position of the distal femoral trial 18 with respect to an AP axis 62 of the distal femur 10 and/or a central anterior V point 64 of the resected surface 14 on the distal femur 10. Other references, such as indicia markings on the distal femoral trial, could also be used either by themselves or in conjunction with windows, paddles and other references described above. In some embodiments, anterior surfaces or edges of the distal femoral trial 18 could be used to reference anterior edges of the distal femoral resection 14.

In some embodiments, posterior edges 48, windows 52, paddles 56, windows 60 and/or other references may be used (in various combinations) to gauge the internal/external rotation of the distal femoral trial 18 with respect to the distal femur 10, which may be used, in some instances, to visualize and/or plan for the final positioning of the femoral implant 16 on the distal femur 10.

Figure 19:
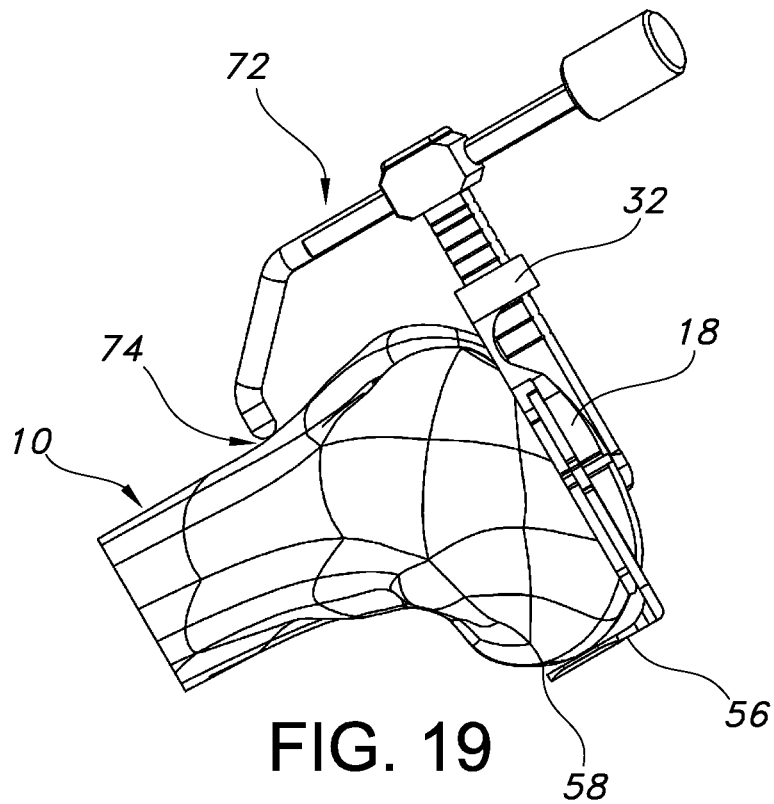
Figure 20:
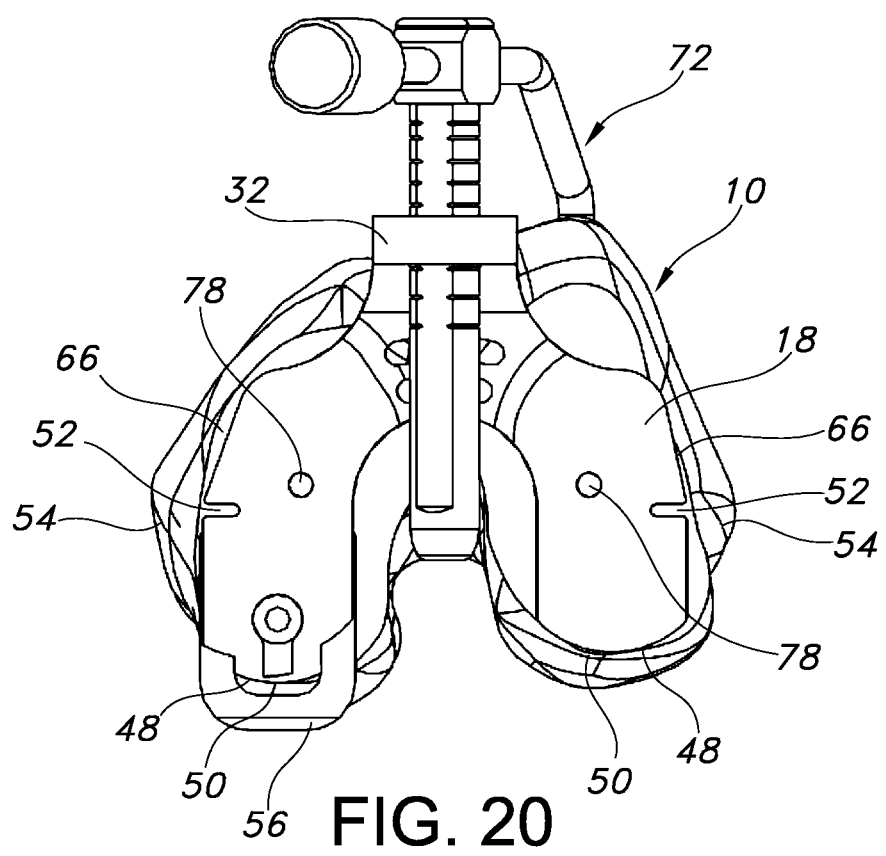

The distal femoral trial 18 shown in FIGS. 15 through 20 can also be used to gauge femoral size and AP position. Many of the same references described above, such as the posterior edges 48, paddles 56, and windows 60 can be used to gauge size and position. Other references on the distal femoral trial may also be useful, such as, for instance, the relative position of medial and lateral edges 66 of the distal femoral trial 18 with respect to medial and lateral edges 68 of the resected surface 14, or the relative position of a deployable arm 70 or arms (or indicia, not shown, on a deployable arm or arms) with respect to the medial and lateral edges 68, which may be useful in identifying or evaluating a medial—lateral sizing of the femoral implant. As shown in FIGS. 19 and 20, an anterior stylus 72 can be associated with the distal femoral trial 18 (in the embodiment shown in FIGS. 19 and 20, by positioning the anterior stylus 72 at the attachment site 32 of the distal femoral trial 18) to reference the position of the anterior cortex 74 of the distal femur 10.

Once a desired position and/or rotation of the distal femoral trail 18 with respect to the distal femur is achieved, if desired, the surgeon can create indicia on the distal femur to record that information for future use in the procedure. For instance, the distal femoral trial 18 shown in FIGS. 15 through 20 includes openings 78 to receive bone pins, a surgical marker or a cutting device that could mark or place indicia on the distal femur.

Figure 21:
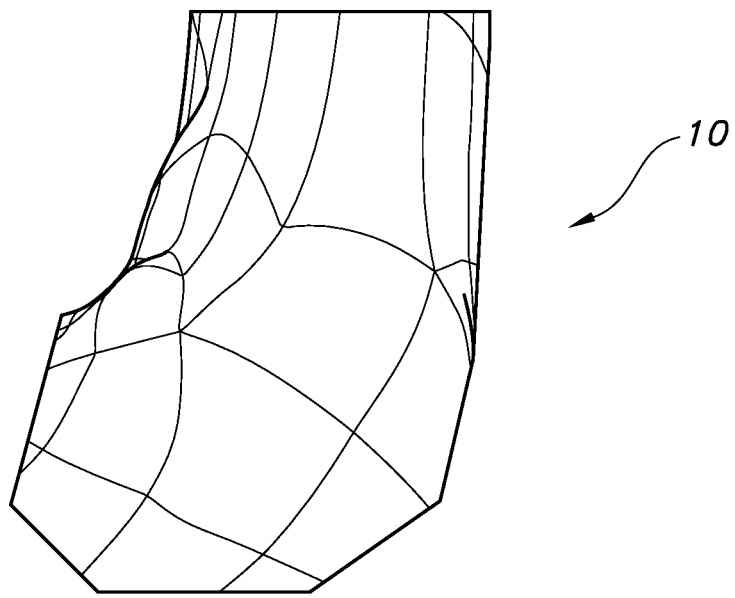
FIG. 21 is a sagittal view of a distal portion of a femur after a box bone cut.

In some embodiments, after an evaluation of laxity and extension or other aspects of the distal femoral resection is complete, a conventional "box-bone cut" may be provided to the distal femur 10 as illustrated in FIG. 21. The box-bone cut may be created by placing a five-in-one cutting block on the distal femoral resection, making posterior bone cuts to the medial and lateral condyles, making posterior chamfer bone cuts to the medial and lateral condyles, making an anterior bone cut to the distal femur, making an anterior chamfer bone cut; and then, if appropriate, making an anterior "roll-on bone cut" on the distal femur 10 between the anterior chamfer bone cut and the anterior bone cut. The roll-on bone cut generally allows a femoral component having converging posterior and anterior bone cuts to be implanted easily without binding. In some embodiments, the indicia on the distal femur 10 created using the gauging functionality of the distal femoral trial 18 could be used to position the five-in-one cutting block.

Figure 22:
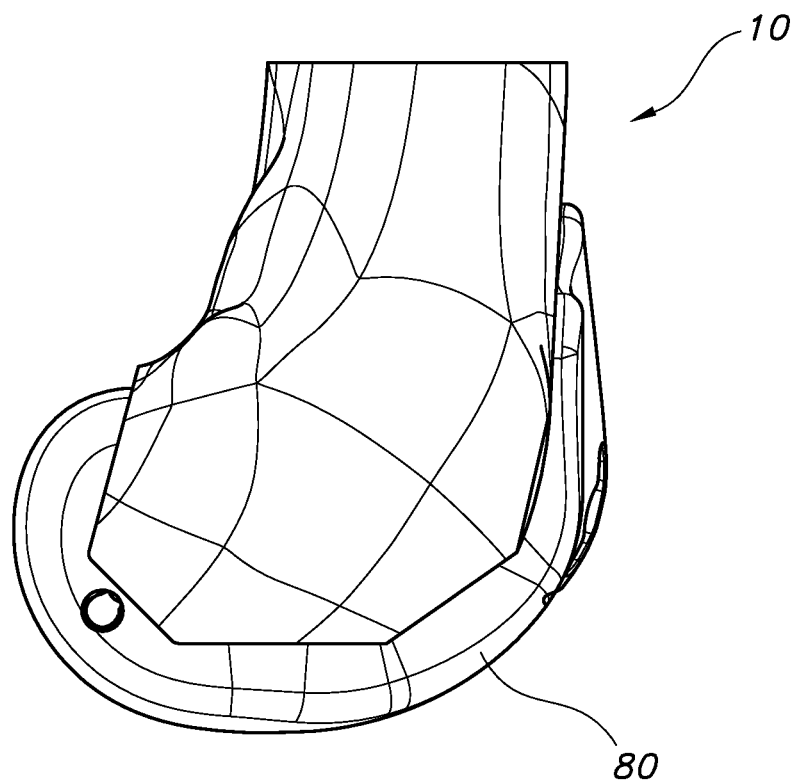
FIG. 22 is a sagittal view of a femoral trial positioned on the distal femur after the box bone cut of FIG. 21.

FIG. 22 shows a femoral trial component 80 having a bone-engaging surface matching said box bone cut installed onto the distal femur 10. The femoral trial component 80 may be provided with a femoral cutting guide configured to receive and guide a notched cutter (as described below for FIGS. 23 to 28), another type of cutter (as described below for FIG. 29) or other features discussed further below. In some embodiments, such as the embodiment shown in FIGS. 23 through 25, the femoral cutting guide is a separate component 82 that can be secured with respect to femoral trial component 80 (such as shown in FIGS. 23 through 25 and 29). In other embodiments (such as shown in FIGS. 26 through 28), the femoral cutting guide is an integral part of the femoral trial component 80. In some embodiments (not shown) the femoral cutting guide can be a separate component that is not used with the femoral trial component 80.

Figure 23:
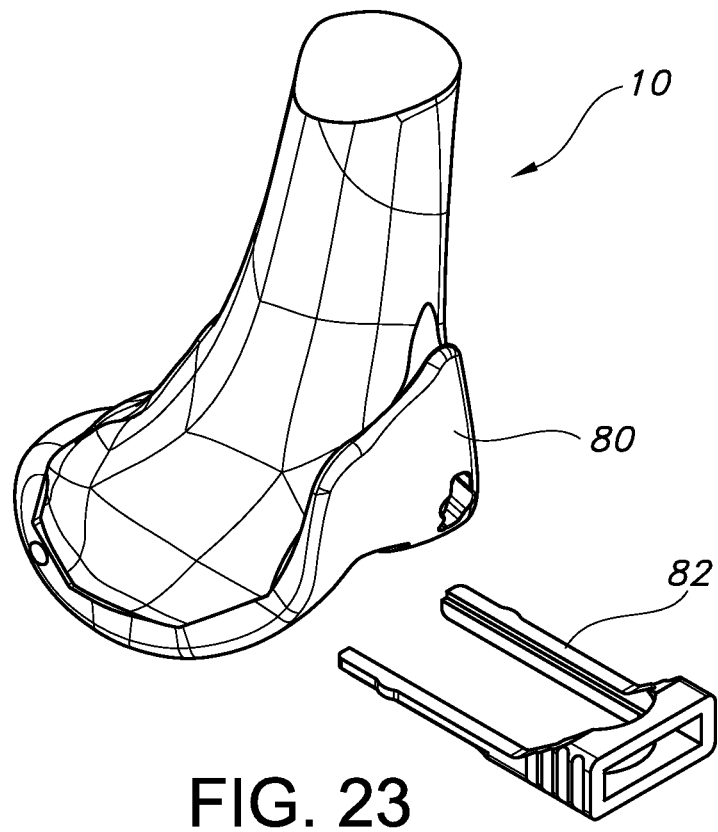
Figure 24:
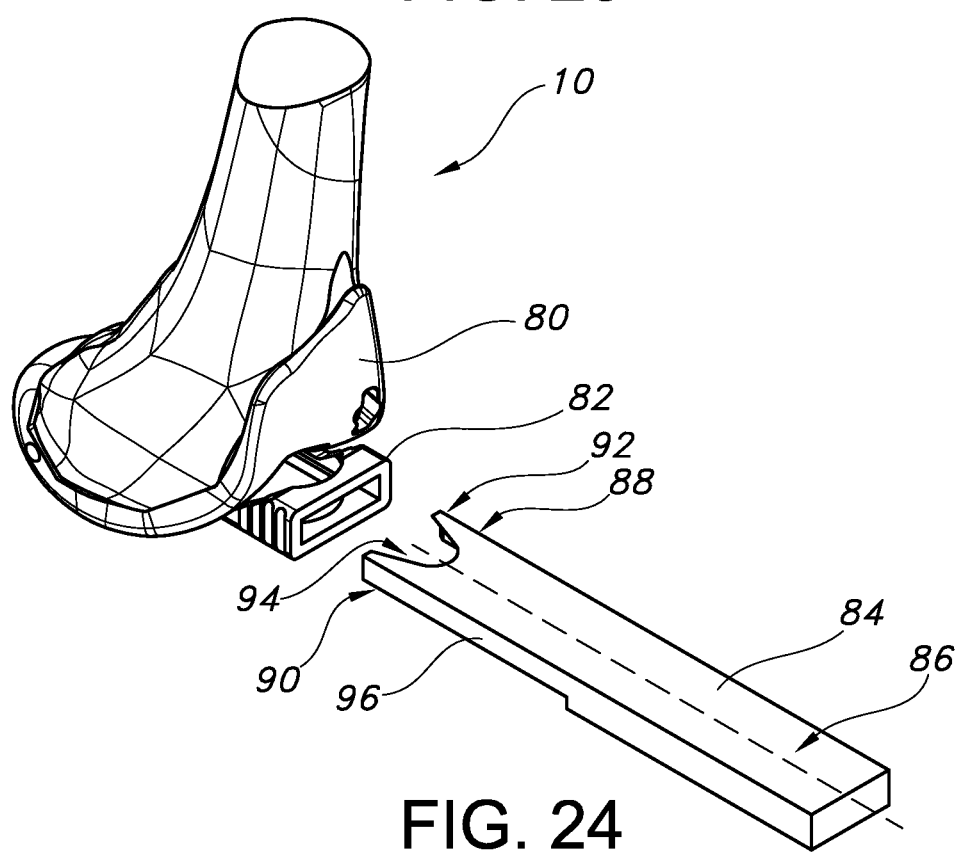
Figure 25:
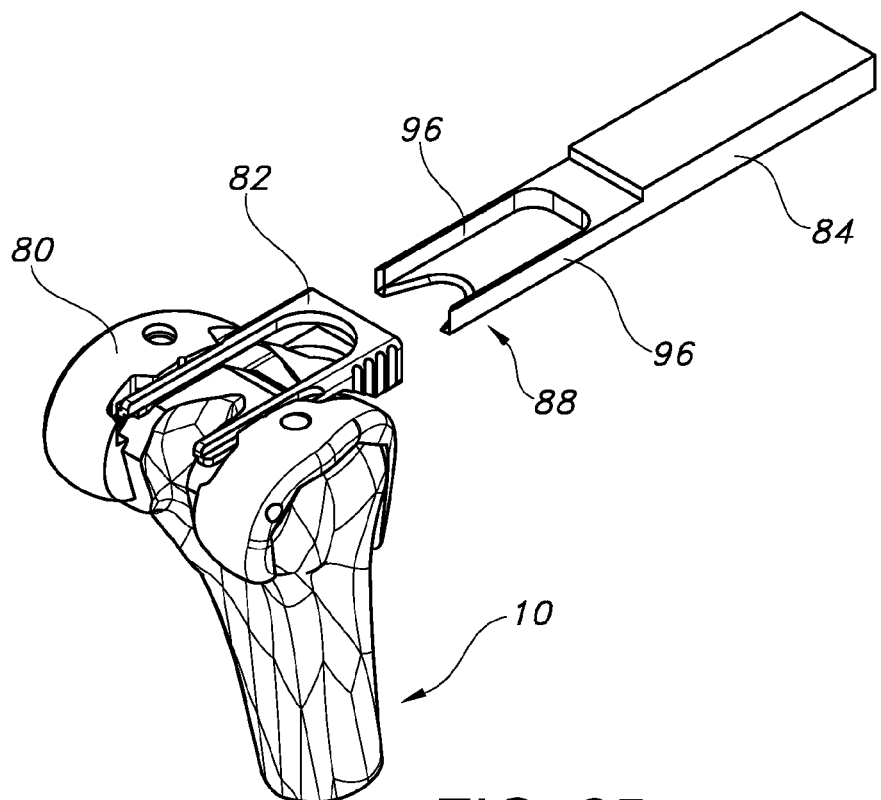
Figures 26A, 26B:
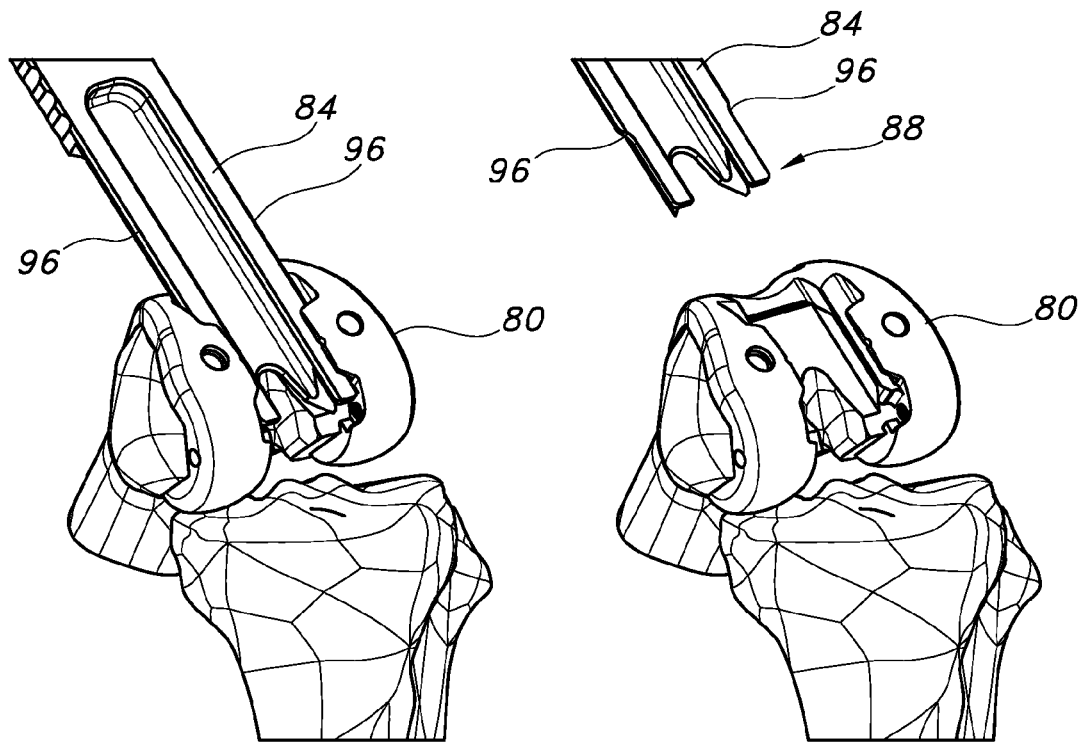

In the embodiment shown in FIGS. 23 through 25, the femoral trial 80 and component 82 are used in combination with the notched cutter 84 to remove a distal sulcus portion of the distal femur 10 adjacent to the ACL and PCL. FIGS. 26 through 28 show a femoral trial 80 with an integral femoral cutting guide used with a notched cutter 84. The notched cutter 84 shown in the Figures is an elongated chisel that extends along longitudinal axis 86 (see, e.g., FIG. 24) and includes a leading cutting edge 88. The leading cutting edge 88 has a medial portion 90, lateral portion 92 and a central portion 94 between the medial and lateral portion. The central portion 94 is substantially recessed into the notched cutter, which, in some embodiments may lower the force required to cut the distal sulcus portion while also lowering the chance that the anterior or posterior ligaments could be damaged during the resection (see, e.g. FIG. 28). The notched cutters 84 shown in the Figures form a U or V shaped leading cutting edge, although other shapes are also possible.

The notched cutters 84 shown in the Figures include flanges 96 that extend substantially parallel to the cutter's longitudinal axis 86. The flanges 96 may interact with channels, grooves or other structures on either the femoral trial 80 or the separate component 82 to guide and/or limit the movement of the notched cutter 84 along the longitudinal axis. In some embodiments, tips of the flanges and/or structures incorporated into the femoral trial 80 or the separate component 82 act to limit the longitudinal movement to prevent the notched cutter 84 from cutting too deeply.

Figure 29:
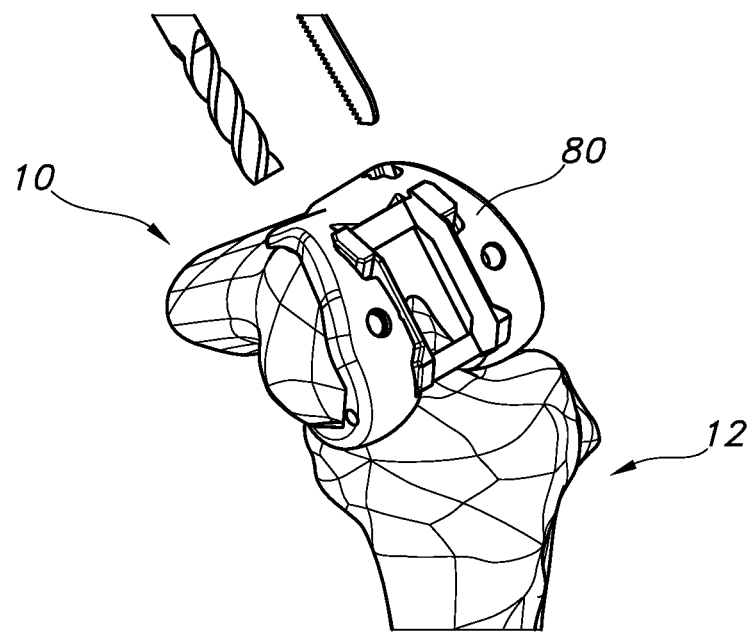

FIG. 29 illustrates that other types of cutters and cutting guides can be used to cut the distal sulcus portion. FIG. 30 shows the distal femur 10 once all of the resections described above have been made.

Tibial Resections

One problem faced when performing bicruciate-retaining TKA procedures that is of potential significance to at least some of the embodiments described herein is the complexity of the tibial resections. This complexity stems from at least two factors, relating to the preservation of the cruciate ligaments.

A first factor is that there are more important degrees of freedom relating to bicruciate-retaining arthroplasty procedures than for typical posterior-stabilized or PCL-retaining arthroplasty procedures. For instance, in total knee arthroplasty, objects such as resection guides and other instrumentation in three-dimensional space have 6 degrees of freedom, including three translational degrees of freedom and three rotational degrees of freedom. At least three additional variables or "forms" may also apply in TKA procedures, including femoral implant size, tibial implant size, and tibial insert thickness. For a posterior-stabilized or cruciate-retaining arthroplasty procedure, only three degrees of freedom (1 translational and 2 rotational) are usually considered important. For many, although not necessarily all, bicruciate-retaining arthroplasty procedures, there are at least three additional degrees of freedom which are considered important (i.e., 1 translational, 1 rotational, and 1 "form"). These three additional degrees of freedom arise due to constraints imposed by preservation of the eminence to which the cruciate ligaments are attached.

A second factor of potential relevance is that bicruciate retaining knee arthroplasty requires precise surgical technique. The trade off with a bicruciate-retaining technique is that of an increased risk of mechanical complications such as stiffness or implant loosening due to the complexity of the surgery, in exchange for healthier postoperative patient mobility and function. The additional degrees of freedom necessary to perform successful bicruciate-retaining procedures demand a greater degree of accuracy than conventional posterior stabilized or posterior cruciate retaining total knee arthroplasty.

Properly controlling and managing the abovementioned degrees of freedom and other factors during surgery is one of the keys to a clinically and commercially successful bicruciate retaining arthroplasty. Clinical success often depends on the ability of a surgeon to accurately and properly implant a well-designed prosthesis in order to achieve the advantages provided by the well-designed prosthesis. Commercial success often depends on the ability of the surgeon to accurately and properly implant a well-designed prosthesis with confidence and speed. Some, although not necessarily all, of the embodiments described herein address these concerns.

As stated previously, of all knee arthroplasty procedures, the risks associated with tibial resection degrees of freedom (i.e., varus/valgus angle, posterior slope angle, and resection depth) are greater for bicruciate-retaining arthroplasty procedures than for posterior-stabilized or posterior cruciate-retaining procedures. This is because varus/valgus angle, posterior slope angle, and resection depth directly affect the operation of the cruciates in guiding joint motion. Moreover, as stated previously, the risks associated with the additional degrees of freedom specific to bicruciate retaining arthroplasty (particularly, internal/external rotation angle and medial/lateral position of the tibial plateau and eminence resections) can include severe penalties for error, including, but not limited to compromised structural integrity of the tibial eminence, compromised joint motion, and/or compromised cortical rim coverage. Errors associated with any of the 5 degrees of freedom associated with a bicruciate retaining procedure may present a surgeon with complex judgment decisions (such as to favor achieving the best possible cortical coverage over providing maximum preservation of the tibial eminence and its anterior and posterior cruciate ligament attachment sites). Such judgment decisions may be for instance, whether or not to re-cut a bone to correct a perceived error, or to simply let the error remain. Re-cutting decisions contribute to an increase in both time and complexity, and may subsequently increase the likelihood of propagating further errors.

Embodiments of the bicruciate retaining total knee arthroplasty techniques and instrumentation described herein presents to surgeons a truly complex surgery in a simplified format through thoughtful organization, reduction and readily available information. As will be discussed hereinafter, these embodiments may provide, in part, an improved method of preparing a proximal tibia during total knee arthroplasty and apparatus thereof. The methodologies and apparatus described below can be generally divided into three stages: controlling degrees of freedom; making resections; and then performing finishing steps.

Controlling degrees of freedom can generally include one or more of the steps of: roughly setting tibial resection depth, setting a neutral (or reference) varus/valgus angle for the medial and lateral tibial plateau resections, setting a neutral (or reference) posterior slope for the medial and lateral tibial plateau resections, fine-tuning the posterior slope angle and/or varus/valgus angle for the medial and lateral tibial plateau resections, setting medial-lateral positioning of the medial and lateral eminence bone cuts, setting an internal-external rotation angle for the medial and lateral eminence bone cuts, if desirable, determining an appropriately-sized tibial eminence width (related to implant size), and fine tuning the depth for both the medial and lateral tibial plateau resections.

Making resections can generally include one or more of the steps of: making a medial tibial plateau resection, making medial and lateral tibial eminence bone cuts, performing a medial plateau balance check, performing a lateral tibial plateau resection, and performing a trial reduction to assess range of motion, joint stability, and soft tissue tension.

Finishing steps can also generally include one or more of the steps of: punching a keel cavity into the cancellous bone of the proximal tibia, and making an anterior eminence bone cut and an anterior tibial plateau resection to remove an anterior block portion of the tibial eminence, removing bone at eminence corners, and implanting a tibial component.

1. Controlling Degrees of Freedom

This section begins by introducing some of the instruments and other apparatus and describing some aspects of their structure and design that are used to control tibial degrees of freedom in accordance with some of the knee arthroplasty methodologies discussed herein. Later parts of this section discuss non-limiting examples of how those instruments and other apparatus are used to control tibial degrees of freedom.

a. Alignment Block

FIGS. 34a through 34g show various views of an alignment block 102 that can be used, in some embodiments, as a fundamental instrument to provide such a neutral/reference tibial foundation. The alignment block 102 includes a body 106 through which several pin receiving openings 108 extend for pining the alignment block 102 to the proximal tibia 12. The alignment block 102 also includes a bench 110 with a bench connector 112 positioned superiorly on the body 106. The bench connector 112 shown in FIGS. 34a through 34g is substantially planar, and, as shown particularly in FIGS. 34a and 34c, includes a plurality of index features 116, the purpose of which will be described further below.

Figure 35:
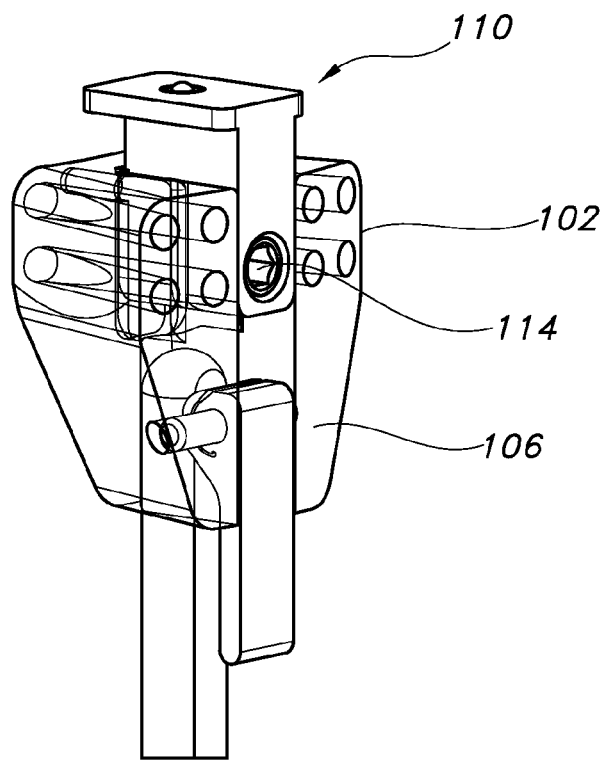
FIGS. 35 and 36 show another embodiment of an alignment block.
Figure 36:
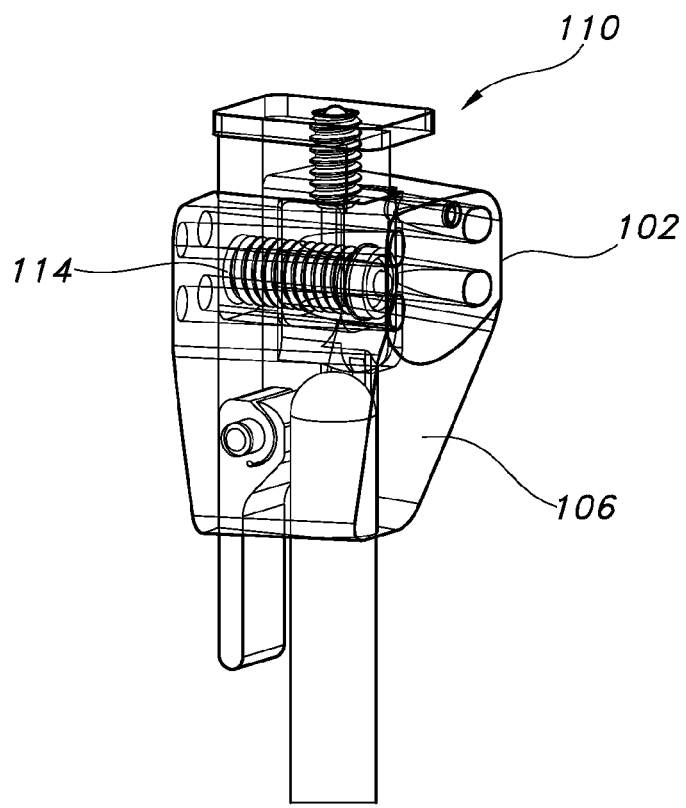

The alignment block 102 shown in FIGS. 34a through 34g, particularly as shown in FIGS. 34d through 34f, allows adjustment of the bench connector 112 in superior and/or inferior directions relative to the proximal tibia 12. As shown in FIGS. 35 and 36 (which show a somewhat different embodiment of the alignment block 102) the alignment block 102 may include a set screw 114 that can be loosened or tightened to respectively allow adjustment of the bench 110 in superior and inferior directions. As also shown in FIGS. 35 and 36, portions of the bench 110 can fit into and be guided by grooves or other structures in the body 106 to maintain the alignment of the bench 110 with respect to the body 106 as it slides in superior and inferior directions. In other embodiments, other structures and mechanisms could be employed in addition to or instead of the structures and mechanisms shown in FIGS. 35 and 36 to guide the movement and selectively fix the position of the bench 110 with respect to the body 106.

FIGS. 37 through 39 illustrate apparatus for connecting an extramedullary alignment rod 36 to an alignment block 102. FIGS. 37a through 37e show various views of an extramedullary rod connector 118 that can be temporarily associated with the alignment block 102, such as is shown in the embodiment illustrated in FIG. 38. The extramedullary rod connector 118 includes a slot 120 sized and aligned to receive the planar bench connector 112 of the alignment block 102 and an aperture 124 sized and aligned to receive alignment rod 36, which can be secured in the aperture 124 by thumb screw mechanism 126. The slot 120 includes a spring tensioner 122 that, in addition to or instead of the geometry of the slot 120 itself, helps to hold and maintain the angular alignment of the extramedullary rod connector 118 with respect to the bench connector 112 (i.e. to maintain an alignment of the extramedullary rod connector 118 on the planar bench connector 112 such that an extramedullary rod 36 held by the extramedullary rod connector 118 is substantially perpendicular to the planar bench connector 112).

The geometries and structures of the planar bench connector 112, the slot 120 and/or the spring tensioner 122 allow, in the embodiment shown in FIGS. 37 and 38, the sliding translation and/or rotation of the extramedullary rod connector 118 with respect to the planar bench connector 112 in several degrees of freedom, while maintaining a substantially perpendicular alignment of the extramedullary rod 36 to the planar bench connector 112. In some embodiments, this adjustability of the extramedullary rod 36 with respect to the alignment block 102 may advantageously allow alignment of the extramedullary rod 36 with axes and/or features of the proximal tibia 12 even though the alignment block 102 may be offset from such features. For instance, in some instances it may be desirable to align the extra medullary rod 36 along the longitudinal axis of the tibia at the tubercle of the proximal tibia 12, while offsetting the alignment block 102 from such tubercle.

Alignment blocks and extramedullary rod connectors other than those shown in FIGS. 34 and 37 could also be used with the methodologies and apparatus described herein. For instance, either the extramedullary rod connector 118 shown in FIG. 37 or another type of extramedullary rod connector could be connected at other locations and to other structures on alignment block 102. As another example, FIGS. 35, 36 and 39 illustrate an alignment block with a built-in connector for an extramedullary rod and with a differently shaped bench 110.

In some embodiments, an alignment block and extramedullary rod connector could be a single piece, or a pair of components that function as a single piece, with one or both of the components including structure (such as pin receiving apertures) for securing the alignment block and extramedullary rod assembly to the tibia. In some instances, pin receiving apertures or other securing mechanisms can define elongated slots that allow adjustment in some degrees of freedom while constraining the assembly onto the tibia in other degrees of freedom.

b. Secondary Alignment Block

FIGS. 40a through 40c illustrate an adjustment instrument or secondary alignment block 128 that can be secured to the alignment block 102 shown in FIGS. 34a through 34g. The secondary alignment block 128 includes a first slot 130 and a second slot 132. The first slot 130 is sized and positioned to receive the planar bench connector 112 of the alignment block 102, and, in some embodiments, can be a receiver structure having an alignment axis. The second slot 132 is sized and positioned to connect to a medial tibial resection cutting guide, as discussed below, or, in some embodiments, with additional or other components.

In the embodiments of FIGS. 40a through 40c, both the first and second slots 130 and 132 are associated with spring tensioners 134, which may, in the case of slot 130, facilitate the frictional engagement between slot 130 and the bench connector 112, while still permitting translation and rotation of the secondary alignment block 128 with respect to the alignment block 102 in certain degrees of a freedom, but while maintaining other fixed alignments between the two blocks 102 and 128. A pair of pins 136 extend through at least slot 130, which may, in some embodiments, interact with the index features 116 of the bench connector 112 to help retain a desired position and orientation of the secondary alignment block 128 on the bench connector 112.

Figure 43A:
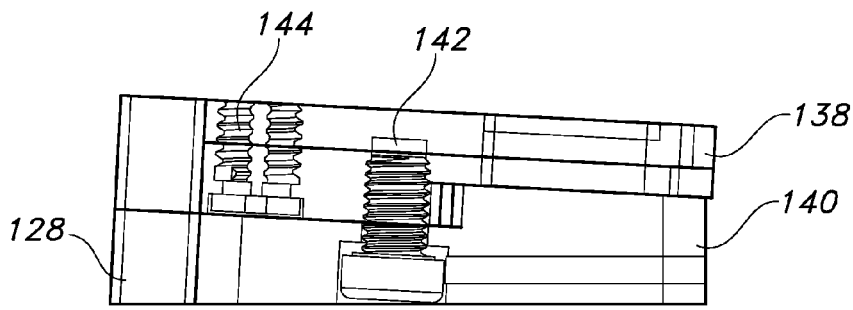
Figure 43B:
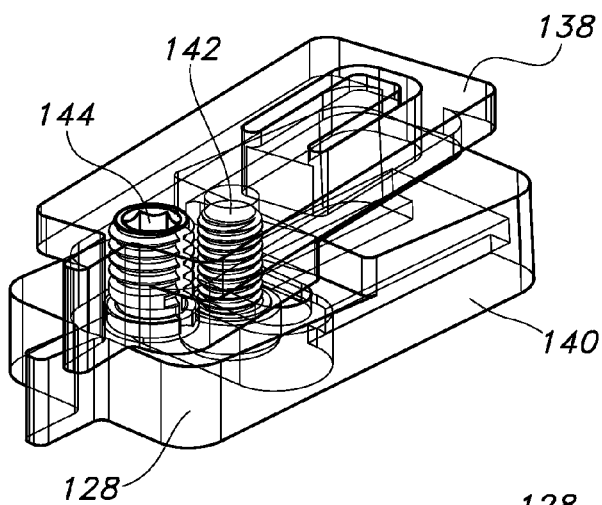

FIGS. 41 through 43 illustrate another embodiment of a secondary alignment block 128 that can be attached to alignment blocks 102, such as ones shown in FIGS. 35, 36 and 39. The secondary alignment block 128 of FIGS. 41 and 42 includes a groove or other structure (not shown) to receive the T-shaped bench connector 112 of the alignment block 102 of FIGS. 35, 36 and 39, which constrains, at least to some degree, the movement of this secondary alignment block 128 with respect to the alignment block 102 of FIGS. 35, 36 and 39. Rather, the secondary alignment bock 128 itself is adjustable in certain degrees of freedom that allow an upper portion 138 to rotate and translate with respect to a lower portion 140 of the secondary alignment block 128 shown in FIGS. 42a through 42c while maintaining the alignment of the two portions in other degrees of freedom. As shown in FIG. 43, this secondary alignment block 128 includes a pivot 142 and a lock 144 to facilitate the rotational and translational adjustment of the upper portion 138 to the lower portion 140, and securing the position and orientation of the upper portion 138 with respect to the lower portion 140 once a desired position and orientation are achieved. The pivot 142, which may be a screw or other mechanism, is positioned in an oblong or oval track in the lower portion 140. The secondary alignment block 128 shown in FIGS. 41 through 43 also includes spring fingers 190 (on superior, inferior or other surfaces) that can, in some embodiments, facilitate frictional engagement between the secondary alignment block 128 and other instrumentation and components, and/or between upper and lower portions 138, 140 of the secondary alignment block 128 itself.

As illustrated by these alternative embodiments, the specific manner in which the secondary alignment block 128 can be translated and rotated with respect to the alignment block 102 is not necessarily important, and a variety of structures and mechanisms can be used to facilitate adjustment in certain degrees of freedom (e.g., without limitation, translation and rotation in a single plane), while preserving other alignments between the alignment block 102 and secondary alignment block 128 (e.g., without limitation, translations and rotations outside of the single plane). The embodiments shown in the Figures create "planar" joints that allow simultaneous and limited medial/lateral translations and internal/external rotations while maintaining other alignments, such as posterior slope angles and superior/inferior positioning. Although the embodiments shown include planar joints defined by a single connection between two components, other structures and mechanisms could also be used to create "virtual" planar joints with similar properties. The purpose of these structures and mechanisms for allowing adjustment in some degrees of freedom (such as medial/lateral position and internal/external rotation), while limiting movement or rotation in other degrees of freedom, will be described further below.

Returning to the embodiment shown in FIGS. 40c through 40e, slots 130 and 132 extend through the secondary alignment block 128 at fixed angles to one another, and the secondary alignment block 128 may be part of a set of secondary alignment blocks 128 having different fixed angles between the two slots 130 and 132 (e.g. 0 degrees, 3 degrees, 5 degrees), with such fixed angles being marked on the secondary alignment blocks 128 such that the surgeon and assistants can differentiate between the various blocks 128. As will be described further below, the different fixed angles allow the surgeon to a select a desired fixed posterior slope for the plateau resections on the proximal tibia 12. Although not shown in the Figures, the slot geometry of the secondary alignment blocks, or other features of the secondary alignment blocks, could vary to allow selection of a desired varus/valgus angle, either in addition to or alternatively from the selection of a desired posterior slope angle.

The secondary alignment blocks 128 shown in FIGS. 40c through 40e limit control of posterior slope angle to only a few discrete, limited options which are mutable without the need for re-cutting in order to provide accurate and reproducible bone cuts with conventional surgical saw blades and other cutting blocks.

Figure 44B:
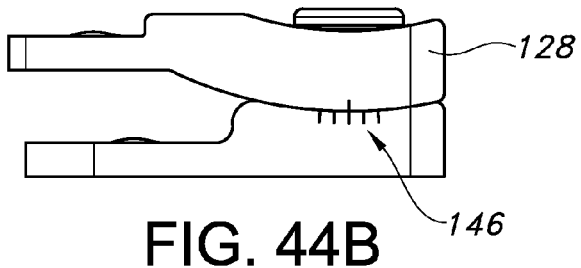
FIGS. 44a through 44c show another embodiment of a secondary alignment block.
Figure 44C:
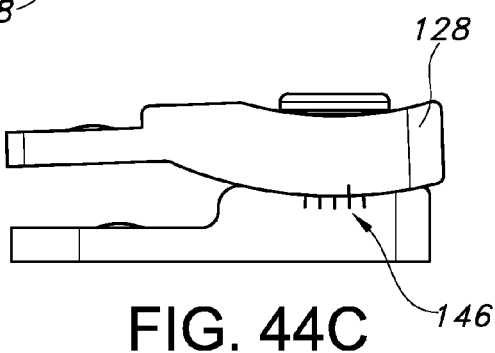
Figure 44A:
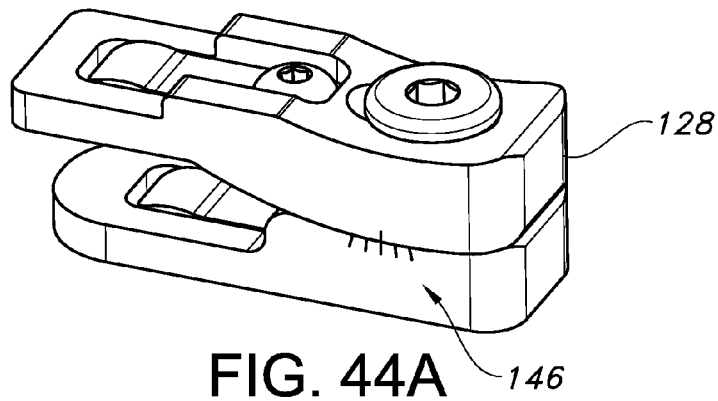

However, it is envisaged that secondary alignment blocks 128 could be provided with means for incrementally or infinitesimally adjusting a posterior slope angle. FIGS. 44a through 44c illustrate an embodiment of a secondary alignment block 128 that can adjust the posterior slope angle. Such embodiments may comprise indicia 146 on upper, lower, and/or side portions of transverse alignment block to provide the surgeon with information relating to small changes in posterior slope angle. Indicia may comprise, without limitation, a series of markings, grooves, laser etchings, colored bands, printed symbols, and lines. The upper and lower portions of the secondary alignment block 128 shown in FIGS. 44a through 44c are curved to allow the portions to rotate with respect to one another, thereby adjusting the posterior slope angle of the alignment block. A set screw or other appropriate mechanism may be included to secure the secondary alignment block in a desired posterior slope.

It is believed that with time and experience with the disclosed bicruciate-retaining surgical technique, surgeons will begin to appreciate the limited number of options for setting posterior slope angle, and prefer a particular posterior slope angle for all procedures based on whatever philosophies he or she adopts and his or her own observations.

c. Medial Tibial Resection Cutting Guide

FIGS. 45a through 45c illustrate an embodiment of a medial tibial resection guide 148 for attachment to a secondary alignment block 128, such as the secondary alignment blocks 128 shown in FIGS. 40a through 40e. The medial tibial resection guide 148 shown in these Figures includes a central body portion 150 that is configured to be a support connection that will connect the medial tibial resection guide 148 to a correspondingly shaped connection feature or features on a secondary alignment block 128. In the specific example of the secondary alignment blocks 128 shown in FIGS. 40a through 40e and the medial tibial resection cutting guide 148 shown in FIGS. 45a through 45c, the second slot 132 of the secondary alignment block 128 receives a lower portion of the central body portion 150, and a slot 152 receives the portion of the secondary alignment block 128 positioned superior to the second slot 132. The interaction between these structures and slots on the two components may, in some embodiments, mean that the position and orientation of the medial tibial resection cutting guide 148, and the structures and components on it, will be constrained, in at least some degrees of freedom, by the position and orientation of the secondary alignment block 128 (such degrees of freedom including, for instance, medial/lateral position, internal/external rotation, posterior slope angle, and tibial depth). The reason for these constraints will be discussed further below.

The medial tibial resection guide 148 shown in FIGS. 45a through 45c includes a medial cutting guide surface 154 for guiding a cutting or milling instrument to resect a medial portion of the proximal tibia 12. As shown in these Figures, the medial cutting guide surface 154 is part of a slot extending through a medial portion of the medial tibial resection guide 148 with superior and inferior surfaces to constrain the movements of a cutter in superior and inferior directions, although, in other embodiments, a single non-capturing cutting guide surface 154 may only be necessary. The medial tibial resection guide 148 of these Figures also includes a medial resection opening 156 and a lateral resection opening 158 for receiving pins to secure the medial tibial resection guide 148 to the proximal tibia and for other purposes described further below. Openings 156 and 158 are oriented in substantially the same direction and angulation as the slot 152, and thus will be oriented in substantially the same direction and angulation as the secondary alignment block 128 shown in FIGS. 40a through 40c when the medial tibial resection guide 148 is connected. As shown in FIG. 45c, a line tangent to the bottom of openings 156 and 158 is generally coplanar with the medial cutting guide surface 154.

Figure 47:
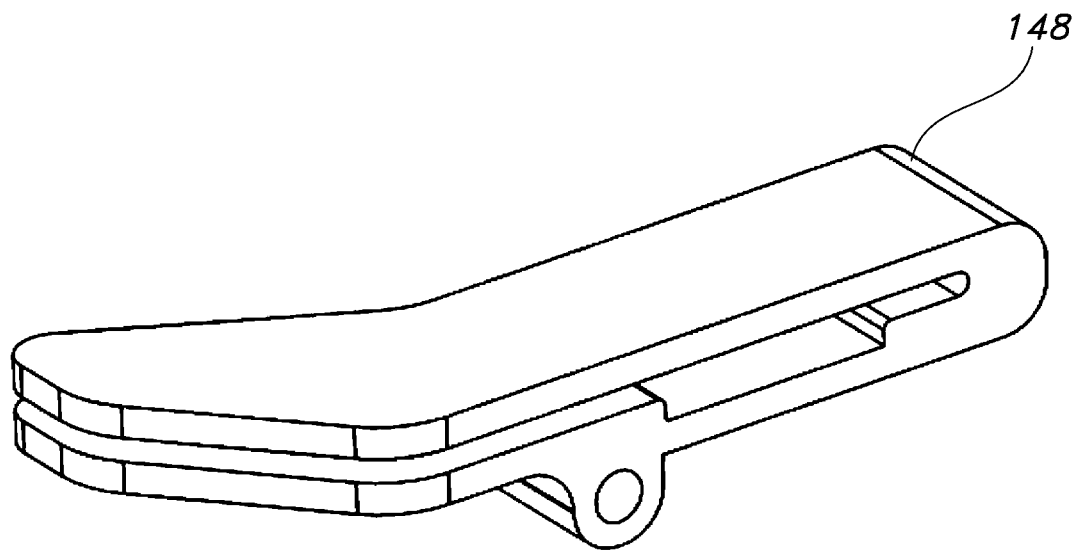
Figure 48:
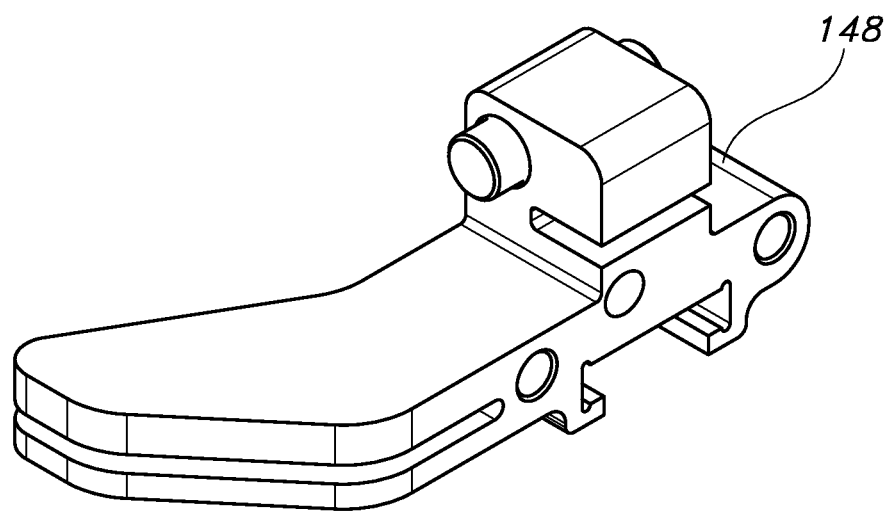

FIGS. 46 through 48 illustrate alternative embodiments of medial tibial resection guides 148. FIG. 46 illustrates a medial tibial resection guide that includes both medial and lateral cutting guide surfaces. FIG. 47 illustrates another possible configuration for a medial tibial resection guide (including that the medial tibial resection guide can be used for lateral resections as well), and that different configurations and positions for the resection openings are possible. FIG. 48 illustrates another possible configuration for a medial tibial resection guide, with different structures for attaching the guide to secondary alignment blocks or other components.

d. Stylus

FIGS. 49a through 49e illustrate a stylus 160 that can be used with many of the methodologies and apparatus described herein. The stylus 160 includes a body 162 for connecting the stylus 160 to other instrumentation, such as, but not limited to, the medial tibial resection guide 148 shown in FIG. 45a. In this particular embodiment, a slot 164 (with a spring tensioner positioned therein) in the stylus body 162 is configured to receive a portion of the medial tibial resection guide 148 shown in FIG. 45a, with an inferior portion 166 of the stylus body 162 protruding into the slot 152 of the medial tibial resection guide 148. In such an embodiment, as illustrated by, for example, FIG. 74, both portions of the stylus body 162 and portions of the secondary alignment block 128 protrude into the slot 152 of the medial tibial resection guide 148, creating a single assembly in which these components are in fixed positions (in at least some translational and rotational degrees of freedom) with respect to one another and can be translated and/or rotated in at least some degrees of freedom simultaneously. As shown by the Figures and as will be appreciated by one of skill in the art, other connector constructs are also possible to create similar or other assemblies of alignment blocks, cutting guides and styli. As described in further detail below, various stylus embodiments can also be connected to other instrumentation, trials, other apparatus, or anatomy relevant to knee arthroplasty procedures other than just alignment blocks and cutting guides.

As shown in FIG. 49a, the body 162 of stylus 160 defines a reference plane 168 and a connection axis 170. The stylus 160 shown also includes two indicator members 172 and 174 pivotally mounted to the body 162 (as illustrated by FIGS. 49a through 49e). In some embodiments, the indicator members 172 and 174 can rotate about the connection axis 170 in planes that are substantially parallel to the reference plane 168, although, in other embodiments, the indicator members 172 and 174 can be mounted to the body 162 in fixed orientations and/or in non-parallel orientations. Depending on the particular use of the stylus 160, several uses of which are described below, the indicator members 172 and 174 may function as alignment indicators, cutting guides (e.g. an outer guide surface 176 on one or both of the indicator members 172 and 174), attachment points for other instruments, or for other functions.

As mentioned earlier, three variables that may be specific to bicruciate-retaining surgical procedures are: 1) medial-lateral positioning of the eminence resections, 2) internal-external rotation of the eminence resections, and 3) eminence width. These particular variables can create a large learning curve for surgeons who need to feel comfortable and competent during a surgical procedure.

Figure 52A:
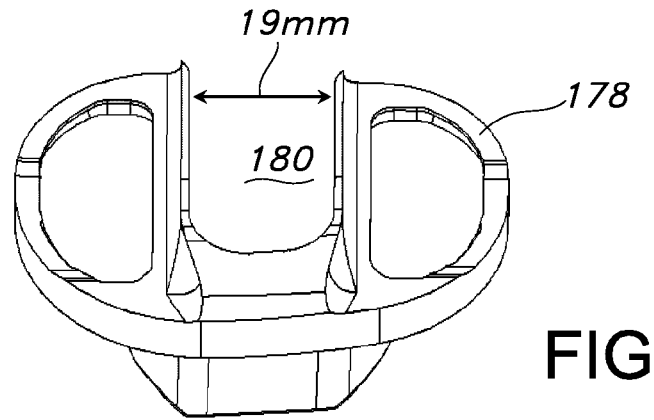
FIGS. 52a and b show two examples of tibial implant baseplates.
Figure 52B:
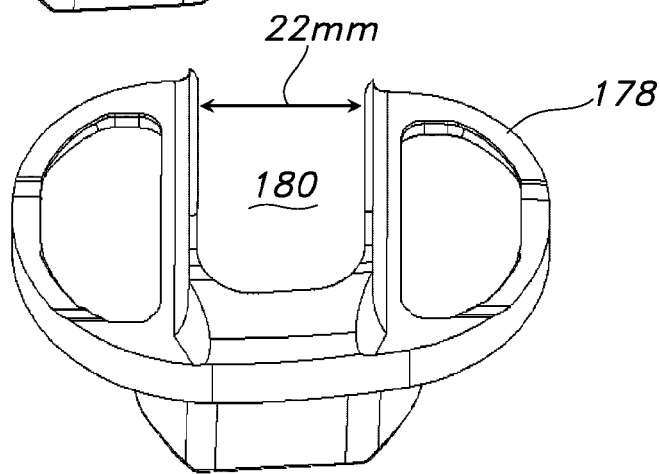

For some of the stylus 160 embodiments discussed herein, degrees of freedom reflected by options for eminence width can be significantly reduced, if not eliminated entirely. Through empirical measurements of the medial-lateral aspect of the anterior cruciate attachment points, it has been determined that that, in some embodiments, the width of the eminence resections may be set at one of two sizes. In some embodiments, the eminence widths of said two sizes may be approximately 19 mm or 22 mm, depending on the size of the tibial implant used (such as is shown in FIGS. 52a and b). Thus, in one example, if a tibial implant to be used in a surgical procedure has a size within a first size range (e.g., sizes 1-6), then a first eminence width is used (e.g., a 19 mm eminence width). In another example, if a tibial implant to be implanted has a size within a second size range (e.g., sizes 7-8) larger than said first size range, then a second larger eminence width is used (e.g., a 22 mm eminence width). It should be noted that more or less than the two sizes and widths other than what is explicitly described are anticipated, as are other widths for each particular size.

In the embodiments shown in the Figures, the indicator members 172 and 174 extend substantially parallel to one another, and define planar surfaces that are substantially parallel to one another as well as to the reference plane 168. In some embodiments, such as the embodiments discussed immediately above, the spacing of the two indicator members 172 and 174 may be defined by the width of a tibial eminence receiving gap 180 on a tibial baseplate 178 (such as the tibial baseplates 178 shown in FIGS. 52a and b). In some embodiments, stylus 160 may include modular indicator members for achieving different spacings between the indicator members to conform to different sizes of tibial baseplates or for other reasons. As yet another alternative, different styli may be provided that include differently spaced indicator members, or having indicator members of different widths. In still other embodiments, the same indicator members can be used to guide saws of different widths simply by using both the inner and outer surfaces of the indicator members 172 and 174.

Figure 51A:
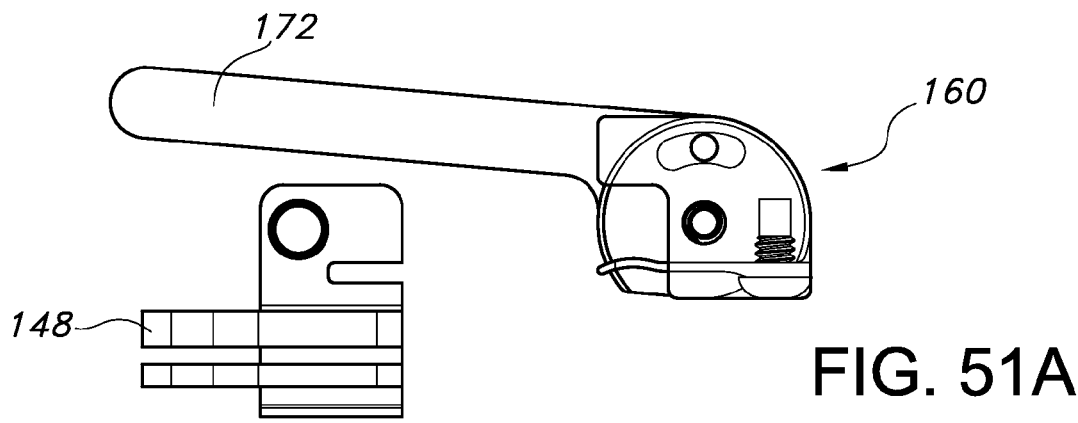
Figure 51B:
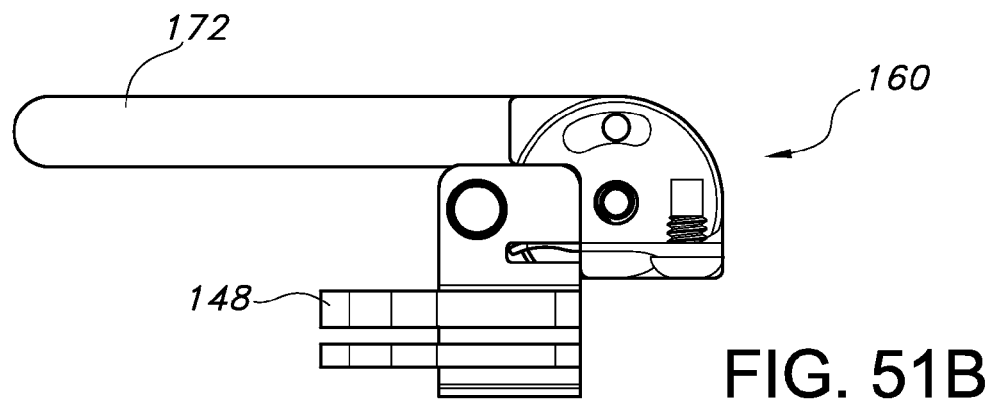

FIGS. 50 and 51 illustrate an alternative embodiment of a stylus 160 with a slightly different configuration and different mechanism for connecting to other components. Other stylus embodiments are also possible. For instance, in some embodiments, indicator members could include captured slots or other structures for capturing, and not just guiding, the movement of a reciprocating cutter or other cutter mechanism.

As discussed further below, various embodiments of styli can be used as alignment and/or cutting guides in a wide variety of configurations, and, in some embodiments, it may be desirable that the connector construct employed by the stylus is such that a single stylus can be connected to a wide variety of different instrumentation, components and other knee arthroplasty apparatus.

e. Positioning the Alignment Block

According to some embodiments, tibial preparation begins by first establishing a neutral/reference tibial foundation from which to begin the procedure. The purpose of providing a neutral tibial foundation early on in the procedure is to roughly set two neutral degrees of freedom (i.e., neutral varus/valgus angle and neutral posterior slope angle) before later fine-tuning and/or setting other degrees of freedom. In some embodiments, the neutral foundation could also roughly set other degrees of freedom, such as resection depth. Providing a neutral tibial foundation generally serves as a good starting point, in at least some embodiments, for subsequent tibial preparation steps. In some embodiments, the step of positioning the alignment block 102 establishes a neutral tibial foundation. As used herein, a "neutral" or "reference" tibial foundation could include foundations set a zero degrees to a particular degree of freedom (such as zero degrees in varus/valgus or zero degrees of posterior slope), but, in some embodiments could also include "non zero" neutral foundations.

Figure 53:
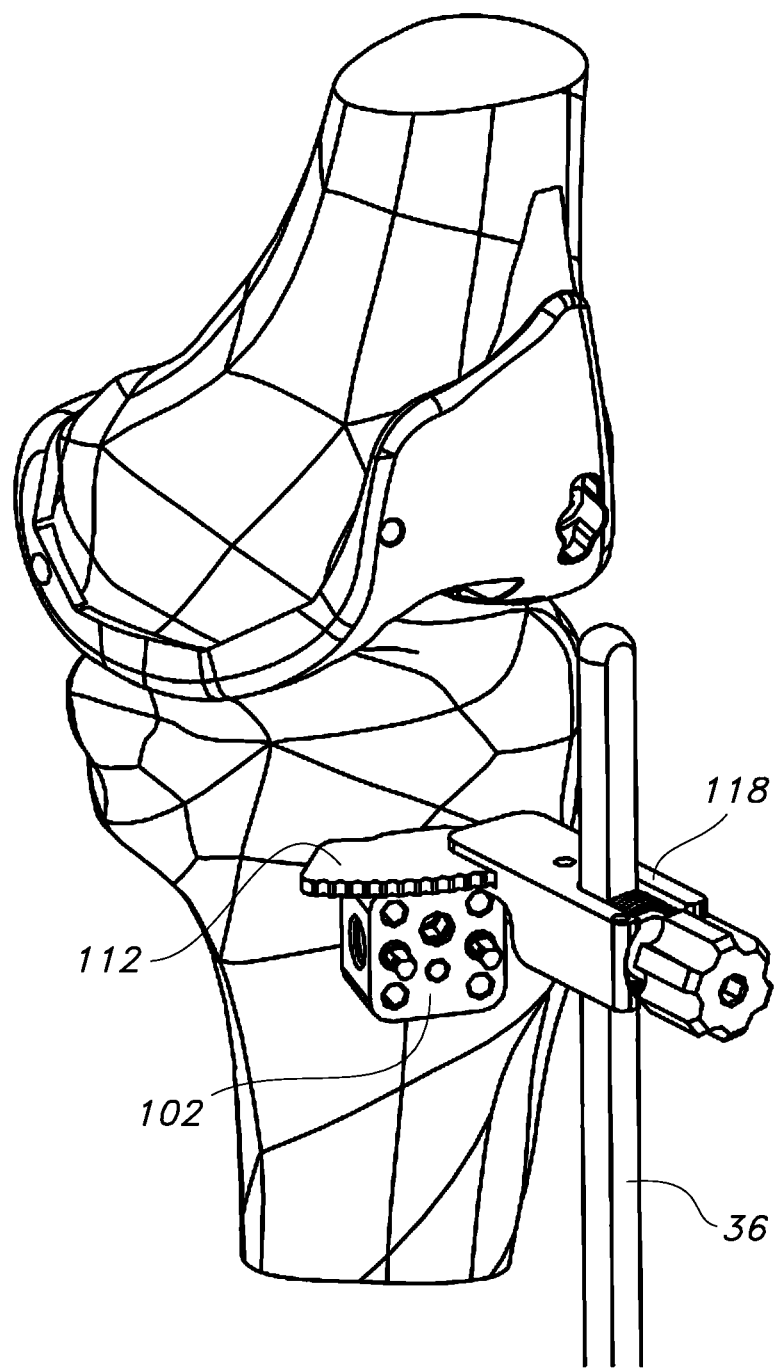
FIGS. 53 and 54 show an alignment block pinned to a proximal tibia, and an extramedullary alignment rod associated with the alignment block by an extramedullary rod connector.
Figure 54:
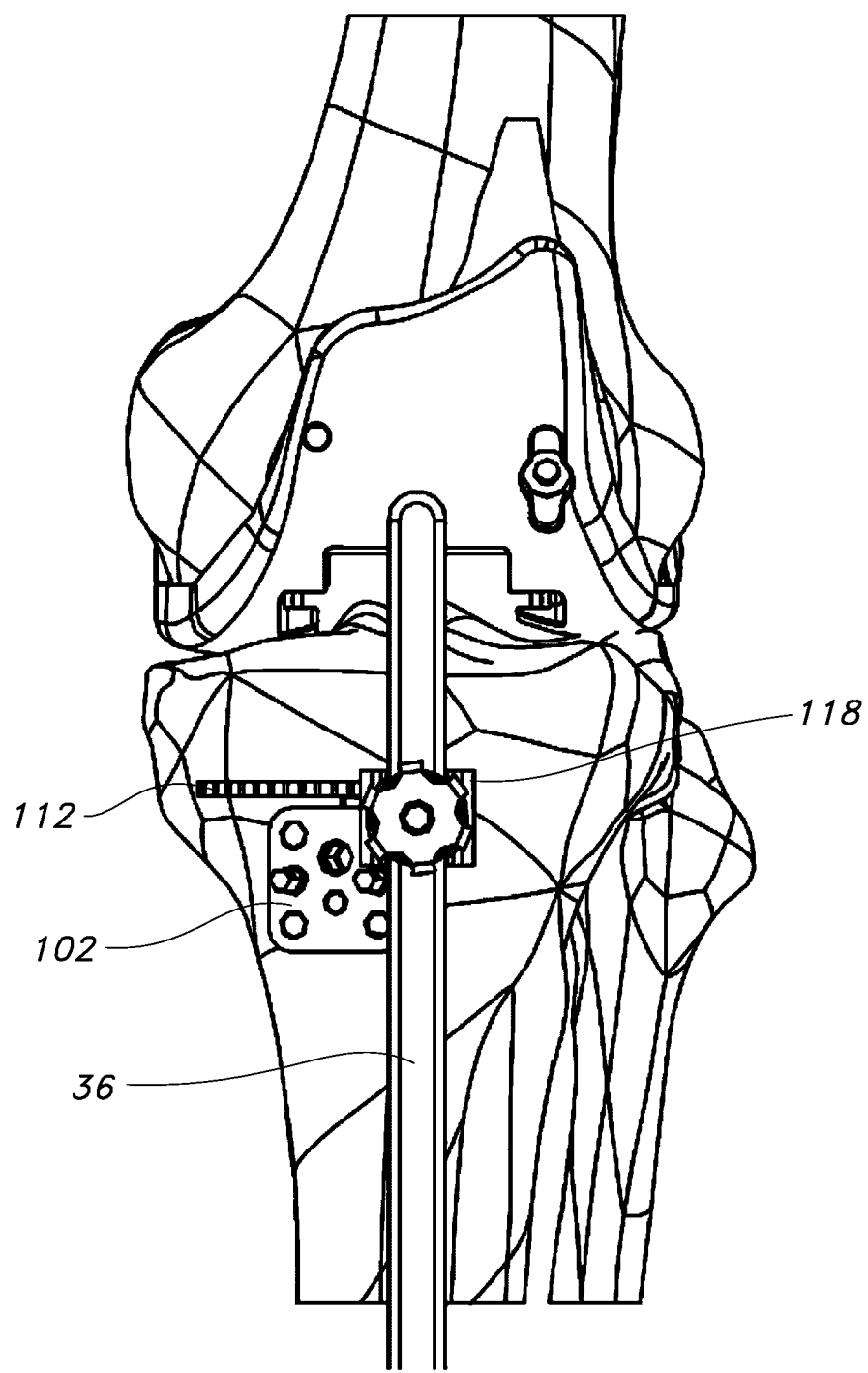

As illustrated by FIGS. 53 through 59, the surgeon can position, orient, and secure in place the alignment block 102 in a wide variety of ways. FIGS. 53 and 54 illustrate the use of an extramedullary alignment rod 36 and an extramedullary rod connector 118 to position and orient the alignment block 102. In this embodiment, the longitudinal axis of the alignment rod 36 may be secured at the patient's ankle and aligned at least roughly parallel to the mechanical axis (in one or both of sagittal and coronal planes) of the tibia at the tibial tubercle or at other locations. Because the connections between the particular extramedullary rod 36, extramedullary rod connector 118, and alignment block 102 embodiments shown in FIGS. 53 and 54 will position the bench connector 112 of the alignment block 102 substantially perpendicular to the longitudinal axis of the alignment rod 36, when the alignment rod 36 is aligned to be roughly parallel to the mechanical axis of the tibia in sagittal and coronal planes, the bench connector 112 will lie in a plane having a zero degree varus/valgus angle and a zero degree posterior slope angle to the tibia. As shown in FIGS. 53 and 54, the connections between these components also allow the alignment block 102 to be offset (in medial or lateral directions) from the tibial tubercle while still aligned in neutral varus/valgus and posterior slope angles. In the embodiment shown in FIGS. 53 and 54, the alignment block 102 is positioned with only a rough (or no) concern for the precise superior/inferior positioning of the alignment block 102 with respect to the tibial plateau, and such positioning can be addressed at a later point in the procedure, such as by slidably adjusting the superior/inferior positioning of the bench connector 112 with respect to the alignment block 102 or repositioning the alignment block 102 itself.

Figure 55:
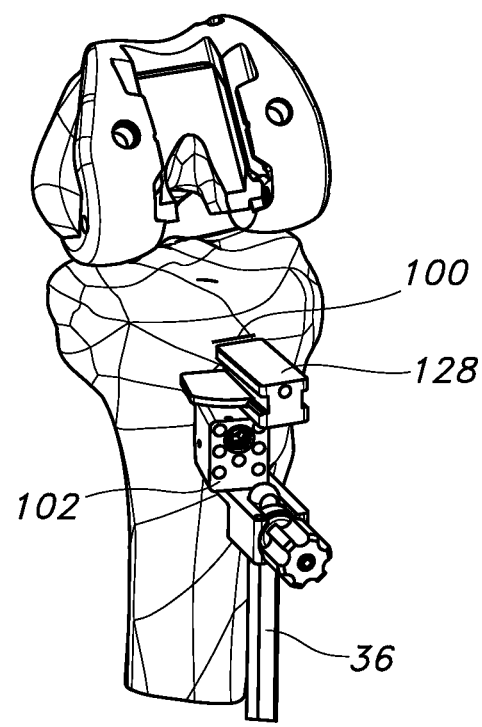
FIGS. 55 through 59 illustrate various methodologies for positioning, re-positioning, adjusting and/or checking the position and/or orientation of various embodiments of alignment blocks on a proximal tibia.

FIG. 55 illustrates an embodiment where the superior/inferior positioning of the alignment block 102 is taken into account at this stage in the procedure. As shown in FIG. 55, the alignment block 102 can be simultaneously associated with both an extramedullary rod 36 and a secondary alignment block 128, with the extramedullary rod 36 facilitating positioning and orienting the alignment block 102 in neutral varus/valgus and posterior slope angles, and the secondary alignment block 128 facilitating positioning the alignment block 102 at a desired superior/inferior position. For instance, in the embodiment shown in FIG. 55, a superior surface of the secondary alignment block 128 can be aligned with indicia 100 to set the alignment block 102 at a desired superior/inferior position on the proximal tibia 12. As discussed above and shown in FIGS. 31 through 33, the position for indicia 100 can be determined in a variety of ways, which may, in some embodiments, correspond to a desired resection depth for the medial and/or lateral tibial plateau resections, or in other embodiments, correspond to a position having a fixed offset from the desired resection depth, both of which may, in some embodiments, be determined based on the level of the distal femoral resection.

Figure 56:
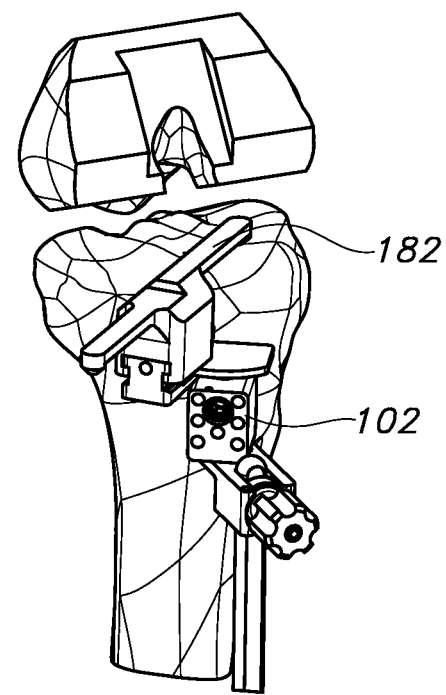
Figure 57:
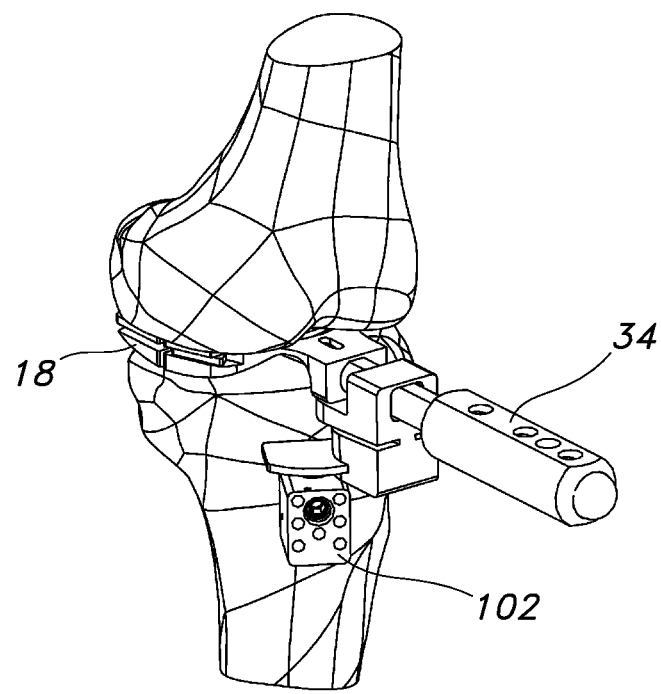
Figure 58:
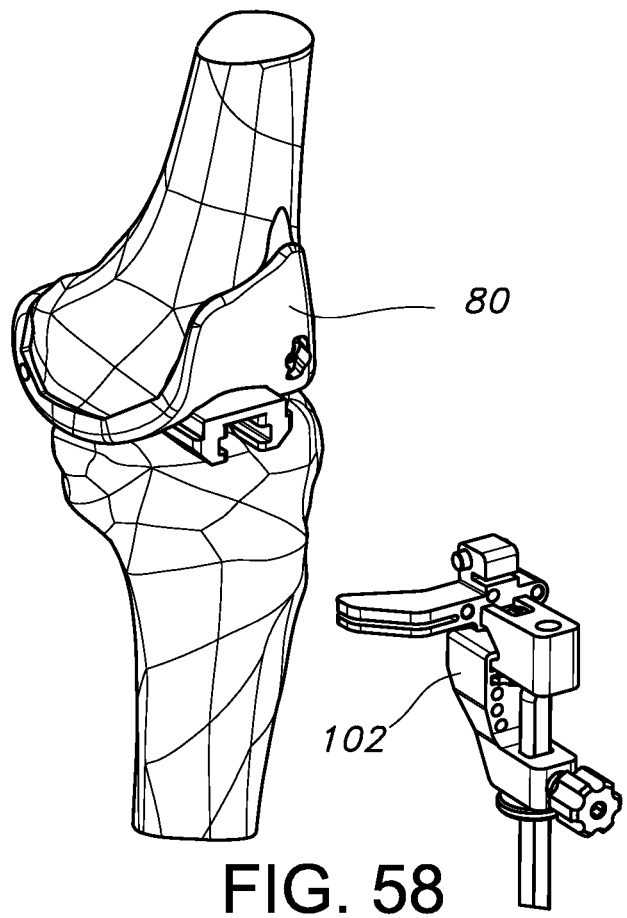

In still other embodiments, such as shown in FIG. 56, a desired superior/inferior position for the alignment block 102 can be set using a stylus 182 that references the level of the tibial plateau or a structure of interest on the tibial plateau. In still other embodiments, such as shown in FIG. 57, a distal femoral trial 18 can be used to position and orient the alignment block 102, at least roughly, at both neutral varus/valgus and posterior slope angles, as well as at a desired superior/inferior position. In such embodiments, it may be desirable (although not required) to use an extramedullary alignment rod 36 (such as by connecting it to the handle 34) to ensure that the alignment block 102 is appropriately positioned, particularly with respect to the posterior slope angle of the alignment block 102, since small angulations in flexion or extension of the distal femoral trial 18 could affect the posterior slope of the associated alignment block 102. FIG. 58 illustrates a similar embodiment, which utilizes a femoral trial 80 to facilitate positioning and/or alignment of the alignment block 102.

Figure 59:
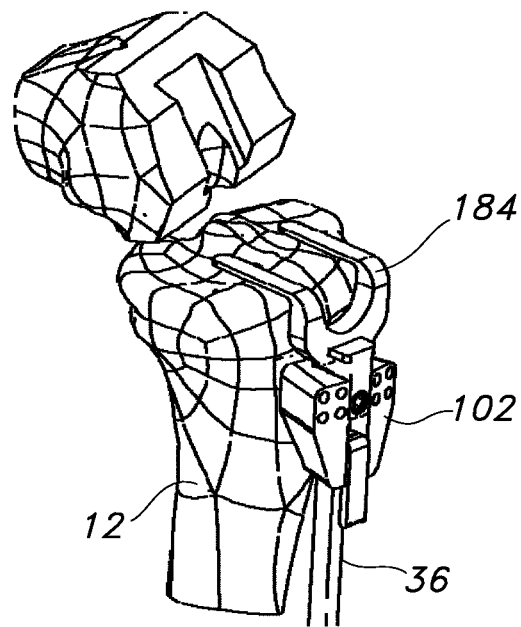

FIG. 59 illustrates another embodiment for aligning an alignment block 102, which utilizes a bi-forked paddle stylus 184 in conjunction with an extramedullary alignment rod 36 to position and orient the alignment block 102. The bi-forked paddle stylus 184 may be placed on a medial and/or lateral portion of the unresected proximal tibial plateau and used as a visual aid in setting a rough medial-lateral position of the alignment block 102 and a rough resection depth. The positioning of the bi-forked paddle stylus 184 and/or the alignment rod 36 with respect to the alignment block 102 and the tibia 12 may be adjusted in order to determine and set the alignment rod 36 and alignment block 102 at a desired neutral varus/valgus angle and neutral posterior slope angle. Once these neutral angles are set, the alignment block 102 may be secured to the alignment rod 36 with a securing means such as a cam and lever (such as illustrated in FIGS. 35, 36 and 39), thumbscrew, setscrew, spring loaded ratchet or detent, or equivalent means provided on the alignment block 102 or a component associated with the alignment block 102. The alignment block 102 may then be secured to an anterior portion of the proximal tibia 12 (e.g., by pinning) and can serve as a neutral tibial foundation for a remainder of the procedure. After the alignment block 102 is pinned to the tibia 12, the bi-forked paddle stylus 184 may be removed from the adjustable portion of the alignment block 102, and the alignment rod 36 may optionally be removed from the alignment block 102, tibia 12, and ankle in order to create more space for the surgeon to work.

f. Positioning the Medial Cutting Block

In some embodiments, the next step in tibial preparation is positioning a medial cutting block (or a combined medial/lateral cutting block) to guide one or more tibial plateau resections and (optionally) vertical eminence resections. In some instances, such as with particular bicruciate retaining tibial implants, degrees of freedom relevant to the medial/lateral position and internal/external rotation of the plateau and/or vertical eminence bone cuts may be highly interrelated, such that, in some embodiments, it may be preferable to set these degrees of freedom simultaneously. In some instances, setting these degrees of freedom individually could be an iterative and time-consuming process.

Figure 60:
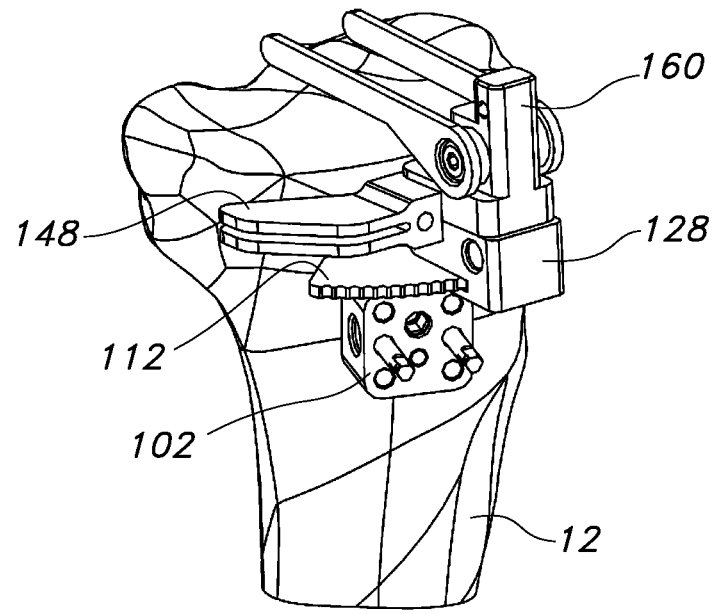
Figure 63:
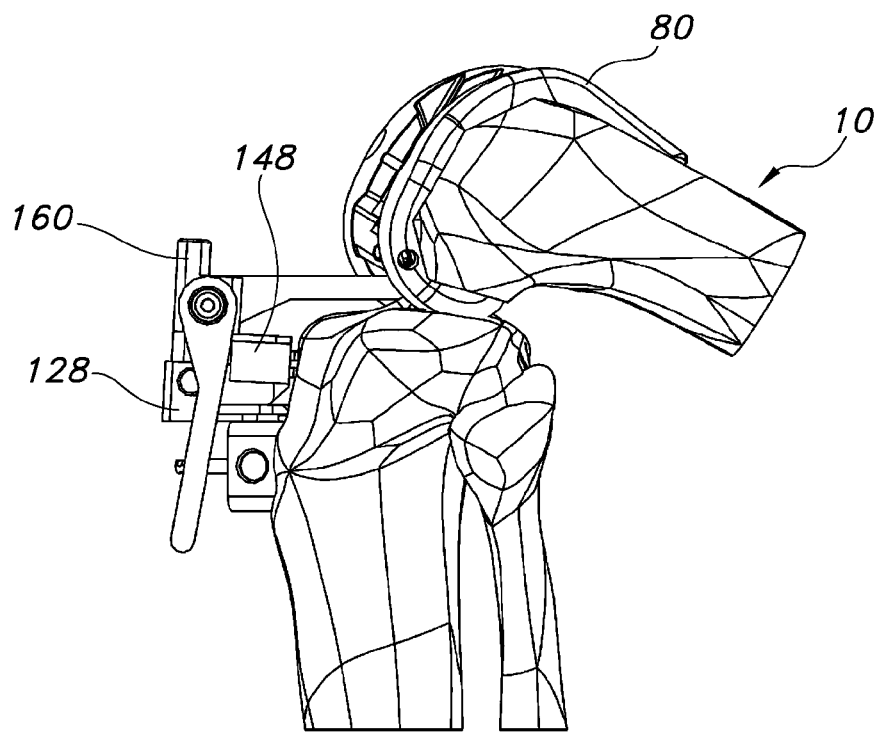
Figure 64:
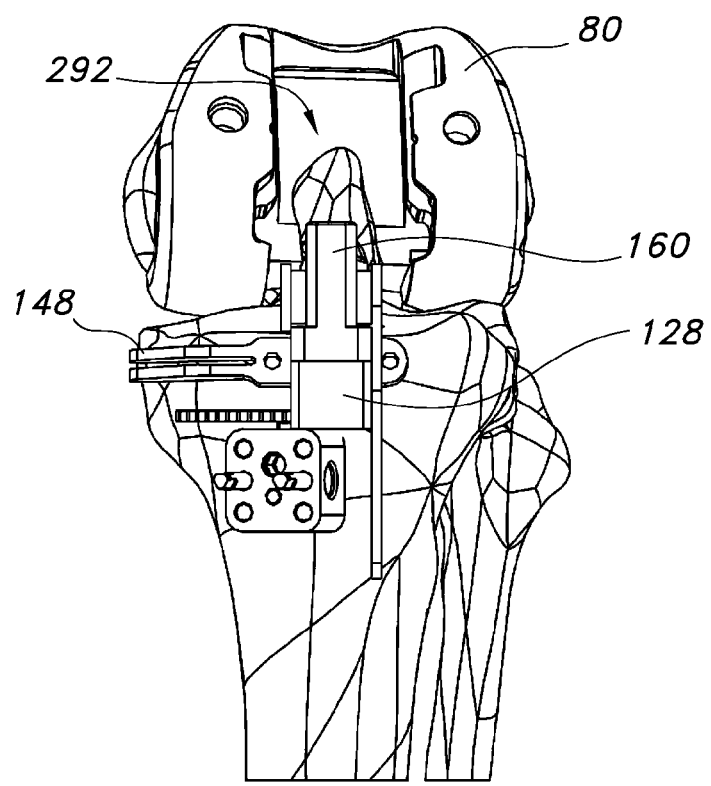
Figure 65:
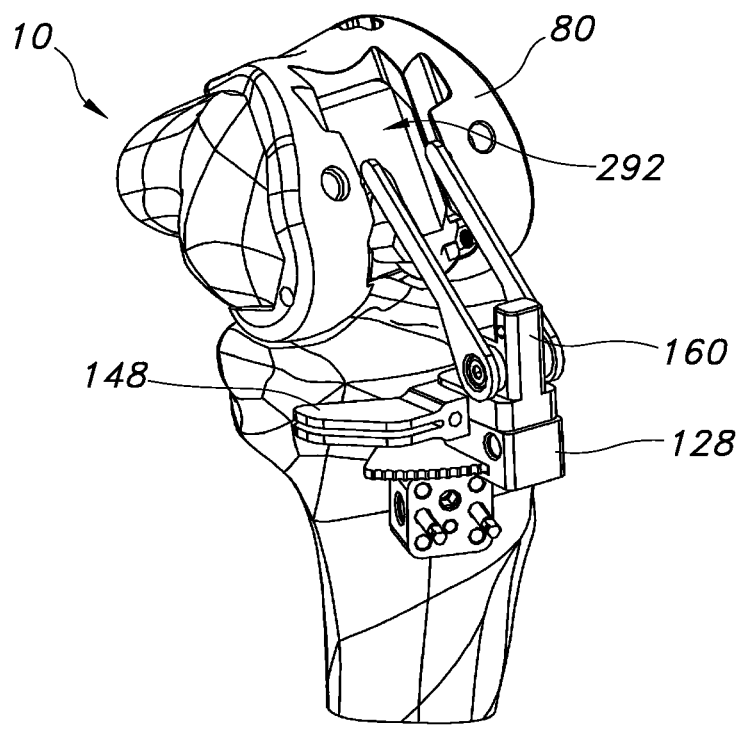
Figure 66:
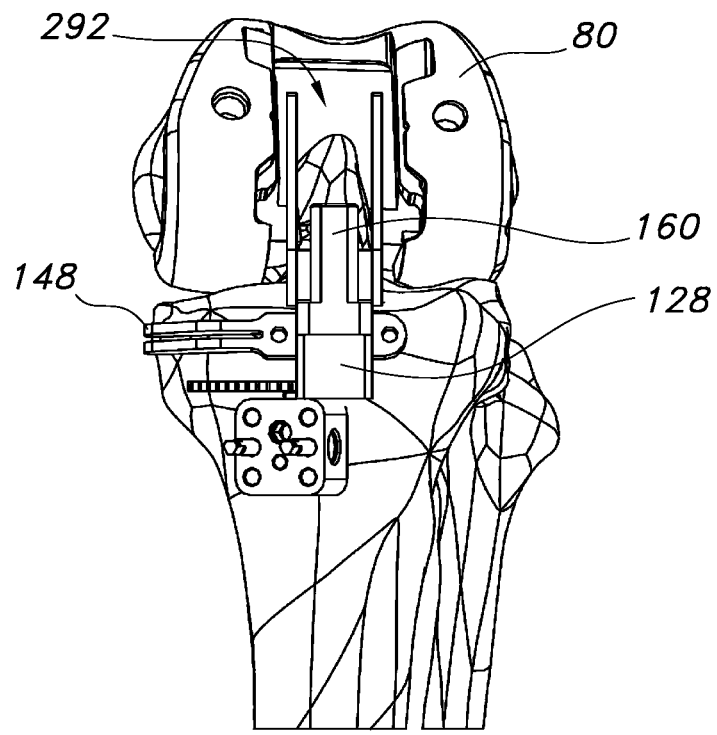
Figure 67:
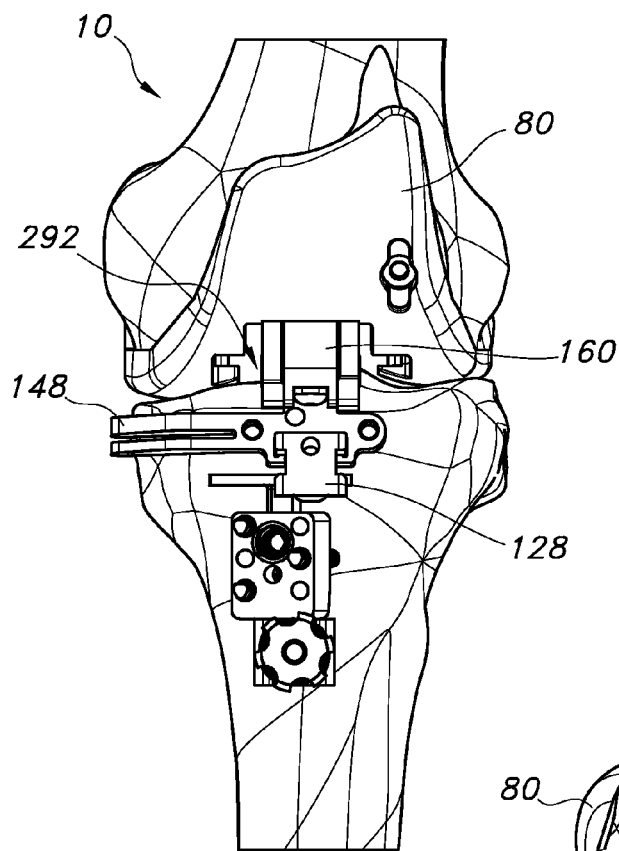

FIG. 60 shows one embodiment of a cutting guide assembly including an alignment block 102 pinned to the proximal tibia, to which a secondary alignment block 128 is mounted, which is in turn connected to a medial tibial resection guide 148 as well as a stylus 160. In this particular embodiment, the orientation of the alignment block 102 pinned to the proximal tibia 12 establishes the varus/valgus alignment of the various resection guides provided by the medial tibial resection guide 148 and the stylus 160. The orientation of the alignment block 102 also establishes, in connection with the particular secondary alignment block 128 chosen the posterior slope angle of the medial tibial resection guide 148. The superior/inferior positioning of the planar bench connector 112 establishes the resection depths for the tibial plateau and vertical eminence resections. As shown, for example, by the various Figures and embodiments described above and below, this is only one example of the many ways the various components described herein could be connected and used to control the various degrees of freedom for the tibial resections.

In the particular embodiment of FIG. 60, the medial/lateral position and the internal/external rotation of the secondary alignment block 128 with respect to the planar bench connector 112 of the alignment block 102 establishes the medial/lateral position and internal/external rotation of the tibial plateau and vertical eminence resections. The planar joint formed by the bench connector 112 and the first slot 130 (see, e.g., FIGS. 40c through 40e) of the secondary alignment block 128 allows the secondary alignment block 128 (and thus the medial tibial resection guide 148 and stylus 160) to be translated and rotated in the plane defined by bench connector 112, such that both the medial/lateral position and internal/external rotation of the secondary alignment block 128/medial tibial resection guide 148/stylus 160 assembly can be adjusted simultaneously, potentially avoiding the need for iterative adjustments of these two degrees of freedom separately from one another. Interactions between the index features 116 (see, e.g., FIG. 34a) on the alignment block 102 and the pins 136 (see, e.g., FIG. 40a) of the secondary alignment block 128, as well as friction between the spring tensioner 134 (see also FIG. 40a) of the secondary alignment block 128 and the planar bench connector 112 of the alignment block 102 may, at least to some extent, facilitate maintaining the position and orientation of the medial tibial resection guide 148/stylus 160/secondary alignment block 128 assembly once placed in a desired position and orientation, prior to pinning the medial tibial resection guide 148 (or other components) to the proximal tibia 12.

As shown in FIGS. 61a through 61d, the indicator members 172, 174 on the stylus 160 can be used while adjusting the position and orientation of the secondary alignment block 128 to visualize the mesial position of the medial and lateral tibial plateau resections, as well as the medial/lateral position and internal/external rotation of the vertical tibial eminence resections (such resections being described further below). This visual feedback to the surgeon may facilitate positioning the medial tibial resection guide 148 and stylus 160 optimally with respect to the tibial eminence 40, the anterior and posterior cruciate ligament attachment sites, and other relevant anatomy.

As shown in FIGS. 62 through 69, stylus 160 can also be used, in some embodiments, to check other alignments and orientations of the anatomy, instrumentation, trials and other apparatus used in knee arthroscopy procedures. For instance, as shown in FIGS. 62 through 69, stylus 160 can be used to visualize alignment with respect to a femoral trial 80 on the distal femur 10, such as, without limitation, various alignments with respect to an intra-condylar notch 292 in the femoral trial 80 (FIGS. 62 through 67) or alignments with respect to a trochlear region 294 formed in an anterior face of the femoral trial 80 (FIGS. 68 through 69), which, as shown in these Figures, may include alignments with respect to an axis of the femur or femoral trial, as illustrated by the vertical lines on the femoral trial 80 shown in FIG. 69. In these embodiments, the stylus 160 is shown connected to a secondary alignment block 128 and a medial tibial resection guide 148, although stylus could be connected to other instrumentation, apparatus or anatomy alternatively. In these embodiments, the stylus 160 is shown being used with the knee joint in various states of flexion and extension.

Figure 68:
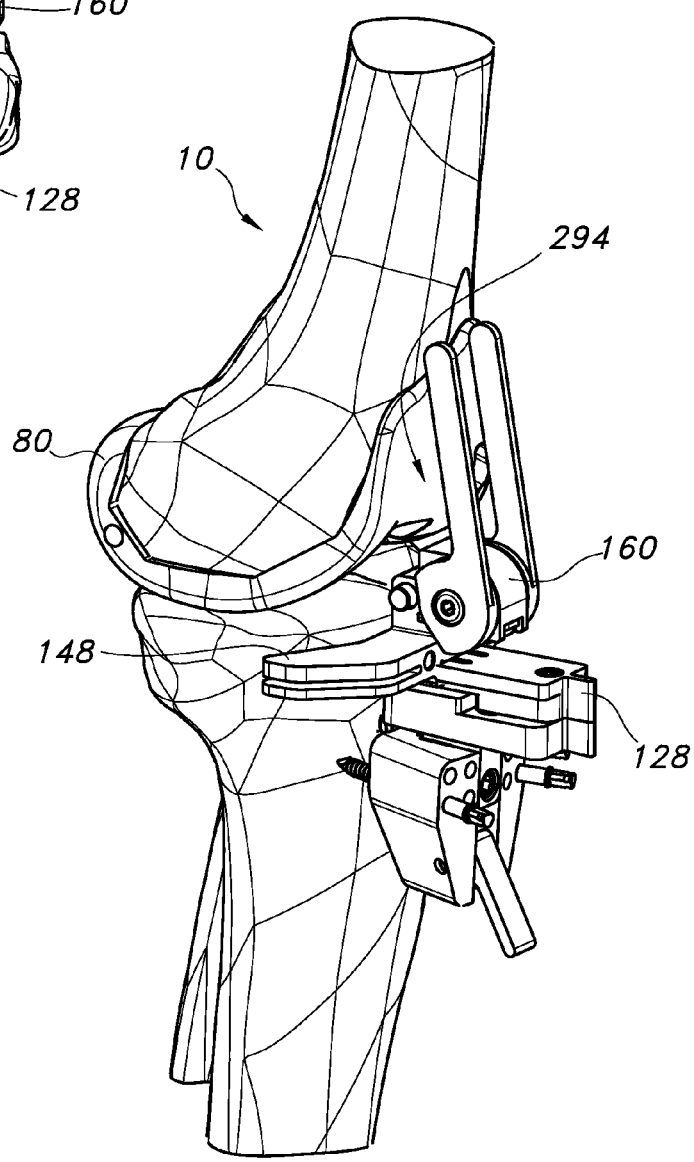
Figure 69:
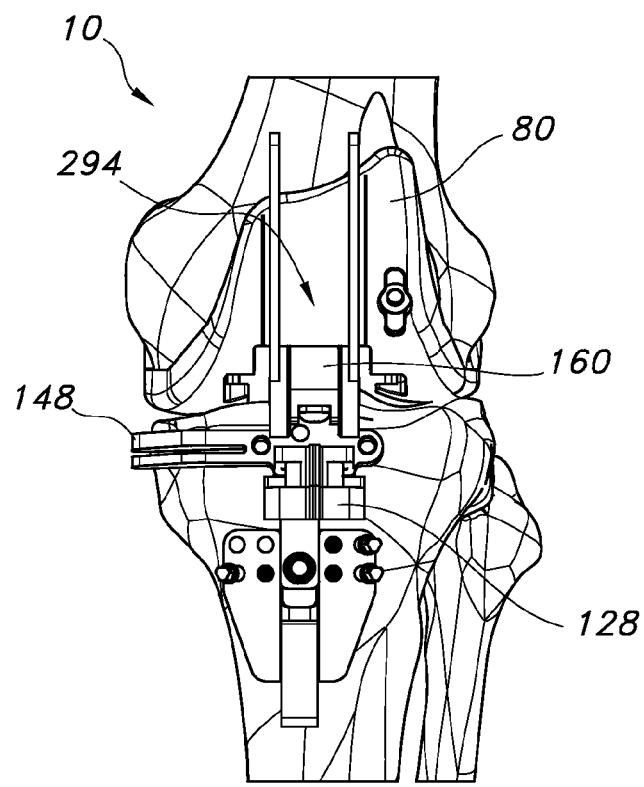

For the embodiments shown in FIGS. 68 and 69, varus/valgus alignment of the femoral trial component relative to the medial plateau resection guide 148 can be assessed by rotating the arms of the stylus 160 upwards, to a vertical position in such a way that they are adjacent to a trochlear region 294 of the femoral trial 80. This step may be performed to verify passive correctability and avoid impingement of the tibial eminence and femoral intercondylar notch. If a surgeon has significant concerns over the peripheral fit of the tibial baseplate on the circumferential cortical rim of the resected tibia, then alternative methods and means for setting medial-lateral positioning and internal/external rotation of the eminence and tibial bone cuts (such as illustrated in FIG. 74) may be preferred.

Figure 71:
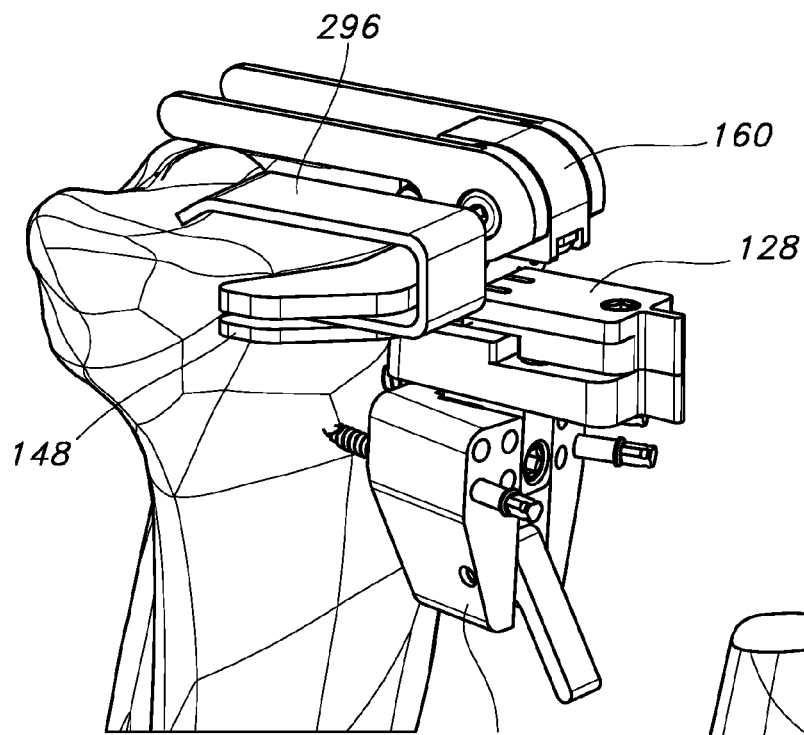

As shown in FIG. 71, resection depth may be checked with an angel wing slot gauge 296 associated with the medial tibial resection guide 148. The angel wing slot gauge 296 is representative of the thickness of a tibial implant. A variety of mechanisms and techniques, as discussed earlier, can be used to roughly set and/or fine tune resection depth.

Figure 70:
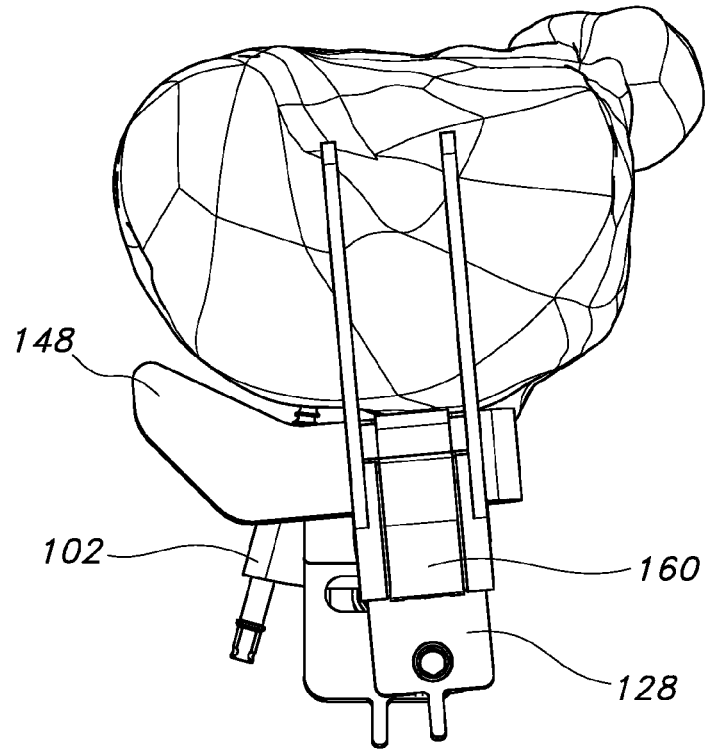
Figure 72:
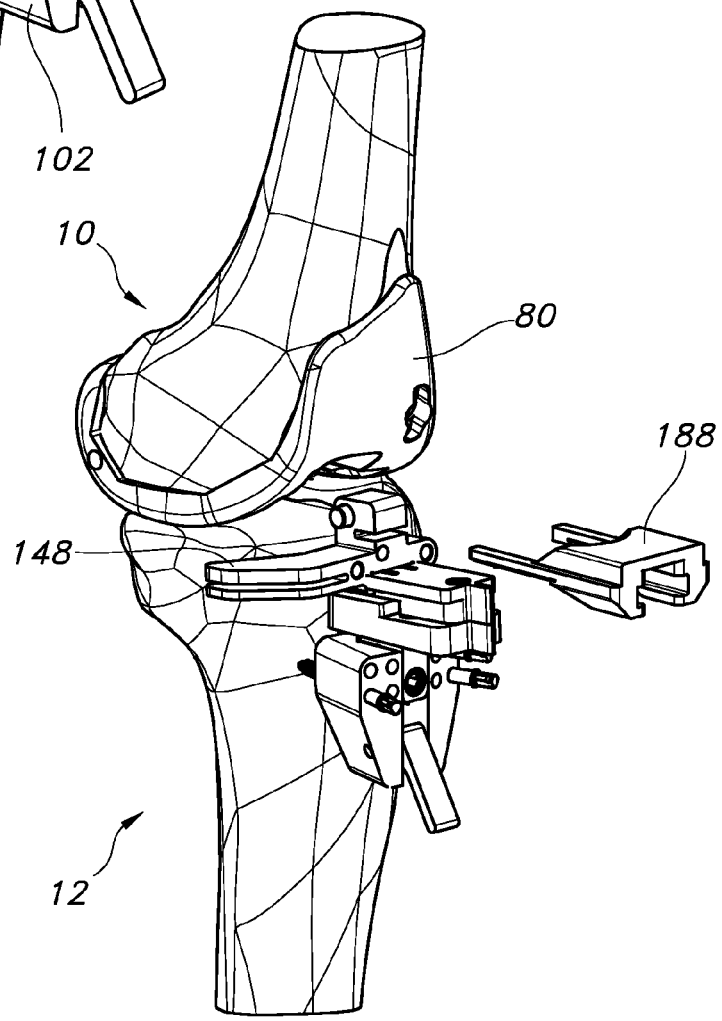
Figure 73:
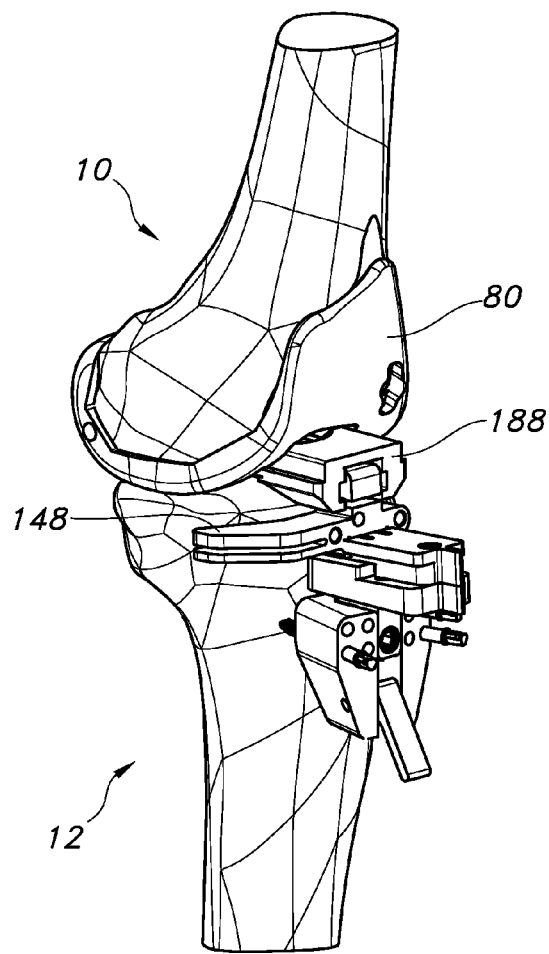
Figure 74:
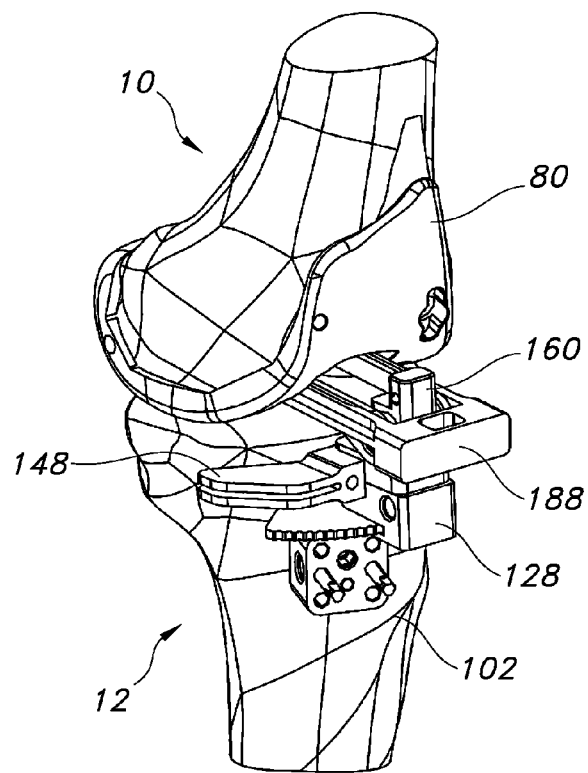

FIGS. 70 through 74 show non-limiting examples of other possible assemblies and methods for positioning the medial tibial resection guide 148 and/or stylus 160 for the tibial plateau and vertical eminence resections. FIGS. 70 and 71 show an assembly utilizing a two piece secondary alignment block 128 (also shown and described in connection with FIGS. 41 through 43) that itself can be adjusted in medial/lateral and internal/external degrees of freedom, rather than moving the entire secondary alignment block 128 with respect to the alignment block 102. FIGS. 72 through 74 illustrate that the position and orientation of the distal femur when in, for instance, extension, can provide reference information that can be used to position and orient the medial tibial resection guide 148 and/or stylus 160. As shown in these Figures, a connector 188 can be inserted (e.g., anteriorly) into a distal receiving portion of the femoral trial 80 to connect one or more of the medial tibial resection guide 148, stylus 160 and secondary alignment block 128 to a femoral trial 80 or other construct positioned on the distal femur 10, which may or may not take into account resected surfaces on the distal femur 10, and, as such, the position of the femoral trial 80 or other construct on the distal femur 10 can be used to position and orient the apparatus used for the proximal tibia 12 resections. In the embodiment shown in FIGS. 72 and 73, cylindrical bosses on the medial tibial resection guide 148 (or, in other embodiments, on the stylus 160) rest within a track of the connector 188. Generally, anterior-posterior translation and flexion/extension angle of the medial/tibial resection guide 148 relative to both the connector 188 and femoral trial 80 are not constrained. However, internal-external rotation and superior-inferior positioning are generally constrained when the medial tibial resection guide 148 is coupled with the connector 188.

In the embodiment reflected by FIGS. 72 and 73, adjustment portions on the secondary alignment block 128 and alignment block 102 may be loosened and tightened in an iterative fashion, so that alignment of the medial tibial resection guide 148 is set in a neutral biomechanical position when the leg is placed in full extension. Once the neutral biomechanical position is set, the adjustment portions on the secondary alignment block 128 and alignment block 102 may be re-tightened, and the connector 188 may be removed so that the stylus 160 may be attached. In other embodiments, such as shown in FIG. 74, many of these steps are unnecessary, due to the planar joint connection between the secondary alignment block 128 and the alignment block 102.

2. Tibial Resections

As mentioned above, tibial resections can generally include one or more of the steps of: making a medial tibial plateau resection, making vertical medial and lateral tibial eminence resections, performing a medial plateau balance check, performing a lateral tibial plateau resection, and performing a trial reduction to assess range of motion. These steps, in some embodiments, do not necessarily have to be performed in this order.

a. Medial Tibial Plateau Resection

Once the medial tibial resection guide 148, stylus 160, and/or secondary alignment block 128 assembly is placed in a desired position and orientation, one or more of these components can be secured to the proximal tibia 12 using bone pins or other fastening mechanisms. For instance, the medial tibial resection guide 148 shown in FIGS. 45a through 45c includes a medial resection opening 156 and a lateral resection opening 158 that guide the placement of bone pins or other fasteners into the proximal tibia which, in some embodiments, may perform one or both of the dual functions of (1) securing the medial tibial resection guide 148 to the proximal tibia 12 for stability during resection, and (2) acting as stops to limit the movement of a reciprocating saw or other cutting device. In some embodiments, the bone pins may act as stops to prevent accidental notching of the tibial eminence during medial and/or lateral tibial plateau resections as well as to prevent making the vertical medial and lateral eminence bone cuts too deep into the proximal tibia 12, reducing potential stress concentrations and providing other benefits. These pins, in some embodiments, may be located at intersection points at the base of the vertical eminence resections and the mesial extents of the plateau resections. In some embodiments, such as embodiments that use the dual-bladed reciprocating bone cutting saw described below, a single bone pin (in either the medial or lateral resection opening 156, 158) can function to limit the depth of both vertical eminence bone cuts.

Figure 75:
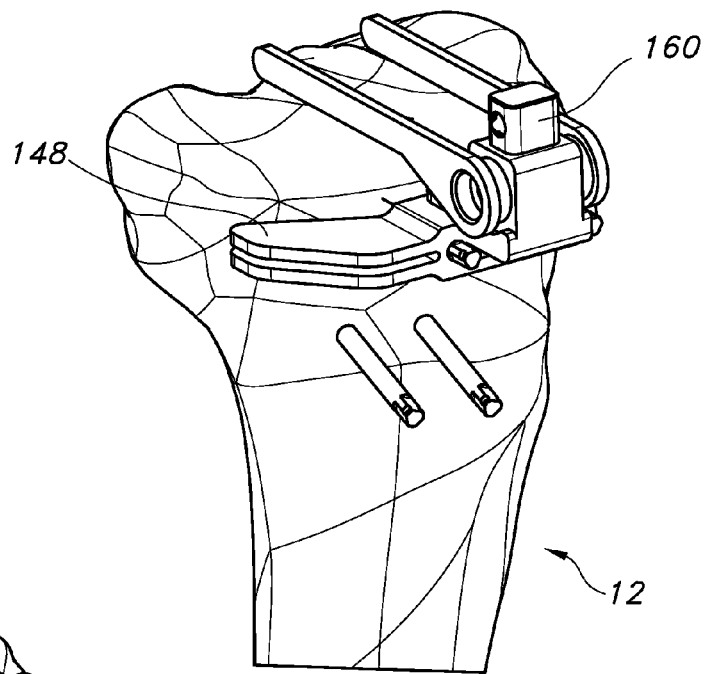
FIGS. 75 through 87 illustrate various methodologies and apparatus for making plateau and/or eminence resections on the proximal tibia.
Figure 76A:
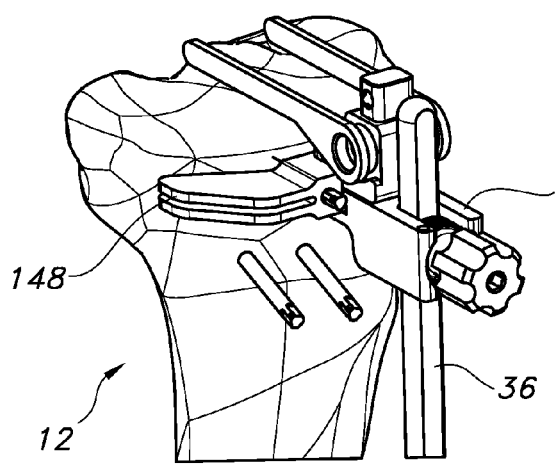
Figure 76B:
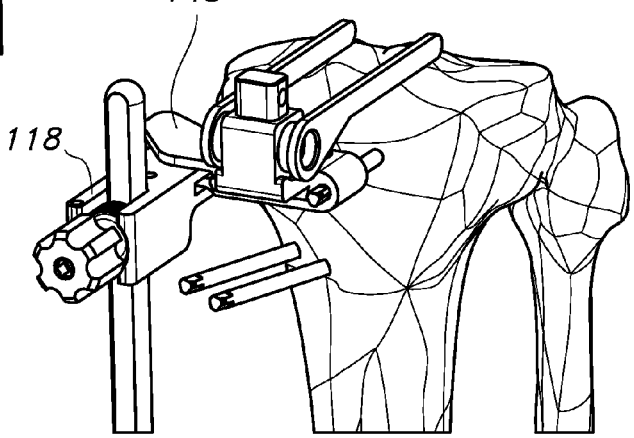

As shown in FIGS. 75 and 76, once the medial tibial resection guide 148 has been pinned to the proximal tibia 12, in some embodiments, other components such as the alignment block 102 and secondary alignment block 128 can be removed. As shown in these Figures, if desired, the pins securing the alignment block 102 (or other components) to the proximal tibia 12 can be left in place to preserve information about the neutral varus/valgus, neutral posterior slope, or other information in the event it is desirable to reattach such components or other components later in the procedure. As shown in FIG. 76a, extramedullary rod connector 118 and extramedullary alignment rod 36 may, in some embodiments, be directly attached to the medial tibial resection guide 148 as an additional alignment check. In the embodiment shown in FIG. 76b, the extramedullary rod connector 118 references the medial cutting guide surface 154 (see FIG. 45a) to indicate the varus/valgus and posterior slope angles of the medial tibial plateau resection. In some embodiments, the medial cutting guide could be positioned using an extramedullary rod connector and extra medullary alignment rod alone.

Once the medial tibial resection guide 148 is secured to the proximal tibia 12, a saw or other cutter can be used to perform the medial tibial plateau resection. If a medial tibial resection guide 148 such as the one shown in FIG. 46 is used, a lateral tibial plateau resection may optionally also be made at this time.

b. Vertical Eminence Resections

Figure 77:
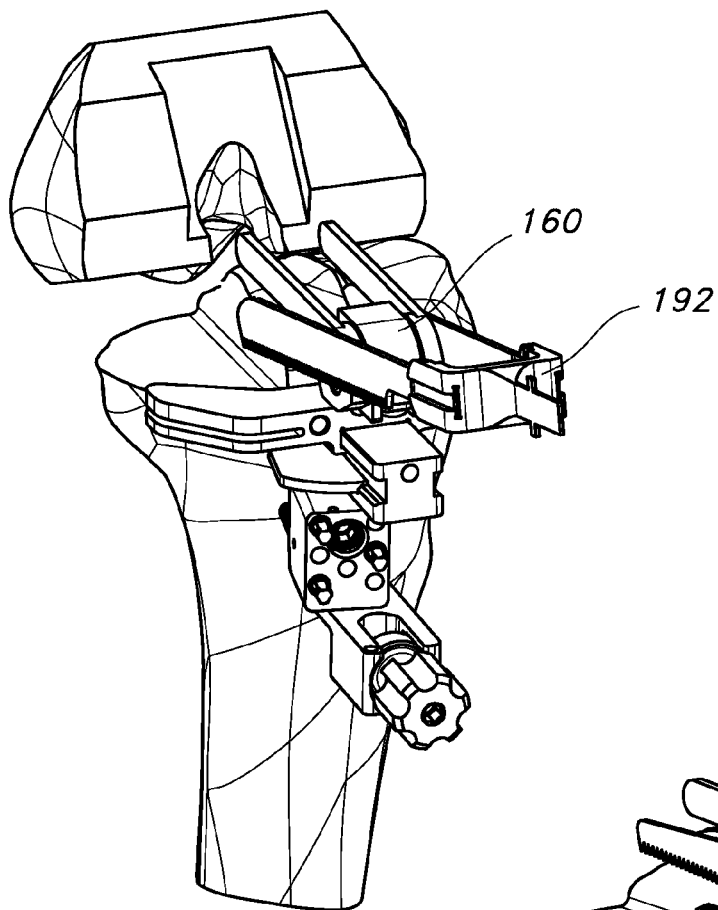
Figure 78:
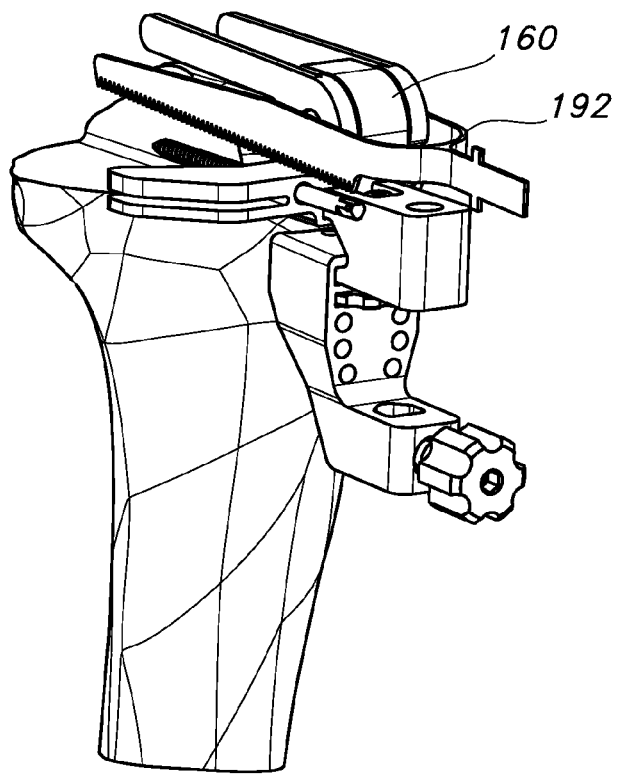

In order to fully remove the medial plateau portion of the proximal tibia 12, at least one generally vertical medial eminence resection must be made in addition to a medial plateau resection. As shown in FIGS. 77 and 78, the stylus 160 can function as a cutting guide for these vertical resections, which delineate the medial and lateral boundaries of the preserved tibial eminence. Traditional single bladed reciprocating saws can be used for the vertical resections, although, as shown in FIGS. 77 and 78, dual-bladed reciprocating saw blades 192 can also be employed to cut both medial and lateral eminence bone cuts simultaneously.

Figure 82:
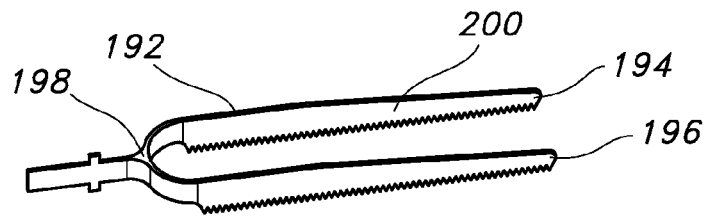

FIG. 82 illustrates an embodiment of a monolithic dual-bladed saw 192, which includes a first elongated reciprocating bone cutting blade 194, a second elongated reciprocating bone cutting blade 196, and a connector 198 connecting the two blades together. The connector 198, which in FIG. 82 is "Y" shaped although other shapes are also envisioned, connects the two blades 194, 196 together at proximal ends of the blades 194, 196, which extend generally parallel to one another to define cutting planes that are substantially parallel to one another. In some embodiments, blades 194, 196 are positioned approximately 10 to 30 mm apart from one another. In some embodiments, blades 194, 196 are positioned approximately 19-22 mm apart from one another. Each blade 194, 196 includes an inner, planar surface 200 for contact with the planar outer surfaces of indicator members 172, 174 of stylus 160. The inner, planar surfaces 200 of the blades 194, 196 and the outer, planar surfaces of indicator members 172, 174 may be substantially smooth, to facilitate even sliding of the blades 194, 196 on the indicator members 172, 174 during use.

In some embodiments, because blades 194, 196 are only connected together at their proximal ends, it may be desirable to manufacture the blades 194, 196 (or adjust the blades after manufacture) such that they are slightly biased towards one another, such that they are biased in contact with stylus 160 during use, which may provide some stability to the dual bladed saw 192 during use.

Figure 80:
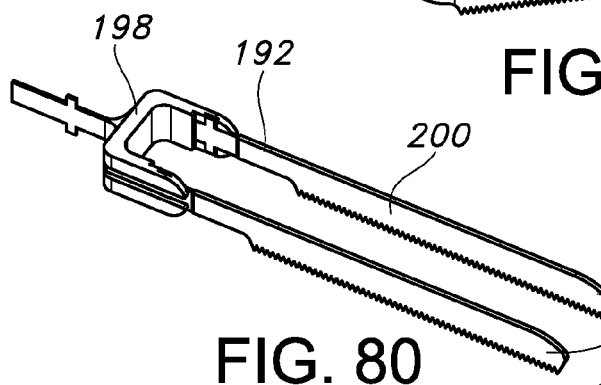
Figure 81:
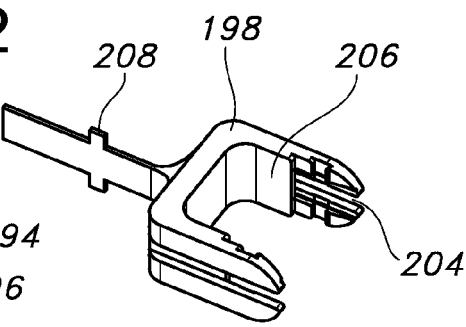
Figure 79:
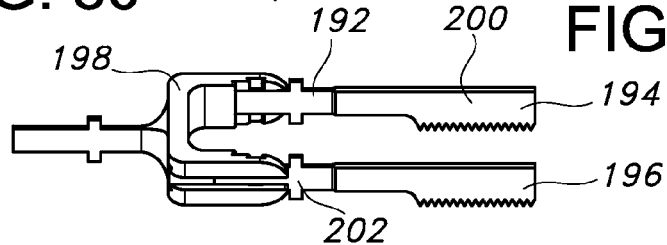

FIGS. 79 through 81 illustrate a modular dual-bladed saw 192 where the first and second blades 194, 196 are removably connected to connector 198. As shown in these Figures, each blade 194, 196 includes an attachment feature 202, such as but not limited to a "T" shaped shank, that interacts with corresponding structure on the connector 198 to secured blades 194, 196 in connector 198. FIG. 81 shows that connector 198 includes slots 204 sized to receive the "T" shaped shank and also capture it at one end (see ref. 206) to secure blades 194, 196 in connector 198. In the particular embodiment shown, flexing distal ends of the blades inwardly towards one another with respect to their shanks will permit insertion and removal of the shanks into the grooves. Other mechanisms such as, without limitation, one or more set screws, spring fingers, ball detents, collets, wedges, clamps, jaws, or any other friction increasing or other devices known in the art could be used to secure blades 194, 196 in connector 198.

In the embodiment shown in FIGS. 79 through 81, first and second blades 194, 196 are standard reciprocating surgical bone cutting saw blades, and the attachment features 202 of those blades 194, 196 are designed for connecting them, albeit one at a time, directly to a reciprocating saw (not shown). Accordingly, in at least some embodiments, it will be desirable for the attachment features 202 of the blades 194, 196 to be substantially the same size and shape of the attachment feature 208 of the connector 198, so that the connector 198 can be used with the same types of reciprocating saws.

Figure 83:
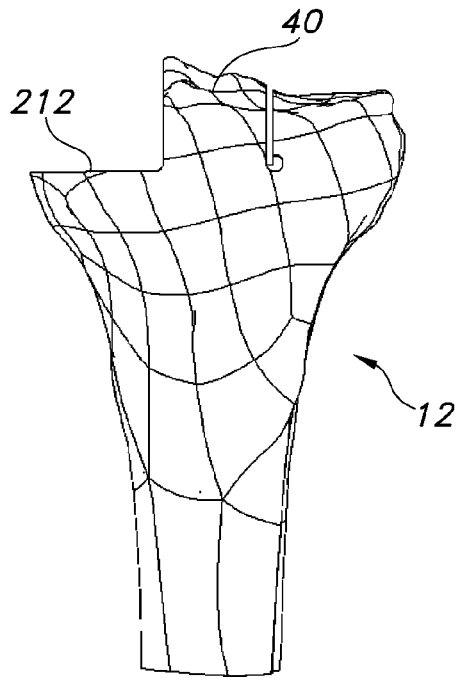

The dual-bladed saws 192 shown in FIGS. 79 through 82 are configured to make generally parallel (in both superior/inferior and anterior/posterior directions) resections around the tibial eminence 40, such as illustrated in FIG. 83. This embodiment may be advantageous for cruciate retaining procedures since it allows to resections to be made simultaneously, thereby saving time and also increasing the likelihood that the two resections will be parallel with respect to one another. In other embodiments, however, it may be desirable to vertically resect the tibial eminence in non-parallel manners, such as to create generally trapezoidal prism shaped tibial eminences.

Figure 84:
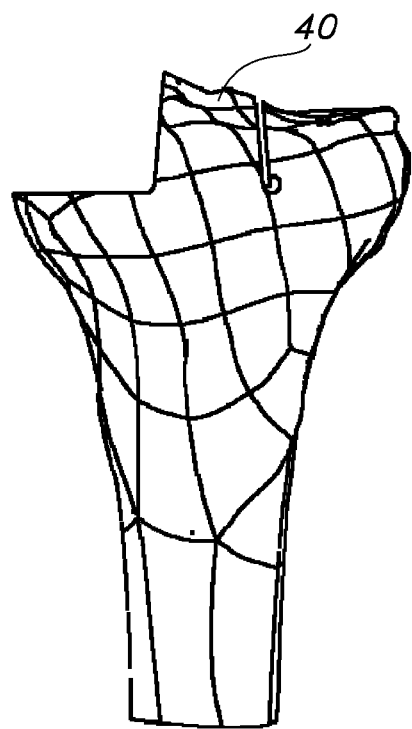
Figure 85:
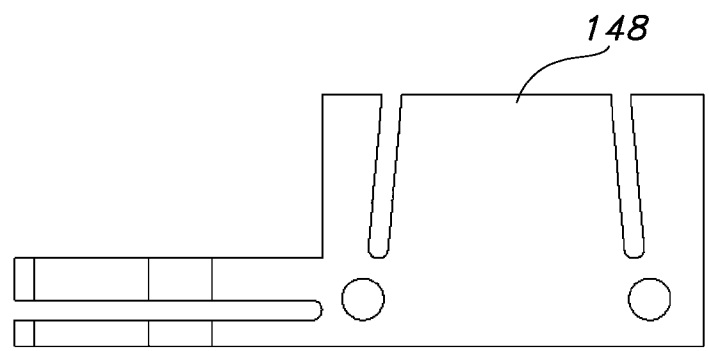

For instance, FIG. 84 shows one set of non-parallel vertical tibial eminence resections where the vertical resections extend at an obtuse angle relative to their corresponding horizontal plateau resections. In some embodiments, a trapezoidal prism shaped resected tibial eminence 40 may reduce stress concentration at the eminence base and facilitate introducing compression and shear forces between the tibial baseplate and the eminence walls to prevent the eminence from breaking off under high ligament tensions. These compression and shear forces between the tapered eminence bone cuts and the tibial baseplate may be present even when the two are separated by a cement mantle. It should be understood by those of ordinary skill that a single reciprocating saw would likely be used to create the angled medial and lateral eminence bone cuts shown in FIG. 84, and could be formed using medial tibial resection guides 148 such as shown in FIG. 85.

Figure 86:
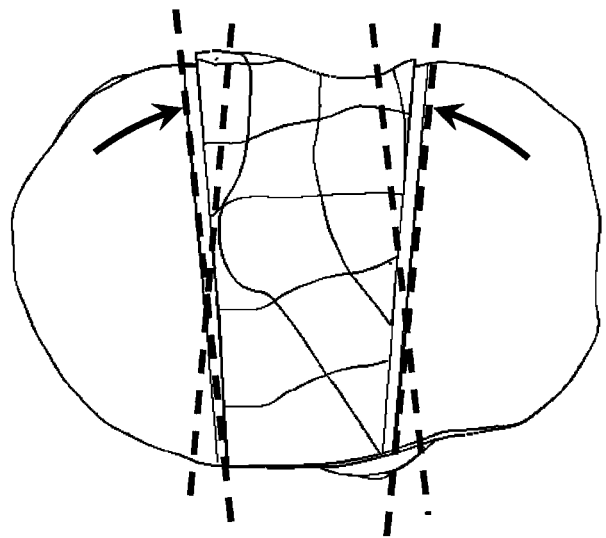
Figure 87:
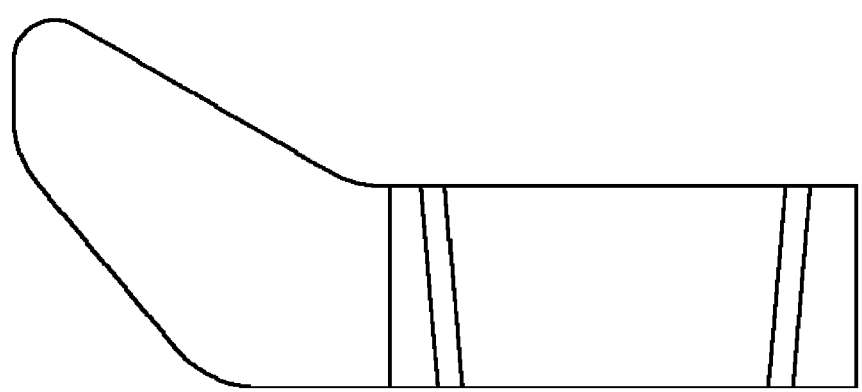

Eminence bone cuts may also be oriented to form of a wedge in a transverse plane along a superior-inferior axis of the tibia as illustrated in FIG. 86, which may be created with the assistance of a cutting block such as shown in FIG. 87. These and other foreseeable combinations of eminence bone cut orientations are envisaged as possible embodiments.

In some embodiments, it may be desirable before making final vertical tibial eminence bone cuts to make provisional vertical tibial eminence bone cuts in order to asses the planned position of the tibial baseplate with respect to the tibial eminence and other tibial anatomy. There are generally three criteria for setting tibial degrees of freedom. A first consideration is the orientation of the femur in full extension. A second consideration is the location of attachment points of the cruciates (i.e., the ACL and PCL) on the tibial eminence. A third consideration is the final positioning of the outer periphery of the tibial baseplate relative to the cortical rim of the resected tibial plateau (i.e., making sure the baseplate does not overhang, and that bone "fit" and "coverage" is optimized). The second and third considerations become increasingly more important as the clearance between the eminence gap of the tibial baseplate and the actual tibial eminence width becomes smaller.

Figure 160:
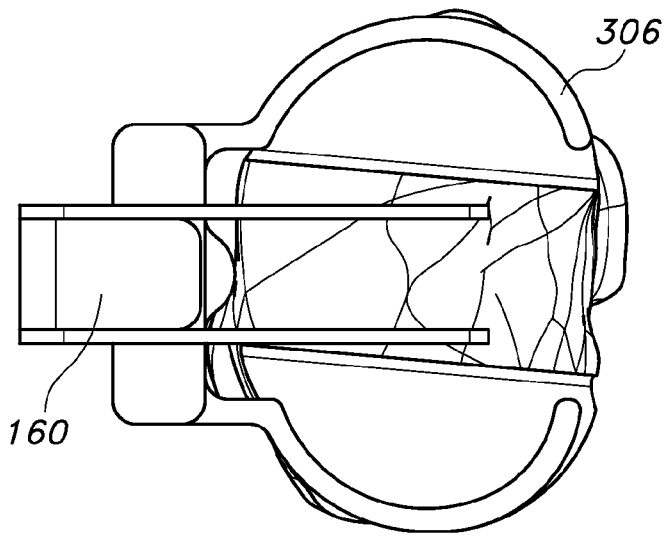
FIGS. 160 through 162 illustrate an alternative embodiment for making vertical eminence resections on the proximal tibia.
Figure 161:
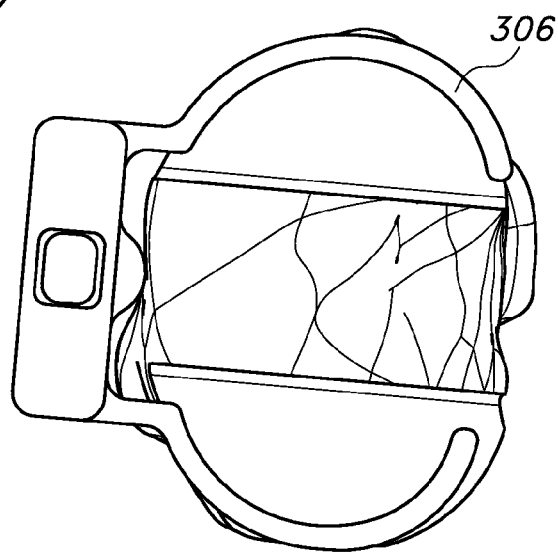

According to some methods such as shown in FIGS. 160 through 162, provisional eminence bone cuts may be made. For instance, medial and lateral generally vertical eminence bone cuts may be made at slightly wider locations than the width than is required for the final tibial implant. In other words, enough eminence bone is preserved during the provisional eminence bone cuts that secondary eminence bone cuts may be adjusted and re-cut in an orientation more conducive to optimal cortical coverage (e.g., optimizing the third consideration described above). Once the provisional medial and lateral eminence bone cuts have been made (and prior to trial reduction steps), a trial tibial baseplate 306 having an eminence gap wider than the provisional eminence cuts may be placed on the resected tibial plateaus and shifted to a position where cortical bone coverage is optimal. In the particular embodiment shown in FIGS. 160 through 162, baseplate 306 references (using a "bump" as shown or other suitable structures or mechanisms) an anterior aspect of the proximal tibia. The eminence may then be re-cut as necessary to provide better cortical coverage of the trial tibial baseplate. The aforementioned cutting steps may be facilitated by a special "large width" provisional stylus 160, or by a stylus provided with extra thick arms to increase the eminence width between the medial and lateral eminence bone cuts. Thus, with these methods, information about the cortical coverage is available prior to finalizing the permanent shape and position of the tibial eminence.

In some embodiments, a dual bladed reciprocating saw blade 192 can be used instead of a stylus 160, to function as an indicator or alignment guide for positioning and orienting a medial tibial resection guide 148. In such embodiments, since a stylus 160 is not used, it may be desirable to use a medial tibial resection guide 148 that has vertical eminence bone cut guides incorporated into it (such as the guide shown in FIG. 85).

c. Medial Plateau Balance Check

In some embodiments, although not necessarily all, it may be desirable to evaluate the medial plateau resection before making the lateral plateau resection. As described below, evaluation of the medial plateau resection prior to making the lateral plateau resection (or in other embodiments, evaluation of a lateral plateau resection prior to making a medial plateau resection) can help reduce the risk that the other plateau resection will have to be cut twice by ensuring that before the second plateau resection is made, its position has been optimized for the best kinematic, kinetic, and biomechanical outcomes. Additionally, or alternatively, evaluation of the medial or lateral plateau resection may, in some embodiments, be done in a manner to reduce the likelihood that the same side of the tibial plateau will have to be resected multiple times. In still other embodiments, the evaluations described below (and the apparatus for performing such evaluations) can be modified for use after both the medial and lateral resections, which may reduce the likelihood that the plateau resections will have to be resected multiple times.

There are at least two situations where re-cutting a medial plateau resection (or other plateau resection(s)) may be necessary. In some instances, re-cutting may be necessary when a tibial trial implant (e.g., a medial tibial trial insert) sits too proud on the proximal tibia. If reducing the thickness of the tibial insert cannot resolve the problem, the medial plateau resection needs to be relocated slightly deeper to make more room for the thickness of the tibial implant. A second instance where re-cutting is typically necessary is when the posterior slope angle of the medial plateau resection needs adjustment. For example, if there is too much laxity or tightness in extension or flexion, then the posterior slope angle may be too shallow or too steep.

As used herein, "evaluation" of the medial plateau or other resection(s) can take the form of a variety of different checks on the suitability of its positioning and/or orientation, or the potential need to re-cut or redo the resection at a different depth or orientation (e.g. at a different posterior slope angle).

In some embodiments, evaluation can take the form of articulating a femoral trial on a medial tibial trial, which may, in some embodiments, allow the surgeon to check the balance, tightness, and/or laxity of the knee joint in flexion and extension. In some embodiments, such evaluations can involve using these or additional tibial trials from a kit of tibial trials to simulate the effect of a re-cut of the resection or the use of a different tibial implant on the balance of the knee joint, which may, in some embodiments, reduce the risk associated with having to re-cut the resection. FIGS. 88 through 98 illustrate non-limiting embodiments of methods and apparatus useful in such evaluations.

Figure 88:
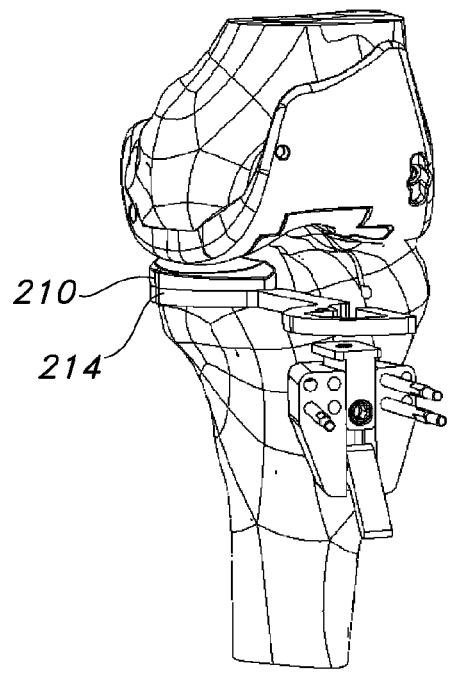
FIGS. 88 through 98 illustrate various methodologies and apparatus for evaluating a medial plateau resection on the proximal tibia.
Figures 89, 90, 91:
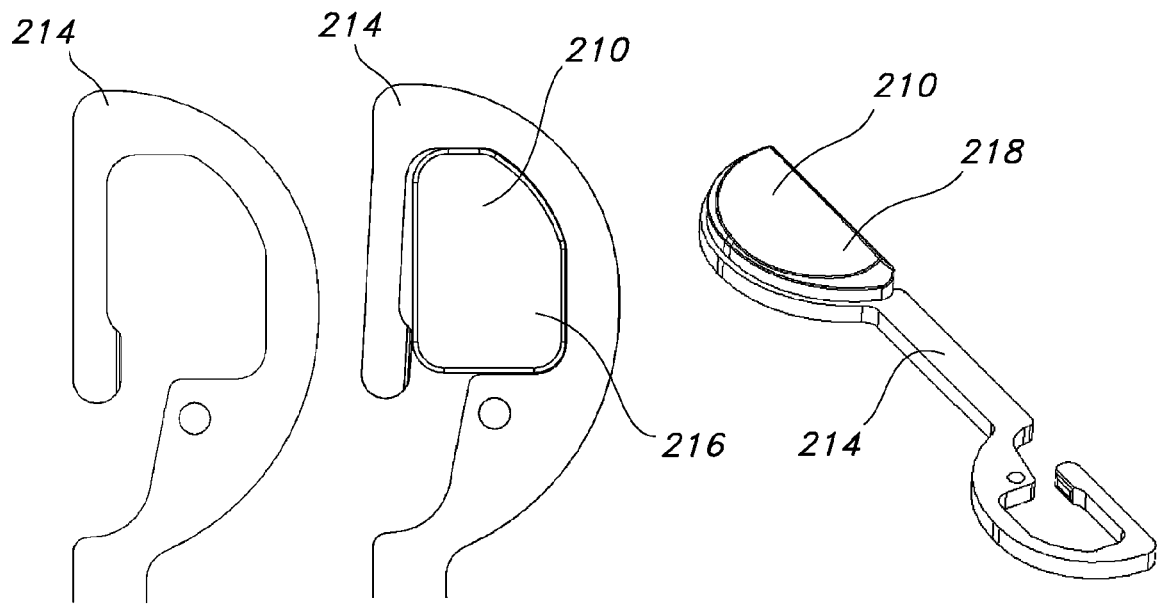

FIG. 88 illustrates one embodiment of the use of a tibial trial insert 210 for the evaluation of a medial plateau resection 212, an example of which is shown in FIG. 83. As shown in FIG. 88, the tibial trial insert 210 is associated with a handle 214, which includes a planar inferior surface (see, e.g. FIGS. 90-91) for referencing the medial plateau resection 212. As shown in FIGS. 90-91, the inferior surface 216 of the tibial trial insert 210 is designed to connect to or rest in the handle 214. When the tibial trial insert 210 is connected to the handle 214, and the handle positioned on the medial plateau resection 212, the superior surface 218 of the tibial trial insert 210 replicates (at least in some aspects) the expected final positioning and orientation of a corresponding articulation surface of a tibial implant (baseplate+insert) implanted on the medial plateau resection 212. In some embodiments, the tibial trial insert 210 is part of a kit of inserts which can simulate: 1) the final position and orientation of an articular surface of a tibial implant without re-cutting bone, and 2) the final position and orientation of an articular surface of a tibial implant after a predetermined type of re-cut (e.g., changes to depth only, posterior slope angle only, or combinations thereof), without actually re-cutting bone.

Figure 92:
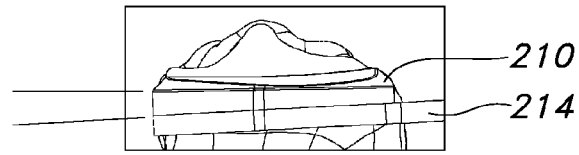

FIGS. 92 through 95 illustrate tibial trial insert options according to some embodiments of the invention for simulating different implant options or surgical decisions (e.g. re-cutting). FIG. 92 shows a medial tibial trial insert 210 that simulates the use of a different tibial insert that has a bevel to compensate for a medial plateau resection that has too much or not enough posterior slope. The medial tibial trial insert 210 of FIG. 92 may be part of a kit of several trial inserts in which the angles and orientations of the bevels on those inserts vary in order to mute the adverse effects of a primary medial plateau resection having an inadequate posterior slope angle and avoid re-cutting the tibia. In other words, each medial tibial trial insert 210 within the set shares the same or a similar implant thickness, (e.g., the approximate thickness measured at the thinnest portion of the insert) but each insert within the set incorporates a different bevel angle to compensate for primary resections having a poor posterior slope angle.

Figure 93:
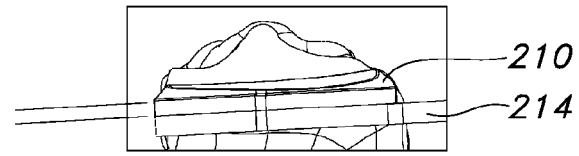

FIG. 93 shows a medial tibial trial insert 210 that simulates the use of a different tibial insert that has a different thickness to compensate for a medial plateau resection that is either too superior or inferior (e.g. if the knee joint is too tight or too loose in both flexion and extension). The tibial trial insert 210 of FIG. 93 may be one of a set of inserts 210 that share the same or similar posterior slope angles, but have different overall thicknesses.

Figure 94:
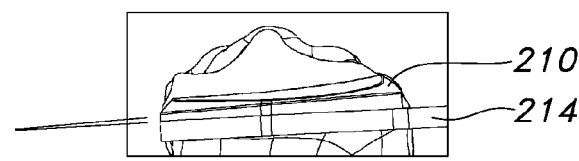

FIG. 94 shows a medial tibial insert 210 that simulates re-cutting the medial plateau resection at a different posterior slope angle (e.g. if the knee joint is too tight or too loose in one of flexion or extension). These inserts 210 are termed "re-cut simulation" trial inserts, and they generally provide the surgeon with a way to trial as if he or she has made a re-cut before any re-cuts are made. In this way, the surgeon may investigate his or her options for compensating for laxity or tightness in flexion or extension without needing to actually cut bone to do so. This may lower the chances that no more than two resections to the medial plateau and one resection to the lateral plateau will be needed during the procedure. In some embodiments, the medial tibial insert 210 shown in FIG. 94 may correspond to the secondary alignment block 128 shown in FIG. 97 that will facilitate resecting the medial tibial plateau resection at a different posterior slope angle from the secondary alignment block 128 shown in FIG. 96 that was originally used in the first resection of the medial tibial plateau. The tibial trial insert 210 of FIG. 94 may be one of a set of inserts 210 that have different posterior slope angles to simulate re-cutting the medial plateau resection at a different posterior slope angle.

Figure 95:
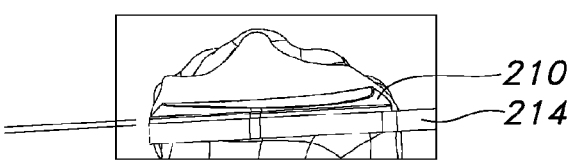
Figure 96:
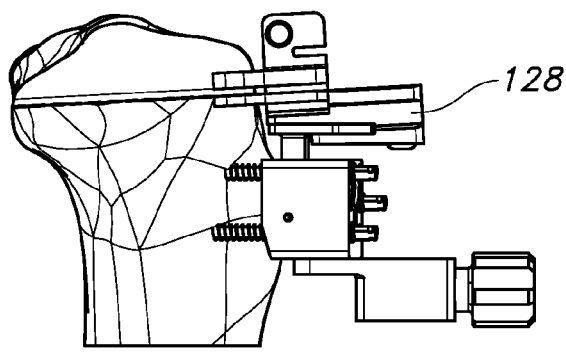
Figure 97:
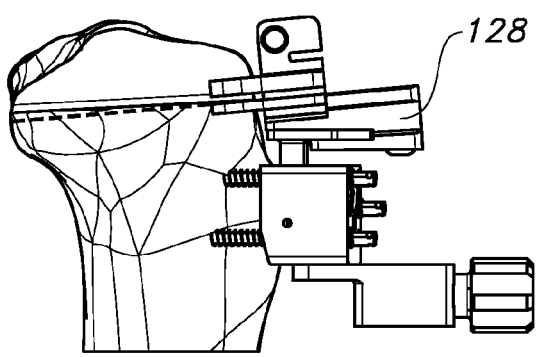
Figure 98:
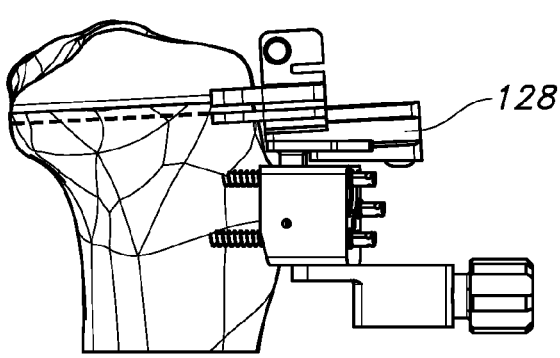

FIG. 95 shows a medial tibial insert 210 that simulates re-cutting the medial plateau resection at a different resection depth (e.g. if the knee joint is too tight or too loose in both flexion or extension, and implant thickness cannot be adjusted to adequately compensate). For instance, a surgeon may choose to perform range of motion and laxity tests before re-cutting a second plateau resection slightly deeper and generally parallel to the first resection. In some embodiments, the medial tibial insert 210 shown in FIG. 95 may correspond to the secondary alignment block 128 shown in FIG. 98 that will facilitate resecting the medial tibial plateau resection at a different superior/inferior position from the secondary alignment block 128 shown in FIG. 96 that was used in the first resection of the medial tibial plateau. The tibial trial insert 210 of FIG. 95 may be one of a set of inserts 210 that have different thicknesses to simulate re-cutting the medial plateau resection at a different depths.

It should be noted that the tibial trial inserts discussed above may be used alone or in combination in order to trial virtually any surgical scenario prior to making a second medial plateau resection. Combinations of trial tibial insert simulations may include inserts that represent changing both implant thickness and posterior slope angle simultaneously or other combinations of implant attributes and resection levels and angulations. In other words, tibial trial inserts may be provided to simulate the steps of implanting a thicker or thinner tibial implant (e.g., tibial insert) after re-cutting the medial tibial plateau at a different posterior slope angle than the first resection.

d. Lateral Tibial Plateau Resection

FIGS. 99 through 107 illustrate embodiments of a lateral cutting guide 220 for guiding a cutting tool while making a lateral plateau resection on the proximal tibia 12. Other embodiments include a medial cutting guide having similar structures and functions to the lateral cutting guide 220 of FIGS. 99 through 107, but for use in cutting a medial plateau resection on the proximal tibia 12 (e.g. in a technique where the lateral plateau resection is made first and the medial plateau resection is second).

Figure 99:
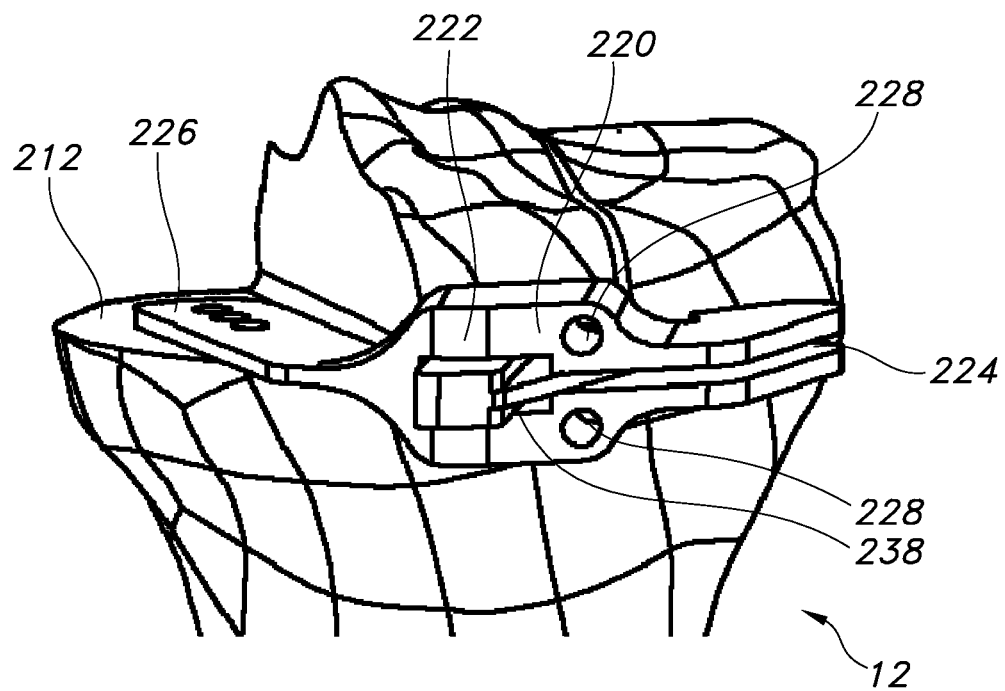

The lateral cutting guide 220 shown in FIG. 99 includes a block or body 222 defining a horizontal guide member 224 for guiding a cutting tool. In the embodiment shown in FIG. 99, horizontal guide member 224 is a slot with substantially planar superior and inferior surfaces for capturing and guiding the movement of a cutting tool in a horizontal plane, although, in other embodiments, horizontal guide member could be un-captured (e.g. a substantially planar inferior surface without a corresponding superior surface to capture the cutting tool). In the embodiment shown, the inferior planar surface of horizontal guide member 224 is positioned and oriented to be co-planar with the medial tibial plateau resection 212. A paddle 226 or other structure having a substantially planar reference surface (on an inferior surface not shown) may extend from the body 222 to reference the medial tibial plateau resection 212 and position and orient horizontal guide member 224 in substantially the same plane as the reference surface of the paddle 226 (although, in other embodiments, they can be offset from one another in one or both of rotational and translational aspects). Both the paddle 226 and other portions of the body 222 can include pin receiving openings 228 to facilitate securing the lateral cutting guide 220 to the proximal tibia 12, some of which may be oriented obliquely to further stabilize the lateral cutting guide 220 and also positioned into bone that will eventually be resected, minimizing the number of holes left in the proximal tibia 12 after the procedure.

Figure 100:
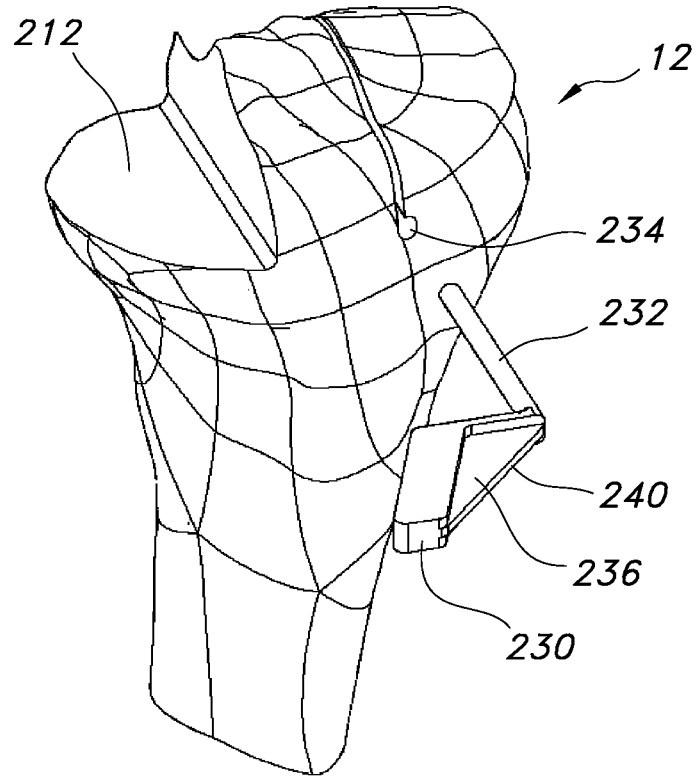
Figure 101:
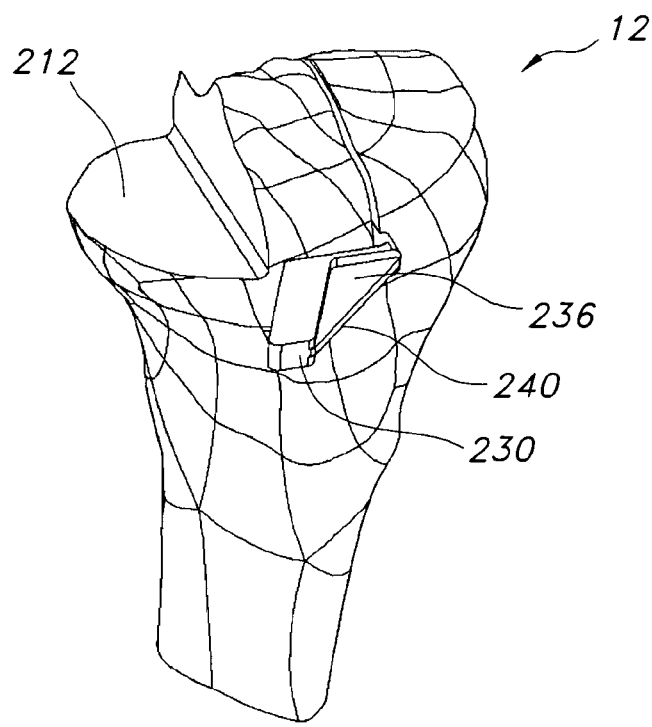
Figure 102:
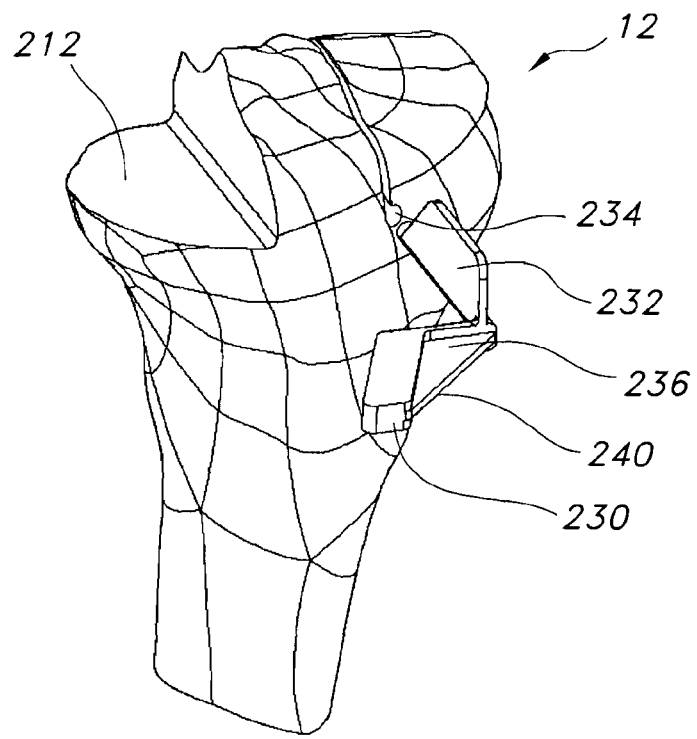
Figure 103:
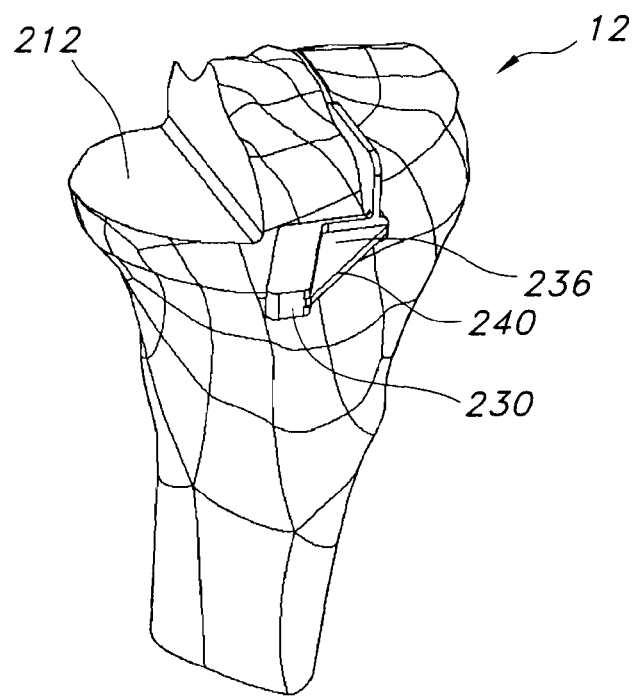

FIGS. 100 through 103 illustrate two embodiments of a flag pin 230 that can be used in connection with lateral cutting guide 220. The flag pins 230 shown in FIGS. 100 through 103 include elongated insertion portions 232 for insertion into a lateral navigation opening 234 formed in the proximal tibia 12, which can be formed, in some embodiments, by using the lateral resection opening 158 of the medial tibial resection guide 148 shown in FIG. 45a or in other manners. The elongated insertion portion 232 of the flag pin 230 shown in FIGS. 100 and 101 is substantially cylindrical. The elongated insertion portion 232 of the flag pin 230 shown in FIGS. 102 and 103 includes, in addition to a cylindrical portion, a planar section for insertion into the lateral, vertical eminence bone cut in the proximal tibia 12, which may further stabilize and align the flag pin 230 in the proximal tibia 12.

Depending on the particular procedure employed, due to the relatively small lateral operating exposure available with a medial incision approach, the presence of the laterally retracted extension mechanism and the unique shape of each tibia, it may be important to allow the surgeon to maneuver the lateral cutting guide 220 to a preferred position and to provide adequate space to maneuver a cutting tool such as a saw blade. However, in maneuvering a cutting tool, it may be desirable to protect the anterior and lateral sides of the eminence from inadvertent notching during the resection. Some embodiments of the lateral cutting guides 220 and flag pins 230 described herein may help to prevent or reduce the risk of inadvertent notching of anterior and lateral portions of the eminence and to otherwise protect the anatomy of the knee joint.

The flag pins 230 shown in FIGS. 100 through 103 may perform three functions of potential importance to the lateral tibial plateau resection. First, they may guard against lateral eminence notching. Second, they may provide a planar reference and at least one degree of freedom (e.g., medial-lateral translation, anterior-posterior translation, and internal-external rotation) while maintaining positioning and stability. Third, they create a relieved boundary to guard against anterior eminence notching while still allowing an anterior-medial approach of the saw blade.

Flag pin 230 may include an enlarged head potion 236 defining at least one substantially planar surface. This substantially planar surface (or surfaces) may provide a reference for facilitating the appropriate positioning of the lateral cutting guide 220 (in connection with paddle 226) such that the cutting guide 224 is substantially coplanar to the medial plateau resection 212 (such as by its interaction with a correspondingly shaped flag pin receiving opening 238 in the lateral cutting guide 220) while at the same time allowing some translational and/or rotational movement between the lateral cutting guide 220 and the proximal tibia 12. In other words, the interaction of the substantially planar enlarged head portion 236 of the flag pin 230 and the correspondingly shaped flag pin receiving opening 238 in the lateral cutting guide 220 may act as a planar joint that provides stability and maintains the lateral cutting guide member 224 in a coplanar relationship with the medial plateau resection 212 while allowing for other translations and rotations of the lateral cutting guide 220 for optimum positioning against the proximal tibia 12. FIGS. 105 and 106 illustrate how such a planar joint could allow the lateral cutting guide 220 to be rotated at an angle ø, which may position the guide 220 closer to the lateral side of the tibia 12 in a more desirable orientation for the surgeon.

As mentioned above, flag pin 230 may also provide a relieved boundary which guards against anterior and other eminence notching while still allowing an anterior-medial approach of the saw blade. In this respect, an angled leading edge 240 of the enlarged head portion 236 in addition to the elongated insertion portion 232 may act as an additional guide to limit the movement of a cutter in a mesial direction towards anterior and lateral aspects of the tibial eminence 40, while not overly interfering with the cutting tool's access for the lateral plateau resection. This guiding function of the flag pin 230 is schematically illustrated in FIG. 107.

In some embodiments, while referencing the medial plateau resection, the lateral cutting guide 220 may be stabilized using additional or alternative means. For example, in some embodiments, paddle 226 may be thickened or augmented with a spacer block that mates with or rests against the femoral trial 80. In other examples, paddle 226 may be inserted into a resection kerf or slot created by the horizontal medial plateau resection bone cut prior to making the generally vertical medial eminence bone cut. In doing so, paddle 226 is captured from above and below by native tibial bone.

e. Trial Reduction

Figure 104:
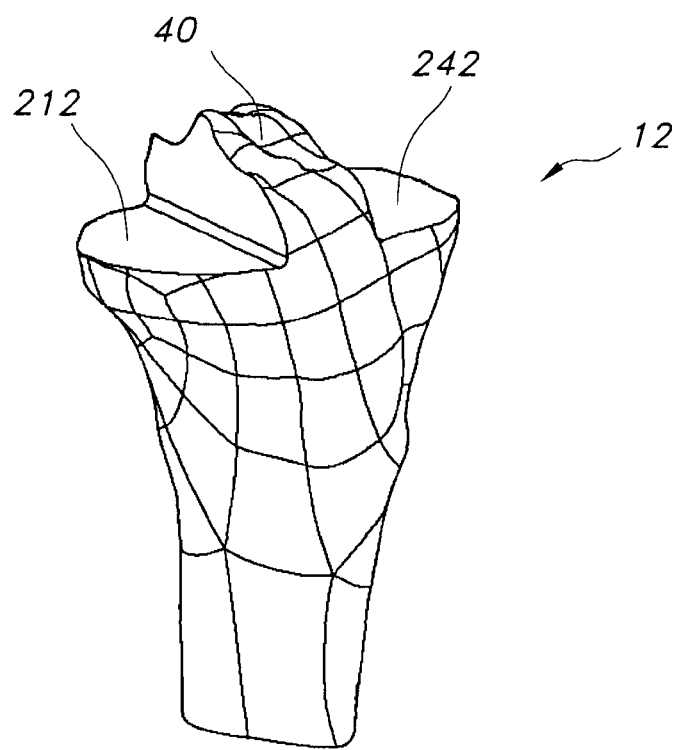

FIG. 104 illustrates the proximal tibia 12 after the medial plateau resection 212 and lateral plateau resection 242 have been completed, but before removal of an anterior portion of the tibial eminence 40 and before punching for the keel of the tibial implant.

Fracture of the tibial eminence can be a possible intra-operative and a post-operative threat to successful bicruciate-retaining arthroplasty. Intra-operatively, trial reduction steps such as evaluating range of motion may present a high risk of eminence fracture due the intensity of varus/valgus stress tests. Post-operatively, large loads passing through the ACL and to the anterior attachment point of the ACL on the tibial eminence may also increase the risk of eminence fracture. In order to reduce these risks, some embodiments described herein provide methods for trialing prior to removing anterior portions of the anterior eminence. Means for facilitating trialing prior to removing the anterior eminence may comprise a tibial baseplate 244 that bypasses the anterior aspect of the eminence as shown in FIGS. 108 through 112.

Figure 112:
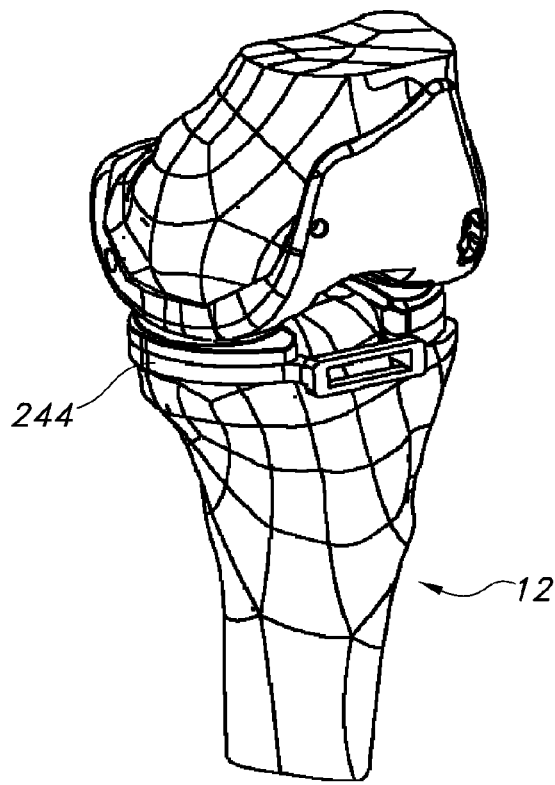
Figures 113, 114:
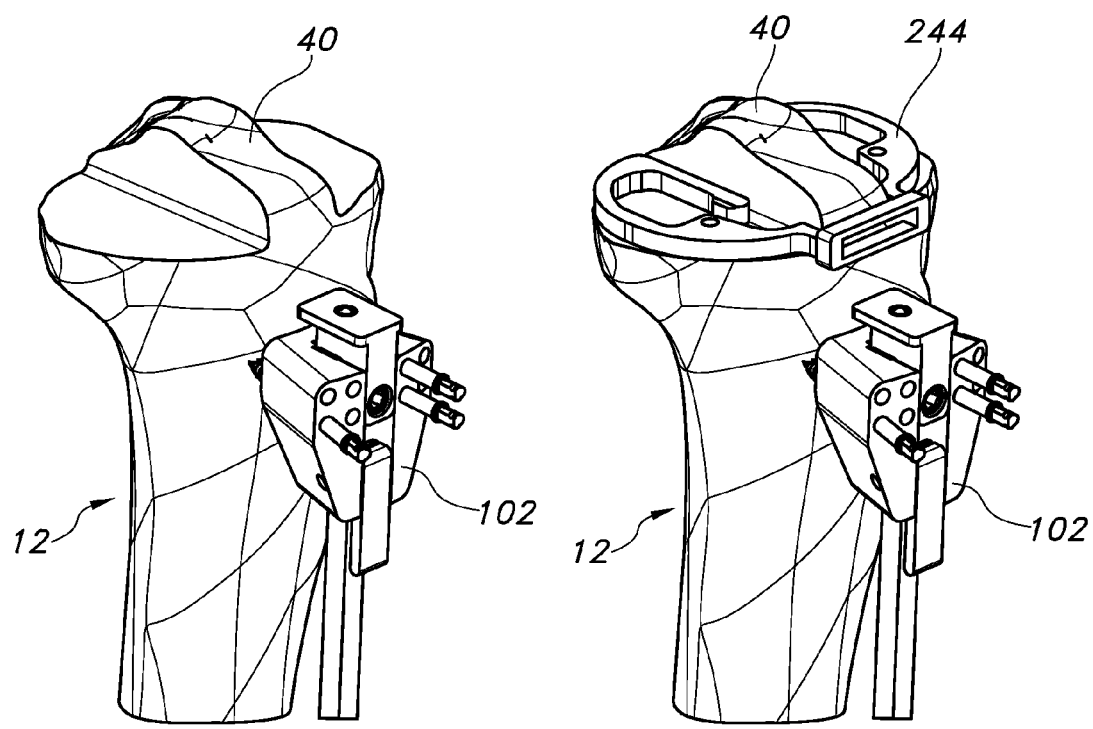

Methods according to some embodiments utilize an "anterior cut last" method for reducing the likelihood of anterior eminence fracture. A tibial baseplate 244 (one embodiment of which is shown in FIG. 108) may be structured to be positioned on the proximal tibia 12 while providing space for an intact anterior portion of the tibial eminence 40 (FIGS. 108 through 110). A pair of trial inserts 246 can be secured to the tibial baseplate 104 (FIG. 111) to facilitate a trial reduction, balance check and range of motion check in connection with a femoral trial (FIG. 112). If range of motion and laxity are satisfactory, the final finishing steps of punching a keel cavity and removing the anterior portion of the tibial eminence may, in some embodiments, be performed (discussed in a section further below).

The tibial baseplate 244 shown in FIG. 108 includes a medial baseplate web 248, a lateral baseplate web 250 (inferior portions of which, not shown, include substantially planar surfaces (co-planar to one another) for referencing the medial and lateral plateau resections), and a bridge 252 connecting the two webs 248, 250 together. The tibial baseplate 244 defines a gap 254 between the two webs 248, 250 that is sized and positioned to receive a tibial eminence 40 including anterior and posterior cruciate ligament attachments sites. In some embodiments, this gap measures approximately 14 to 40 mm in a medial/lateral direction and 35 mm to 70 mm in an anterior/posterior direction. The baseplate webs 248, 250 can define attachment features to facilitate the connection of medial and lateral tibial trial inserts 246 to the baseplate 244 (see FIG. 111). In some embodiments, for instance, the webs 248 and 250 may be somewhat resilient and have structure for snapping into corresponding grooves or other receiving structures in the inserts 246. Any other desired mechanisms or structures could be used to secure the inserts 246 to the baseplate 244. In still other embodiments, the trial inserts can be an integral part of the trial baseplate. In still other embodiments, the inserts can just rest in the trial baseplate, and are not attached to the baseplate.

In some embodiments, the tibial baseplate 244 can be used to gauge and visualize what the final position of a bicruciate retaining tibial implant will be on the proximal tibia 12, in order to ensure appropriate coverage, that the implant will not hang over the cortical rim of the proximal tibia 12, that the clearance between the implant and eminence will be appropriate, and to check other alignments, clearances and spacings. The medial baseplate web 248 may include a mesial reference surface 260 for illustrating an extent of a medial, mesial surface of the tibial implant, and an outer reference surface 262 for illustrating an extent of a medial, outer surface of the tibial implant. The lateral baseplate web 250 may include a mesial reference surface 264 for illustrating an extent of a lateral, mesial surface of the tibial implant, and an outer reference surface 266 for illustrating an extent of a lateral, outer surface of the tibial implant. The tibial baseplate 244 may also include one or more datum sites, such as apertures 268 or attachments for other instrumentation discussed below, for marking on the tibia or otherwise indicating or defining positioning of the trial baseplate 244 with respect to the proximal tibia 12 once a desire positioning is obtained.

In some embodiments, such as illustrated in FIGS. 160 through 162, a trial baseplate 306 can be sized and otherwise configured for provisional eminence cuts that are wider than the final eminence cuts, in order to allow for earlier assessment of cortical rim coverage and eminence clearance.

3. Finishing

As mentioned earlier, finishing steps may generally include one or both of the steps of: (1) punching a keel cavity into the cancellous bone of the proximal tibia 12, and (2) making an anterior eminence bone cut and an anterior tibial plateau resection to remove an anterior block portion of the tibial eminence 40.

In some embodiments, the tibial baseplate 244 used during trialing and assessing range of motion may remain in place for the punching and anterior eminence bone cut steps and can essentially act as the datum reference for the punching and cutting instruments. Depending on the specific structure, positioning and orientation of the punching and cutting instruments used with the tibial baseplate 244, the tibial baseplate 244 may be formed with appropriately shaped, positioned and oriented gaps, slots or other openings to permit the punching and cutting instruments to pass through the tibial baseplate 244 and into the bone of the proximal tibia 12. For instance, the embodiment of a tibial baseplate 244 shown in FIG. 110 includes gaps 278 for receiving medial and lateral portions of a U-shaped punch described below, and includes a slot 280 (see FIG. 111) that allows a chisel or other cutter to pass for making a horizontal bone cut to the anterior portion of the tibial eminence 40, as also described below.

Figures 115, 116:
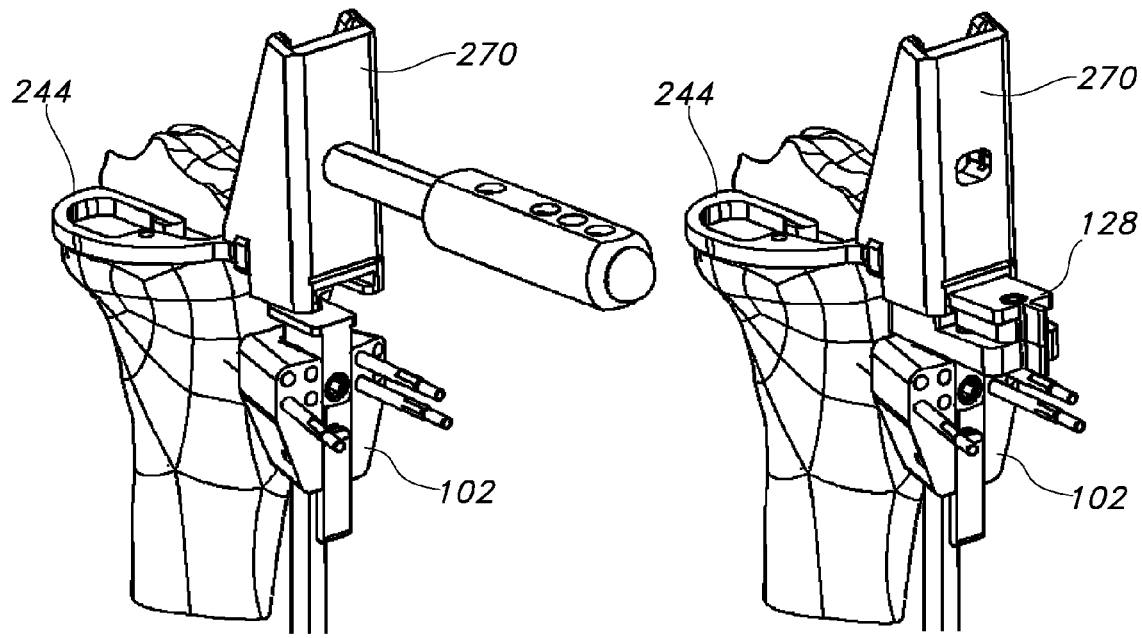
Figures 117, 118:
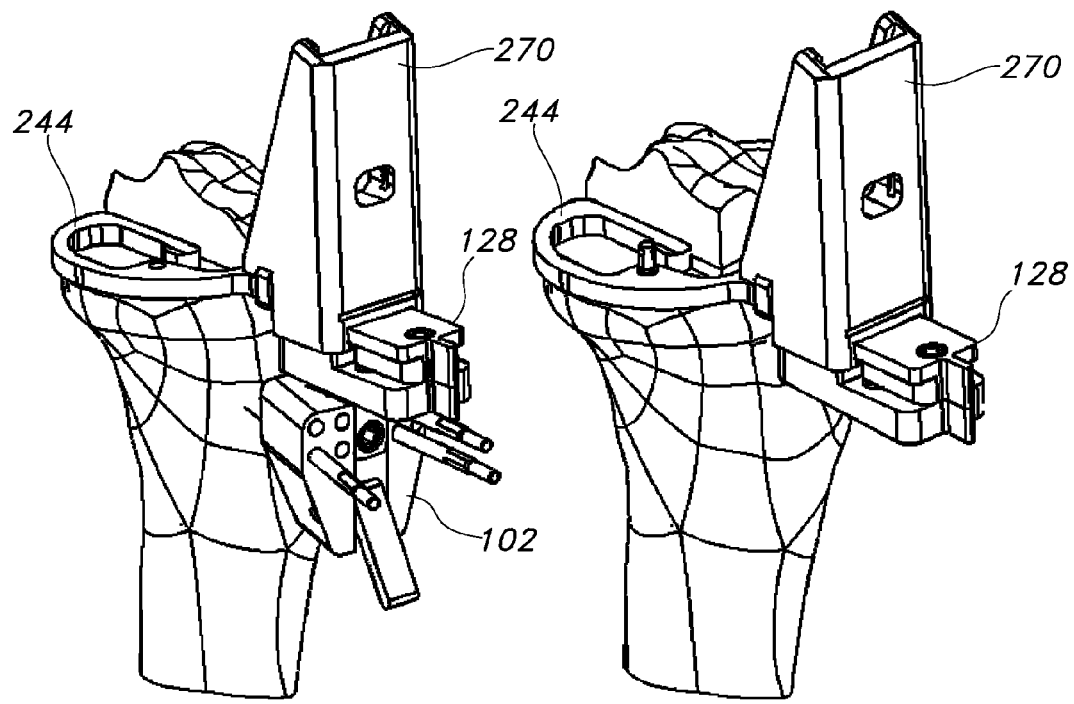
Figures 119, 120:
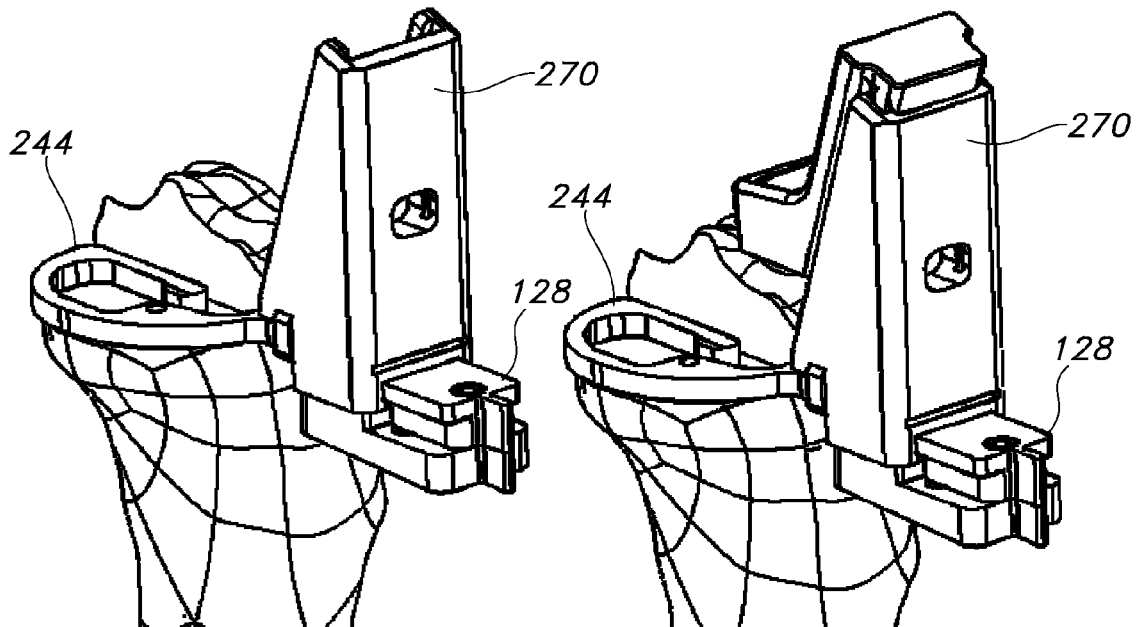
Figure 121:
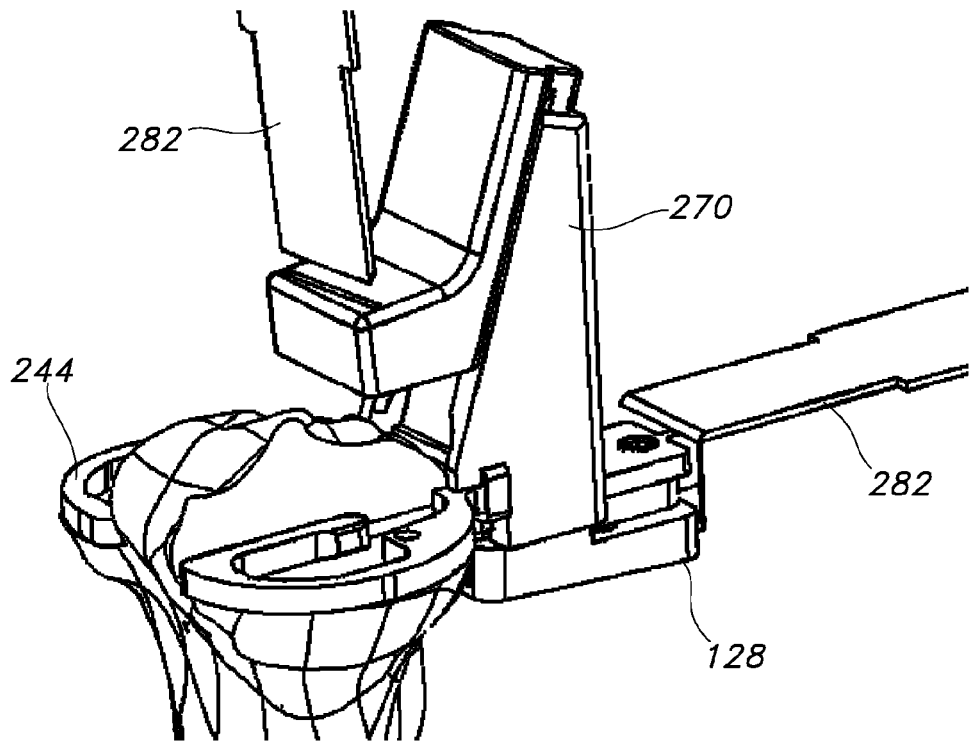
Figure 122:
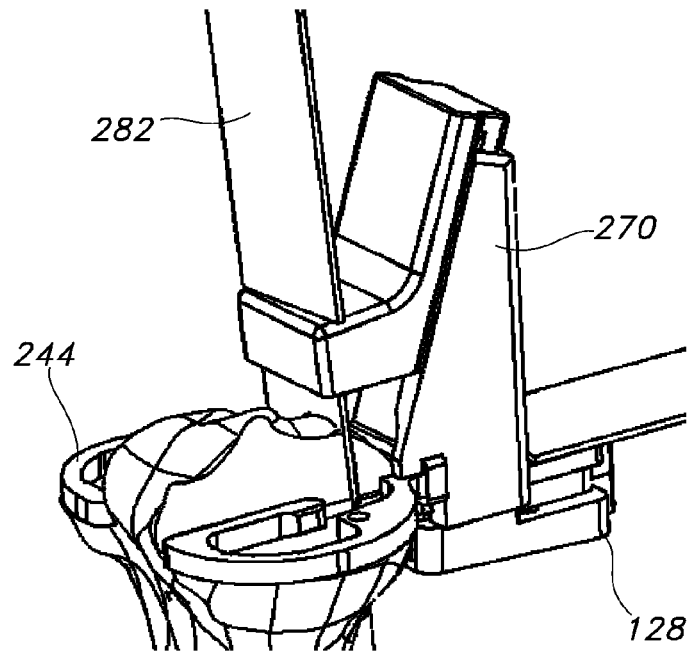
Figures 123, 124:
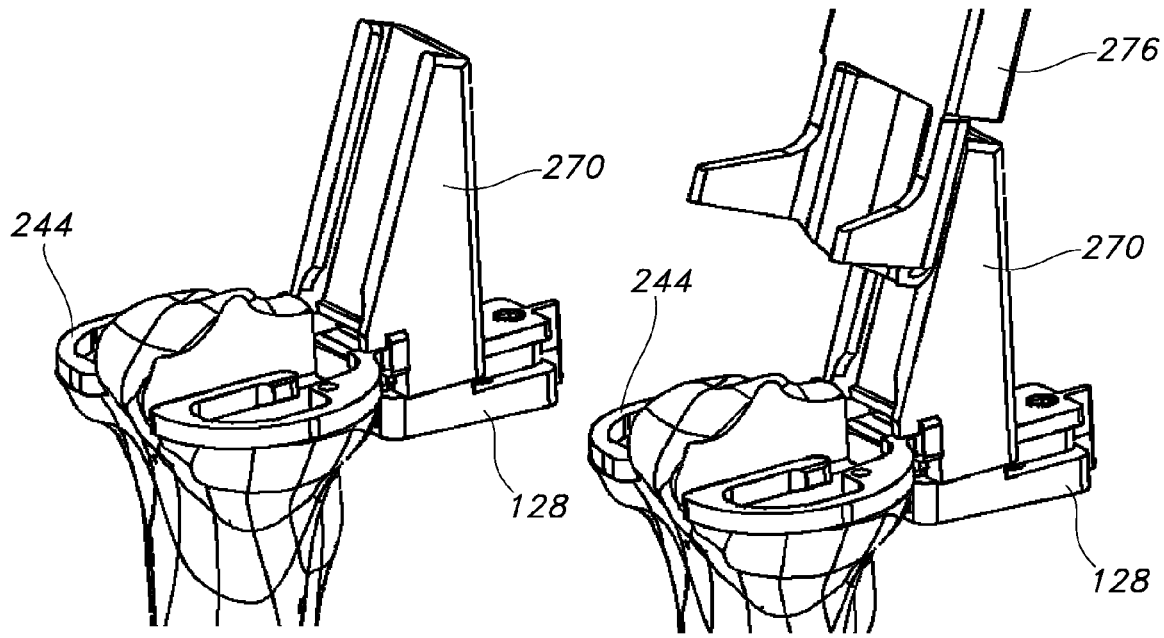
Figures 125, 126:
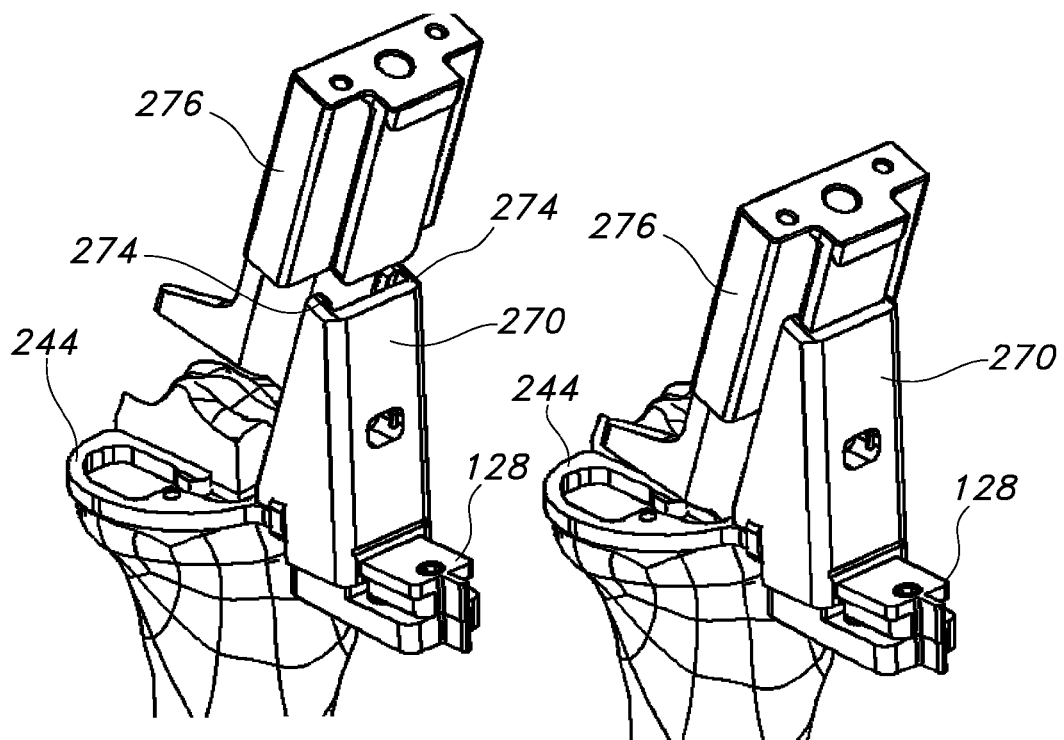
Figures 127, 128:
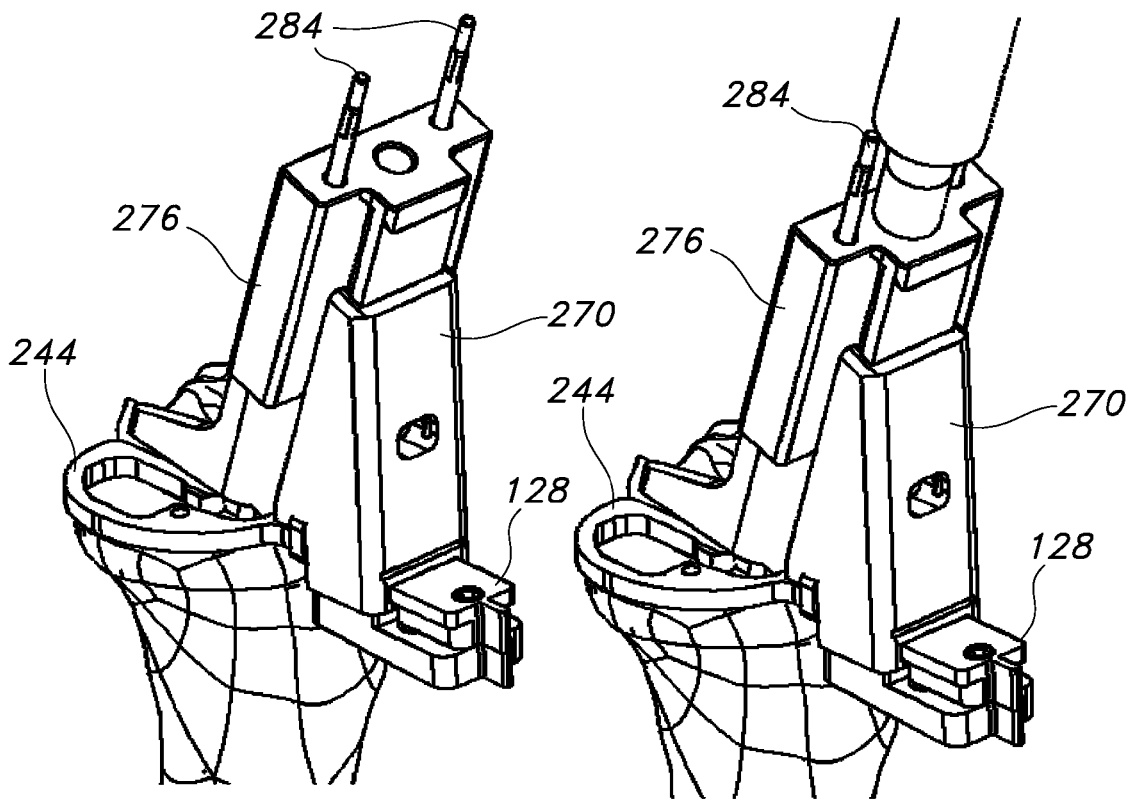
Figures 129, 130:
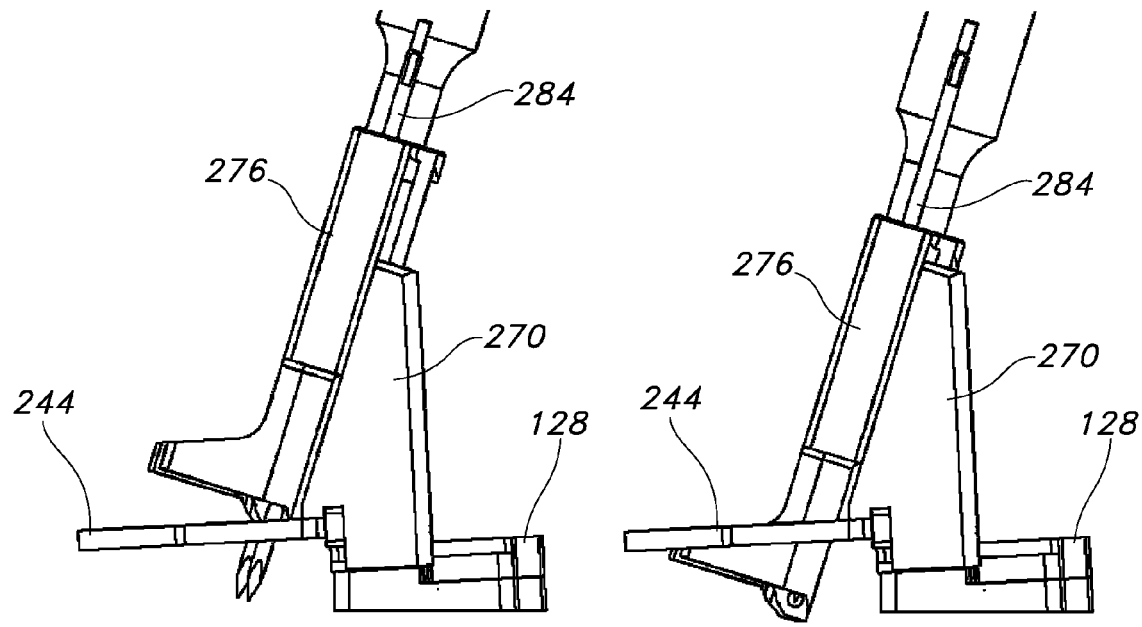
Figures 131, 132:
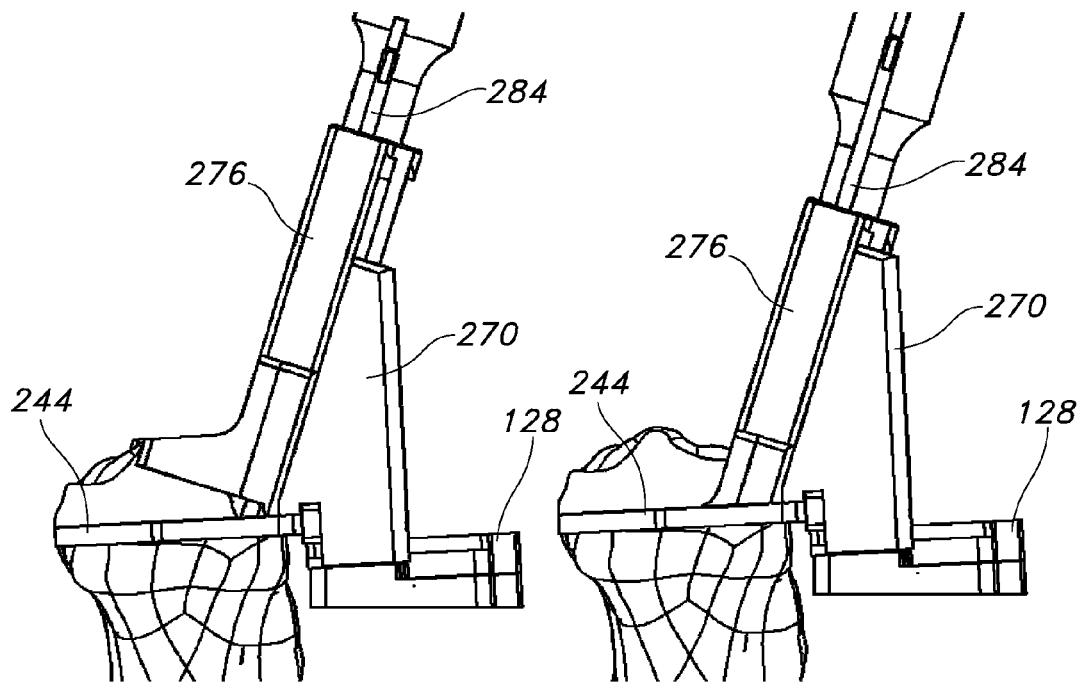
Figures 133, 134:
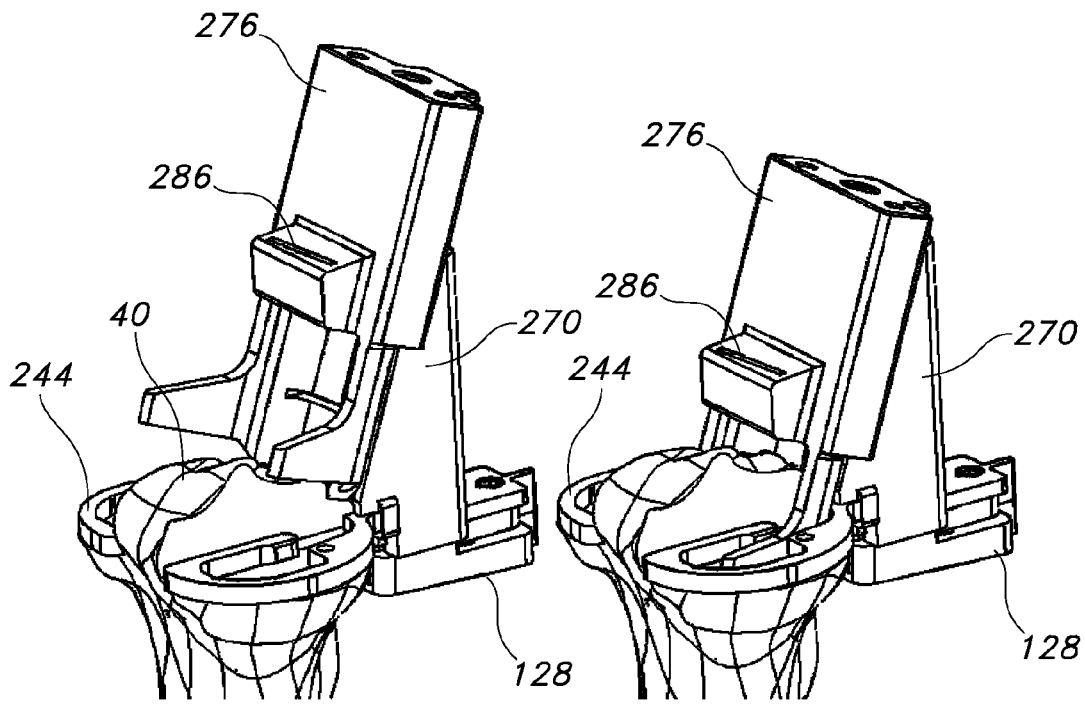

FIGS. 113 through 157 show various embodiments of a guide 270 that may be fastened directly to the tibial baseplate 244 and tibia 12 using pins or other means for securement (such as shown for example in FIG. 149) or indirectly to the tibial baseplate using an intermediate component such as secondary alignment block 128 or another component (such as shown for example in FIG. 116). Guide 270 may be used, in some embodiments, to guide punch 276 for forming a keel cavity 272 (see, e.g., FIGS. 124 and 140) in the proximal tibia 12 for receiving the keel of a tibial implant, and, in these or other embodiments, may also be used to guide one or more chisels 282 or other cutters to remove anterior portions of the tibial eminence 40 (as illustrated by, for example, FIG. 121).

The precision offered by the tibial baseplate 244 when it is used, in some embodiments, as a control reference for the positioning of the guide 270 and other instrumentation can be desirable, as it can help ensure that there is no mismatch conflict between the tibial eminence 40 and the punched keel cavity 272 when the surgeon inserts the final tibial tray baseplate implant. Since the implant will mate or at least correspond to both portions of the tibial eminence 40 and the punched keel cavity 272 in some embodiments, it can be important that the two are positioned correctly relative to each other so that the implant does not bind, become tilted, or sit proud after insertion.

As shown by, for example, the embodiment of FIGS. 133 through 139, the guide 270 has a recessed portion which provides clearance over and around the anterior portion of the tibial eminence 40. The guide 270 also includes structure (such as pair of slots 274 shown for instance in FIG. 125 or other appropriate structure such as a dovetailed guide) configured to guide a punch 276 or other bone removal instrument (e.g., broach, mill, cutting blade, saw blade, chisel) into the proximal tibia 12 in a controlled manner.

In one embodiment (see, e.g., FIGS. 133 through 134), punch 276 is configured to create a keel cavity 272 at an insertion angle. The punch may be asymmetric or symmetric and may comprise one or more wing portions to create a generally "U-shaped" keel cavity. In some embodiments, a smaller punch or broach may be used first to lessen the impaction force necessary to form the keel cavity 272. As mentioned above, in some embodiments, the tibia baseplate 244 may define a gap of appropriate size and shape to receive the U-shaped punch.

In some embodiments, the insertion angle of the punch 276 is non-perpendicular (in some embodiments obtuse) to the plateau resections and matches the keel angle of a tibial implant to reduce the risk of punching through or fracturing the anterior cortical bone of the tibia. The guide 270 ensures that the punch 276 travels at a consistent predetermined angle and orientation during insertion. An alternative embodiment (not shown) allows for various sections of the keel to be punched individually.

Figure 155:
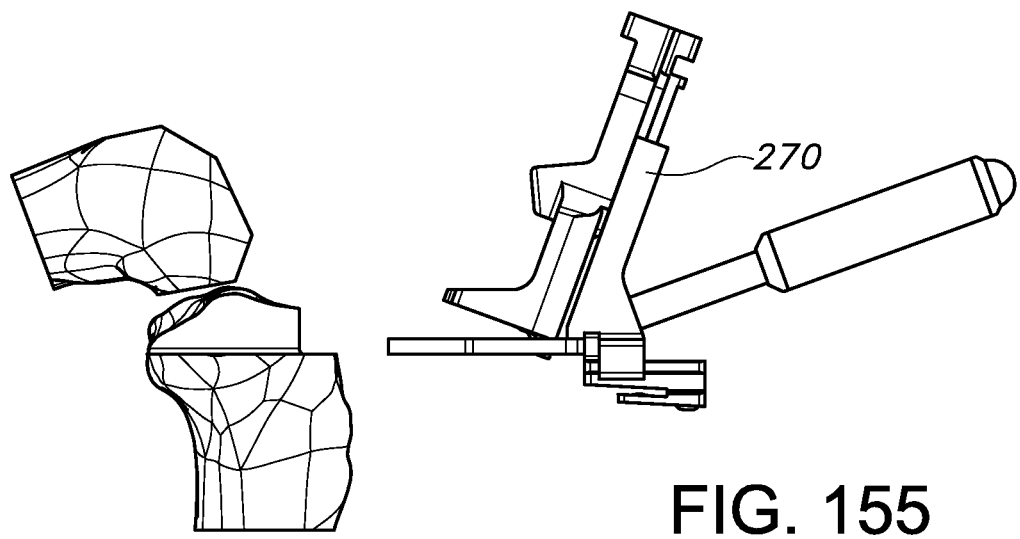
Figure 156:
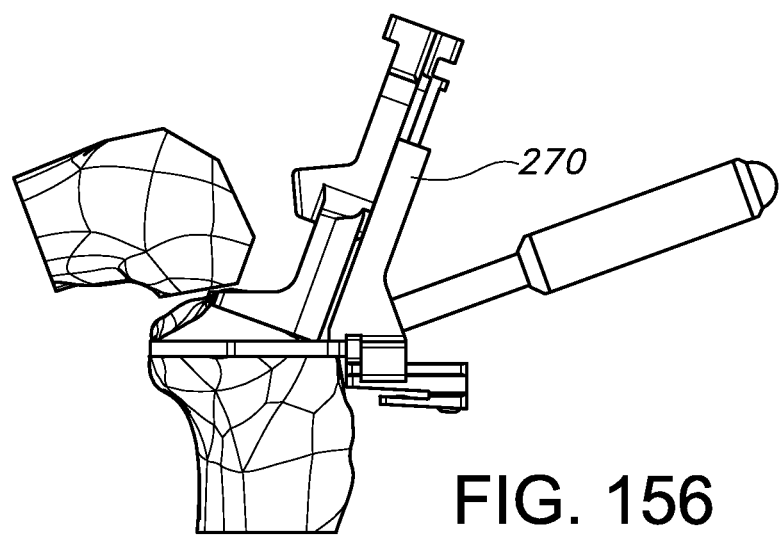
Figure 157:
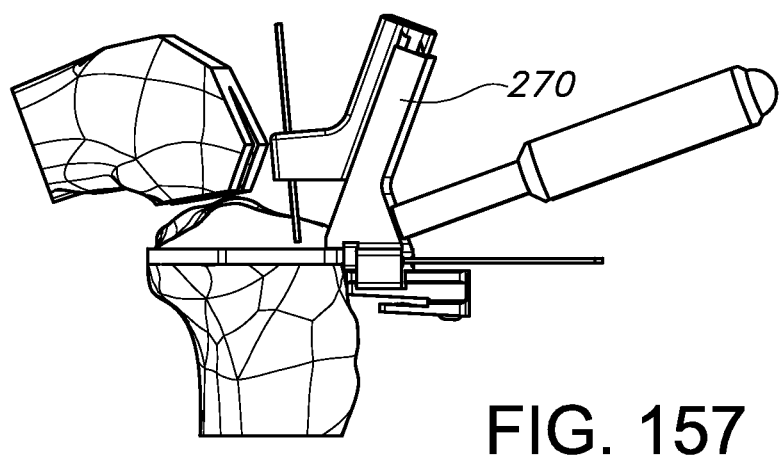

Because the insertion angle of the punch 276 is not orthogonal to the medial and lateral plateau resections, a user may tend to flex the punch 276 when impacting or the punch 276 may tend to extend or bow during impact. In order to avoid these problems, in some embodiments, stability can be added to the punch construct by various means. A first means for providing stability comprises an optional handle as shown in FIGS. 155 through 157. In these or other embodiments, further securement may be achieved by attachment of the alignment block 102 to the secondary alignment block 128 so that the punch guide 270, tibial baseplate 244, secondary alignment block 128, alignment block 102, and/or extramedullary rod 36 can be connected together. By positively connecting all of the aforementioned instruments, enhanced stability is provided to the guide 270, though it should be noted that use of fewer securing devices is possible for reduction of complexity and opening of workspace. In other embodiments, other combinations of these and other instrumentation and other apparatus can be used to position the guide 270. In still other embodiments, offset impactors (e.g. having impact surfaces that are not linearly aligned with an end associated with the punch) could be utilized instead of or in addition to the above described mechanisms to maintain appropriate alignment of the punch.

As shown in FIGS. 127 through 132, long drill pins 284 may also be pre-inserted into the tibia to reduce the amount of force necessary to punch the keel cavity (especially at corners of the punch), and reduce stress concentrations at the keel cavity corners by rounding out the sharp corners. The long drill pins 284 may also serve as guide pins to aid in guiding and stabilizing the punch 276 at said insertion angle.

The anterior portion of the eminence may be removed before (e.g. FIGS. 121 through 126) or after (FIGS. 133 through 139) punching. If the anterior portion of the eminence 40 is removed after the punch 276 is fully seated in the tibia 12, one or more chisel slots 286 may be integrally provided on any one of: the punch, an anterior portion of the tibial baseplate, or an anterior portion of the guide. If the punching step is performed properly prior to anterior eminence removal, in these embodiments, the chisel slots 286 will be in the optimal position for resecting and removing the anterior portion of the tibial eminence. Multiple captured chisel slots, uncaptured chisel slots, or planar guide surfaces may be provided on or adjacent to the punch.

Figures 143, 144:
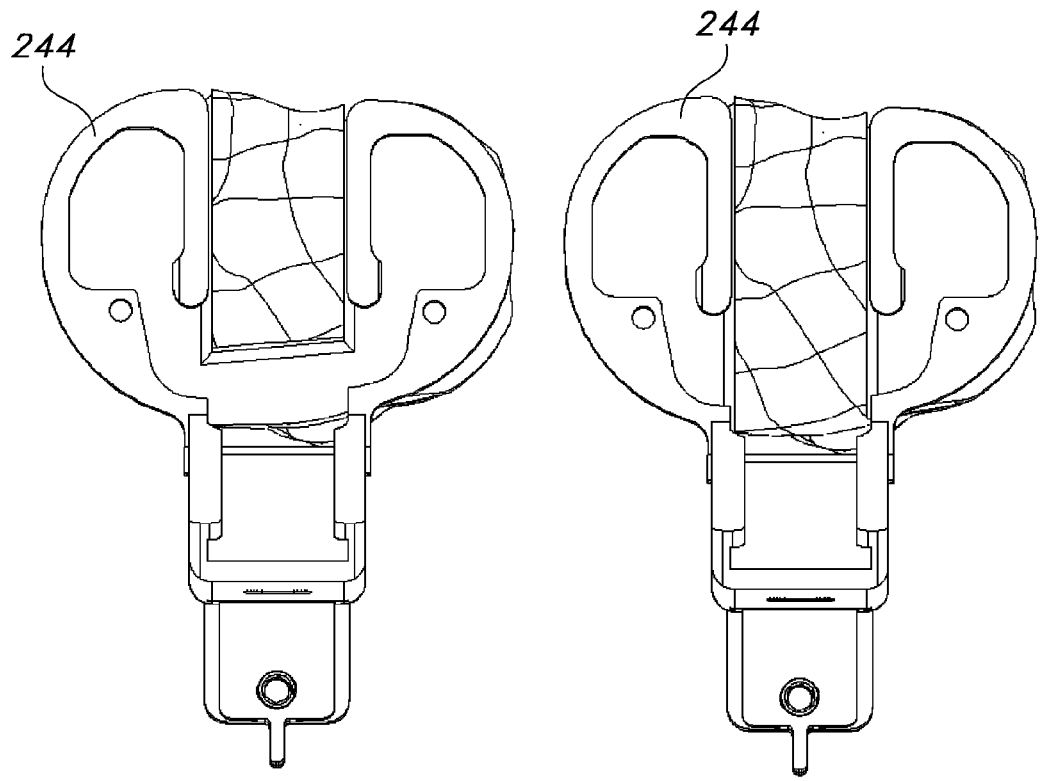
Figures 145, 146:
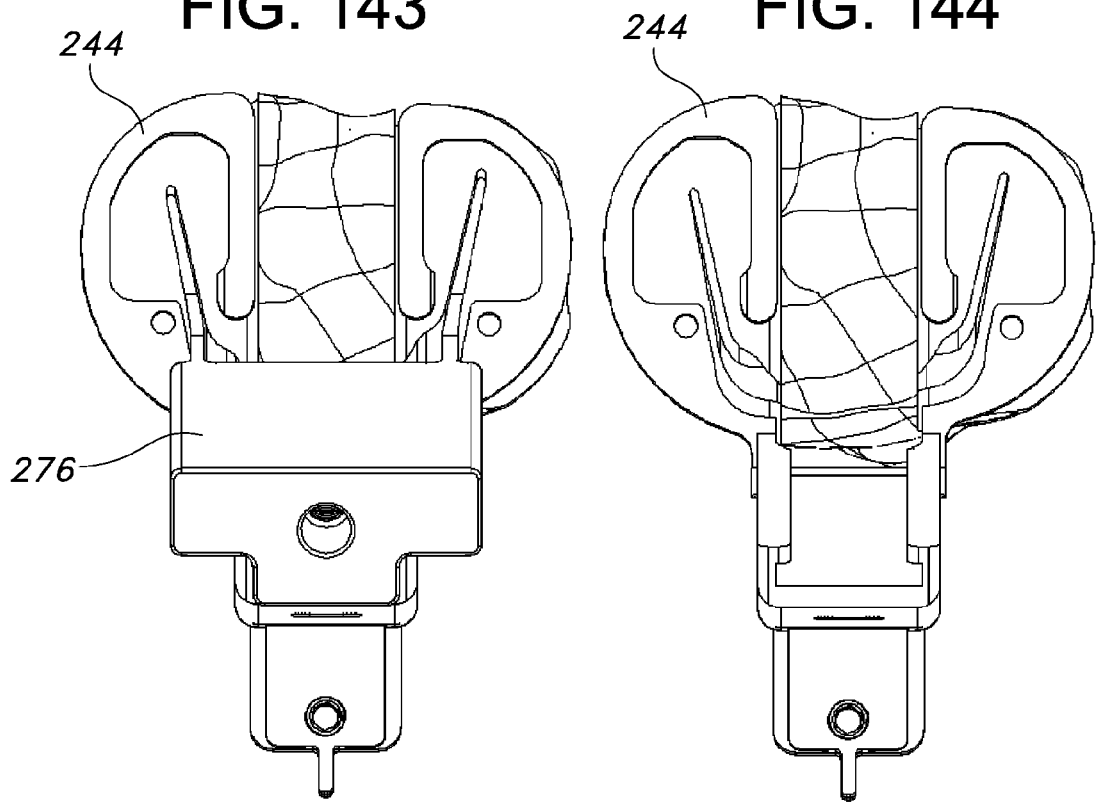

In some embodiments, chisel slots may be configured to provide an anterior eminence bone cut that is oriented in a substantially vertical position as shown in FIGS. 140 and 141. In some embodiments, chisel slots may be oriented to provide an anterior eminence bone cut which is positioned at angles relative to said substantially vertical position as shown in FIG. 142. In some embodiments, the chisel slots may be oriented with some internal or external rotation as shown in FIG. 147 to provide angled anterior eminence bone cuts as shown in FIG. 143.

In some embodiments, removing the anterior eminence can make the step of punching a keel cavity easier, because there is less bone for the punch to penetrate after the anterior portion of the tibial eminence is removed. However, removing the anterior eminence after punching will ensure that the anterior eminence bone cut, anterior plateau resection, and keel cavity are all properly aligned with respect to each other. Instrument kits according to the invention may be provided with options to perform one or both methods. The keel cavity is preferably made using a single punch; however, a set of two or more punches may be provided to form the keel cavity sequentially, and thereby removing small amounts of bone at a time. For instance, a preliminary broaching punch having one or more smaller dimensions than a finishing broaching punch may be provided to gradually open the keel cavity without fracturing the bone. Preliminary broaching steps may be preferred in cases of very dense or sclerotic tibial bone.

Figure 138:
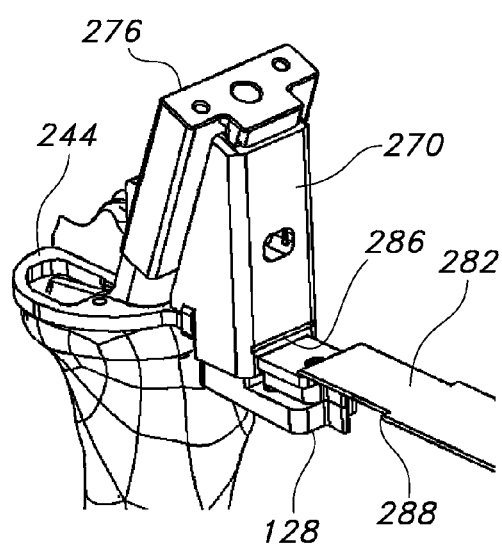
Figure 139:
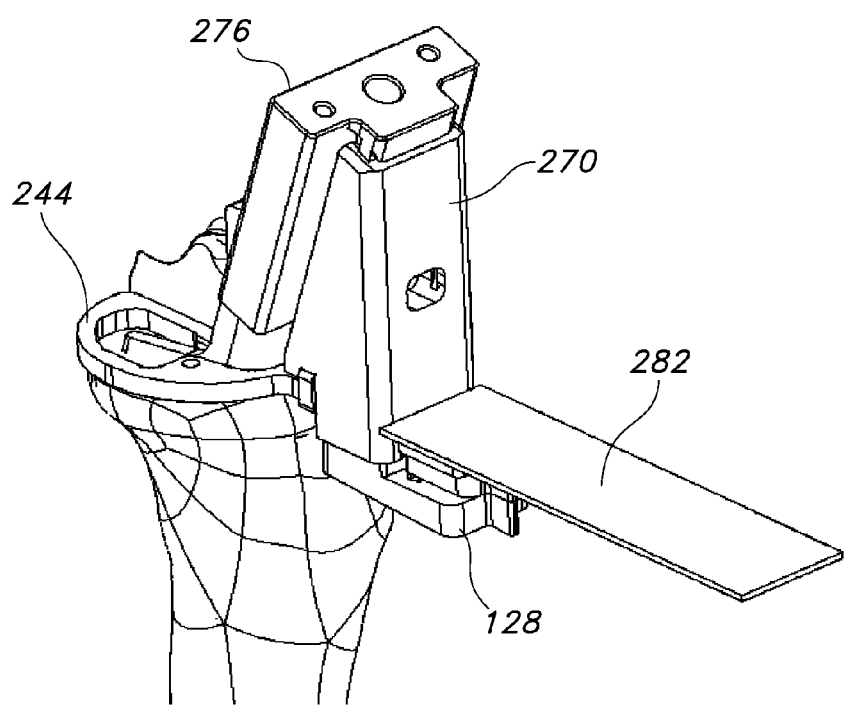

As shown for example in FIG. 138, additional chisel slots 286 may be provided on an anterior portion of the guide 270 to facilitate an anterior plateau resection. In one preferred embodiment, the anterior plateau resection is generally oriented substantially horizontally and co-planar to the medial and lateral plateau resections. However, other embodiments may incorporate chisel slots configured to make an anterior plateau resection parallel with or at an angle with respect to the medial and lateral plateau resections. The meeting of the generally horizontal anterior plateau resection and the generally vertical anterior eminence resection effectively removes an anterior block portion of the tibial eminence.

Figure 137:
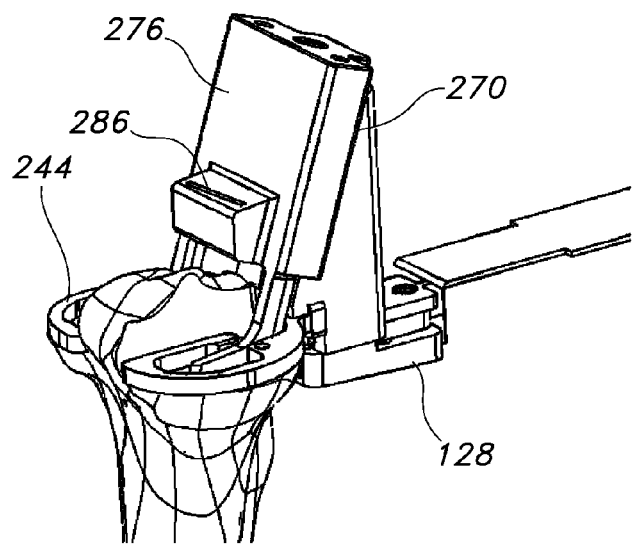

Any one of the tibial baseplate, punch guide, and cutting tool may be provided with a means for limiting travel of the cutting tool such as a flange, a stop portion, a lip, or a step portion, or an interference portion. For instance, FIGS. 137 and 138 shows chisels 282 with stops 288 formed thereon. Such stops 288 or other structures or mechanisms can be used to prevent or lessen the likelihood of eminence notching.

Stops 288 or other stopping mechanisms may be calibrated for limiting a penetration depth for both the horizontal anterior plateau resection and the generally vertical anterior eminence resection. Those mechanisms may provide equal or different amounts of chisel depth penetration for the anterior eminence bone cut and anterior plateau resection. In some embodiments, the stop 288 will allow the use of a single chisel for both the anterior eminence bone cut and anterior plateau resection.

Figures 135, 136:
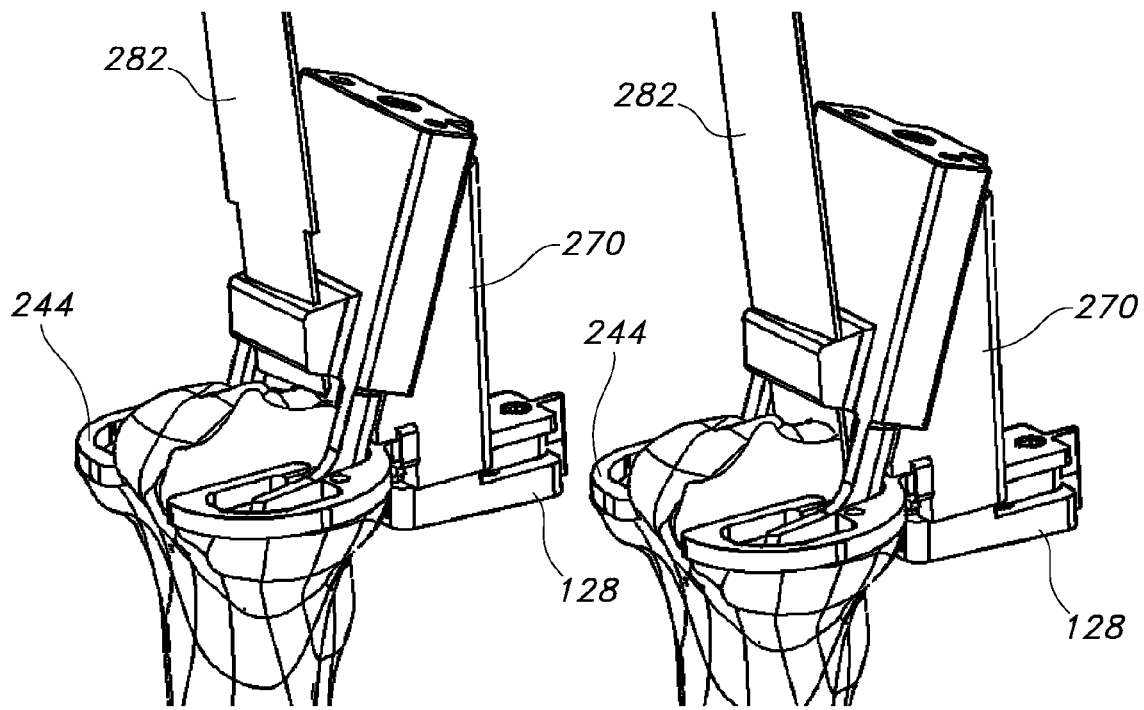
Figure 150:
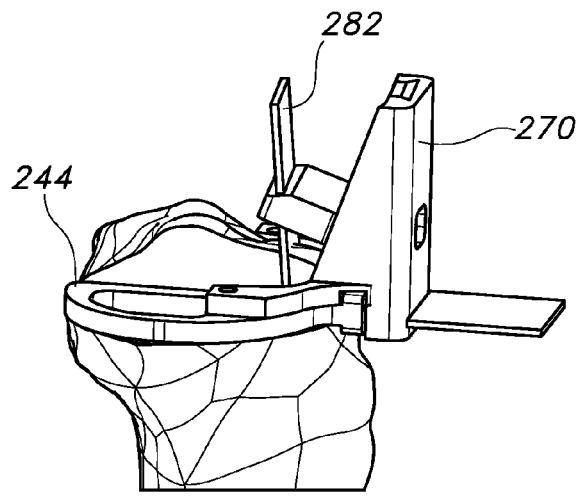
Figure 151:
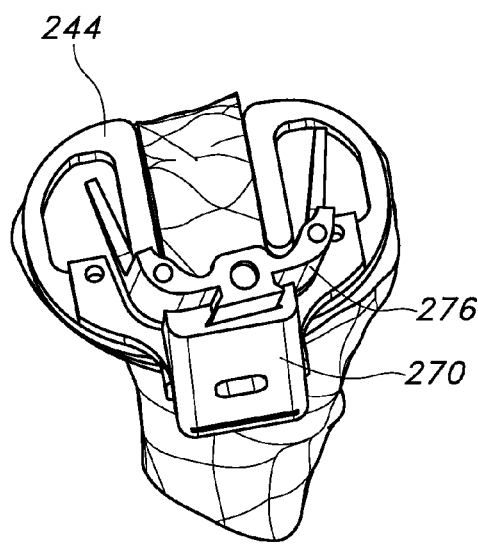
Figure 152:
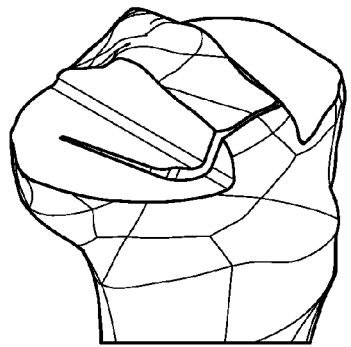

The chisel slots 286 for making the generally vertical anterior eminence bone cuts are shown as integral with the punch 276 in FIGS. 135 through 137. They may alternatively be provided in a separate chisel guide block adapted to cooperate directly with the guide 270 such as shown in the embodiment of FIG. 150. However, making the anterior eminence bone cut through a slot that is integral and monolithic with the punch 276 as shown in FIGS. 133 through 139 allows the relationship between the anterior eminence and the punched keel cavity to be held to a tighter tolerance, thereby providing a better fit of the tibial implant, and, in some embodiments, although not all, may therefore be preferable. In some embodiments, similar control of the placement of the anterior eminence is achieved by providing chisel slots on the guide 270. In other words, an anterior eminence chisel may be guided by means for guiding provided on the guide 270 itself. In this way, the generally vertical anterior eminence bone cuts may be made either before or after punching. The means for guiding provided on the punch guide may be, for example, a cantilevered extension of the punch guide having a guide slot thereon.

Figure 153:
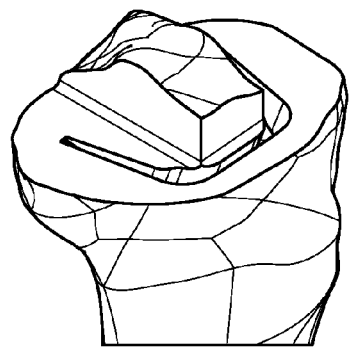
Figure 154:
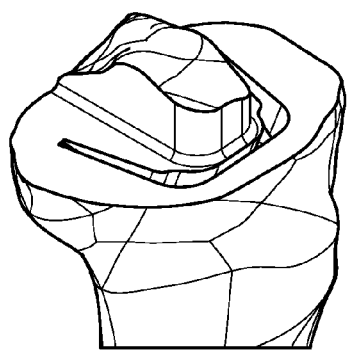

After punching a keel cavity and removing the anterior portion of the tibial eminence, the antero-medial and antero-lateral eminence corners shown in FIG. 153 can be rounded to form eminence radii as shown in FIG. 154. The eminence radii generally serve to provide clearance for the installed tibial implant, and are made by trimming the sharp antero-medial and antero-lateral eminence corners with a rongeur tool or other desirable tools. Alternatively, eminence radii may be formed by cutting die features formed in the punch.

Figure 158:
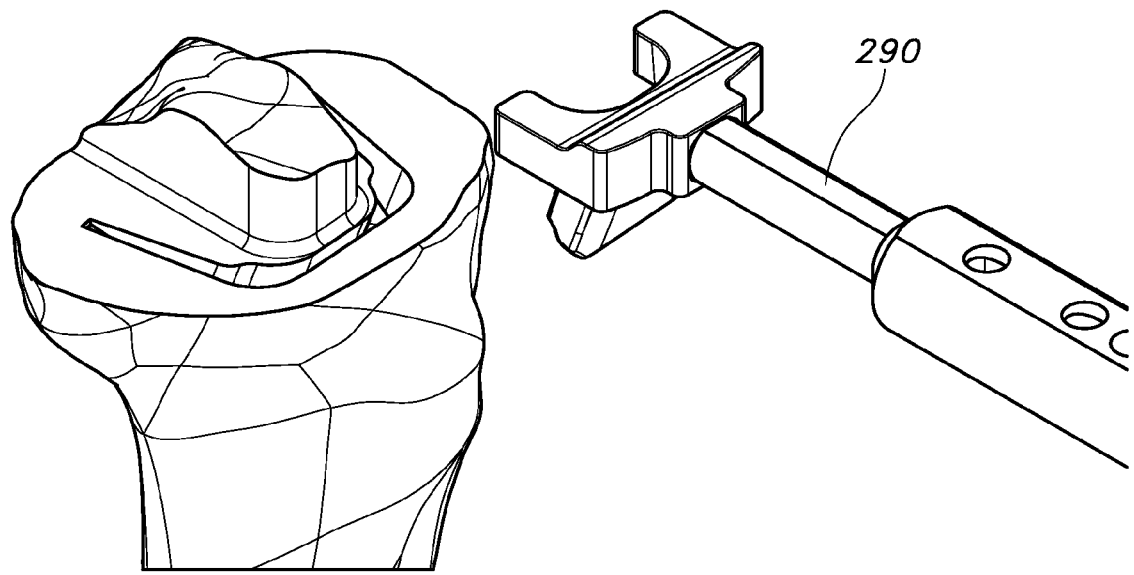
Figure 159:
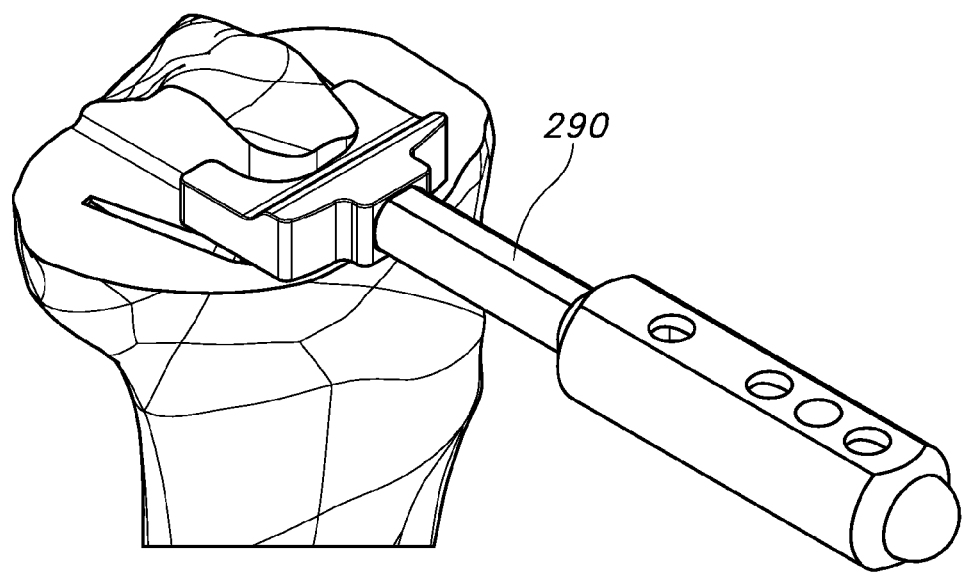

After the above preparation steps are completed, the prepared proximal tibia 12 may be gauged with a gauge 290 simulating the shape and size of the corresponding implant to be installed as shown in FIGS. 158 and 159. The gauge 290 generally serves to provide the surgeon information relating to implant fit, and more specifically ensures that when the final implant is seated within the prepared keel cavity, it will mate properly with the eminence, and not interfere or cause interference or binding with the eminence. After the prepared proximal tibia is gauged, implantation of the final tibial implants may proceed in a conventional manner.

Additional Embodiments

In some embodiments, significant cost savings are enjoyed when manufacturing the instruments disclosed herein. For example, tibial baseplates according to some embodiments are both asymmetric and ambidextrous; in other words, chirality is not a necessity, but can be present if desired, for certain instruments to be used on either left or right legs. For instance, for each tibial baseplate size, a tibial baseplate may be inverted to work with either a left tibia or a right tibia. The lateral plateau resection guide may also be ambidextrous, meaning it can be used on either a left tibia or a right tibia.

A large number of asymmetric tibial trial inserts creates a need to manage the large inventory. For example, trials must be provided for both medial and lateral condyles of both left and right knees. In addition, the trials must come in a sufficient number of sizes (e.g., 4-6 size options), thicknesses (e.g., 6 thickness options), and posterior slope angle options (e.g., high, standard, reduced). In some embodiments, up to 192 trial inserts could be necessary to cover a sufficient number of surgical options. Some embodiments address this issue by providing several means for reducing system complexity. According to some embodiments, one means for reducing system complexity is building posterior slope angle options into the tibial baseplates rather than into the inserts themselves. In this manner, there are only two or so baseplate trials (each having a different slope) for each particular tibial implant size. Building posterior slope angle into the tibial baseplates will effectively double the number of necessary tibial baseplates in the system, (e.g., from 8 to 16); however, will generally reduce the number of necessary tibial trial inserts by approximately 50% (e.g., from 192 to 96).

It should be noted that adjustability features may be transferred between parts. In some instances, for example, the secondary alignment block may have superior-inferior adjustment capabilities built in, instead of the alignment block. In other instances, the alignment block may be provided with means for selectively or infinitely adjusting the posterior slope of the medial plateau resection, instead of the secondary alignment block. Moreover, a means for medial-lateral direction adjustment of the stylus may be provided to any one of the secondary alignment block, alignment block, or medial plateau resection guide in some embodiments.

It should also be understood that method steps disclosed herein may be performed in any order regardless of the order in which they are presented, and that while a medial cut first method may be preferable in some embodiments, the surgical techniques provided may be adapted for a lateral plateau cut first method.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the claimed invention should not be limited by any of the above-described exemplary embodiments, but should be defined only in accordance with the following claims appended hereto and their equivalents.

The invention claimed is:

1. A surgical kit for arthroplasty on a knee joint, the surgical kit comprising at least one distal femoral trial for evaluating a distal femoral resection of a distal femur, wherein the distal femoral trial comprises: a body having a proximal-most surface and a distal surface, the proximal-most surface being a planar, proximal facing surface for contact with medial and lateral portions of the distal femoral resection of medial and lateral condyles; the distal surface being an inferior, curved surface defining medial and lateral condylar surfaces for contact with an unresected surface on a proximal tibia; and the body defining, between the medial and lateral condylar surfaces, a gap configured to admit at least a portion of a retained cruciate ligament through the body when the proximal-most surface is in contact with the distal femoral resection.

2. The surgical kit of claim 1, wherein the distal femoral trial is a gauge for gauging internal/external rotation, anterior/posterior position, medial/lateral position, or size of the distal femoral trial with respect to the distal femur.

3. The surgical kit of claim 2, wherein the distal femoral trial includes one or more references located on the distal femoral trial to indicate an expected position and orientation of a femoral implant with respect to the distal femur.

4. The surgical kit of claim 3, wherein the references are located to indicate a position of the distal femoral trial with respect to posterior medial and posterior lateral edges of the distal femoral resection.

5. The surgical kit of claim 4, wherein the one or more references for indicating the position of the distal femoral trial with respect to posterior medial and posterior lateral edges of the distal femoral resection comprise posterior edges of the inferior, curved surface of the distal femoral trial.

6. The surgical kit of claim 1, wherein the distal femoral trial includes one or more openings defined through the distal femoral trial, the one or more openings being located in the distal femoral trial to expose a central anterior V point of the distal femoral resection through the distal surface of the distal femoral trial when the proximal-most surface of the distal femoral trial is engaged with the distal femoral resection and posterior edges of the distal femoral trial are located at posterior edges of the distal femoral resection.

7. The surgical kit of claim 1, wherein the distal femoral trial defines a window extending through the distal femoral trial from the proximal-most surface to the distal surface, the window being located anterior to the gap and extending in a medial/lateral direction along a central portion of the gap.

8. The surgical kit of claim 1, wherein the body is substantially U-shaped.

9. The surgical kit of claim 8, wherein the distal femoral trial substantially replicates at least one of a shape, a thickness, and a size of an inferior portion of a bicruciate retaining femoral implant.

10. The surgical kit of claim 1, wherein the distal femoral trial is part of a set of distal femoral trials of different sizes of distal femoral trials, and the different sizes of distal femoral trials substantially replicate distal portions of different sizes of femoral implants.

11. The surgical kit of claim 1, wherein the distal femoral trial is modular.

12. The surgical kit of claim 11, wherein the surgical kit comprises a plurality of shims for varying a thickness of the distal femoral trial.

13. The surgical kit of claim 12, wherein the surgical kit comprises a plurality of shims for varying a thickness of a lateral condylar portion of the distal femoral trial.

14. The surgical kit of claim 11, wherein the surgical kit comprises a plurality of shims for varying at least one of a varus/valgus angle and a flexion/extension angle.

15. The surgical kit of claim 1, wherein the distal femoral trial is part of a set of distal femoral trials of different thicknesses.

16. The surgical kit of claim 1, wherein the distal femoral trial is part of a set of distal femoral trials, each of the distal femoral trials being shaped to produce a different varus/valgus angle or a different range of flexion/extension angles in the knee joint.

17. The surgical kit of claim 1, further comprising an alignment block for securement to the proximal tibia, wherein the alignment block is connectable to the distal femoral trial, wherein the alignment block is connectable to the distal femoral trial in a fixed angular position.

18. The surgical kit of claim 1, further comprising an alignment block for securement to the proximal tibia; wherein the distal femoral trial includes an attachment site for connecting the alignment block to the distal femoral trial.

19. The surgical kit of claim 18, further comprising a connector for connecting the alignment block to the distal femoral trial in a fixed angular orientation.

20. The surgical kit of claim 18, further comprising a connector for connecting the alignment block to the distal femoral trial such that a planar bench of the alignment block is parallel to the proximal, planar surface of the distal femoral trial.

21. The surgical kit of claim 1, further comprising an indicator for indicating a posterior slope of the proximal tibial resection, a varus/valgus angle of the proximal tibial resection, or a depth of the proximal tibial resection;
wherein the distal femoral trial includes an attachment site for associating the indicator with the distal femoral trial.

22. The surgical kit of claim 1, wherein the proximal-most surface is substantially U-shaped.

23. The surgical kit of claim 1, wherein the distal femoral resection has posterior edges and the body has posterior edges, and wherein the body defines one or more windows through the body, the one or more windows being located in the body such that the one or more windows extend directly over a central anterior V point of the distal femoral resection when the posterior edges of the body are aligned with the posterior edges of the distal femoral resection.

24. The surgical kit of claim 1, wherein the body defines one or more windows that are each located lateral to the medial condylar surface and medial to the lateral condylar surface.

25. A surgical kit for arthroplasty on a knee joint, the surgical kit comprising at least one distal femoral trial for evaluating a distal femoral resection of a distal femur, wherein the distal femoral trial comprises: a body having a proximal-most surface and a distal surface, the proximal-most surface being a planar, proximal facing surface for contact with medial and lateral portions of the distal femoral resection of medial and lateral condyles, the body being substantially U-shaped in the plane of the planar, proximal-most surface; and the distal surface being an inferior, curved surface defining at least one condylar surface for contact with an unresected surface on a proximal tibia.

26. The surgical kit of claim 25, wherein the proximal-most surface is configured to simultaneously engage medial and lateral portions of the distal resection, and the body defines a gap configured to admit a retained anterior cruciate ligament of the knee joint while the proximal-most surface is engaged with the medial and lateral portions of the distal resection.

27. The surgical kit of claim 1, wherein the medial and lateral condylar surfaces curve distally, away from the proximal-most surface.

28. The surgical kit of claim 25, wherein the medial and lateral condylar surfaces are convex distal-facing surfaces.

29. The surgical kit of claim 7, wherein the window is medially and laterally bounded by the distal femoral trial.

30. The surgical kit of claim 29, wherein the window defines an arcuate opening through the proximal-most surface.

31. The surgical kit of claim 1, wherein the distal femoral trial defines first window and a second window, the first window and second window each extending through the distal femoral trial from the proximal-most surface to the distal surface, the first window being located anterior to the gap and the second window being located anterior to the first window, the first window and the second window each having a perimeter defined by the distal femoral trial.

32. A surgical kit for arthroplasty on a knee joint, the surgical kit comprising at least one distal femoral trial for evaluating a distal femoral resection of a distal femur, wherein the distal femoral trial comprises: a body having a proximal-most surface and a distal surface, the proximal-most surface being a planar, proximal facing surface for contact with the distal femoral resection; the distal surface being an inferior, curved surface defining medial and lateral condylar surfaces having condylar radii for contact with an unresected surface on a proximal tibia; and the body defining, between the medial and lateral condylar surfaces, a gap configured to admit at least a portion of a retained cruciate ligament through the body when the proximal-most surface is in contact with the distal femoral resection.

33. The surgical kit of claim 32, wherein the body is substantially U-shaped.

34. The surgical kit of claim 32, wherein the distal femoral trial is part of a set of distal femoral trials of different sizes of distal femoral trials, and the different sizes of distal femoral trials substantially replicate distal portions of different sizes of femoral implants.

35. The surgical kit of claim 32, wherein the distal femoral trial is part of a set of distal femoral trials of different thicknesses.

36. The surgical kit of claim 32, wherein the distal femoral trial is part of a set of distal femoral trials, each of the distal femoral trials being shaped to produce a different varus/valgus angle or a different range of flexion/extension angles in the knee joint.

37. The surgical kit of claim 32, wherein the distal femoral trial is modular.

38. The surgical kit of claim 32, further comprising an alignment block for securement to the proximal tibia; wherein the distal femoral trial includes an attachment site for connecting the alignment block to the distal femoral trial.

39. The surgical kit of claim 38, further comprising a connector for connecting the alignment block to the distal femoral trial in a fixed angular orientation.

40. The surgical kit of claim 38, further comprising a connector for connecting the alignment block to the distal femoral trial such that a planar bench of the alignment block is parallel to the proximal, planar surface of the distal femoral trial.

41. The surgical kit of claim 32, further comprising an indicator for indicating a posterior slope of the proximal tibial resection, a varus/valgus angle of the proximal tibial resection, or a depth of the proximal tibial resection; wherein the distal femoral trial includes an attachment site for associating the indicator with the distal femoral trial.

42. A surgical kit for arthroplasty on a knee joint, the surgical kit comprising at least one distal femoral trial for evaluating a distal femoral resection of a distal femur, wherein the distal femoral trial comprises: a body having a proximal-most surface and a distal surface, the proximal-most surface being a planar, proximal facing surface for contact with the distal femoral resection, the body being substantially U-shaped in the plane of the planar, proximal-most surface; and the distal surface being an inferior, curved surface defining at least one condylar surface having condylar radii for contact with an unresected surface on a proximal tibia.

43. The surgical kit of claim 42, wherein the proximal-most surface is configured to simultaneously engage medial and lateral portions of the distal resection, and the body defines a gap configured to admit a retained anterior cruciate ligament of the knee joint while the proximal-most surface is engaged with the medial and lateral portions of the distal resection.

* * * * *